United States Patent
Yip et al.

(10) Patent No.: US 10,217,619 B2
(45) Date of Patent: Feb. 26, 2019

(54) METHODS FOR DATA-DEPENDENT MASS SPECTROMETRY OF MIXED INTACT PROTEIN ANALYTES

(71) Applicant: Thermo Finnigan LLC, San Jose, CA (US)

(72) Inventors: Ping F. Yip, Salem, MA (US); James L. Stephenson, Jr., Raleigh, NC (US); Oksana Gvozdyak, Bedford, MA (US)

(73) Assignee: THERMO FINNIGAN LLC, San Jose, CA (US)

( * ) Notice: Subject to any disclaimer, the term of this patent is extended or adjusted under 35 U.S.C. 154(b) by 0 days.

(21) Appl. No.: 15/067,727

(22) Filed: Mar. 11, 2016

(65) Prior Publication Data
US 2016/0268112 A1    Sep. 15, 2016

Related U.S. Application Data

(60) Provisional application No. 62/132,124, filed on Mar. 12, 2015.

(51) Int. Cl.
*G01N 33/68* (2006.01)
*H01J 49/00* (2006.01)

(52) U.S. Cl.
CPC ...... *H01J 49/0036* (2013.01); *G01N 33/6848* (2013.01); *G01N 33/6851* (2013.01); *H01J 49/004* (2013.01); *H01J 49/0031* (2013.01)

(58) Field of Classification Search
CPC .................................................... G01N 33/68
USPC ............................................. 436/86–89, 173
See application file for complete search history.

(56) References Cited

U.S. PATENT DOCUMENTS 5,072,115 A * 12/1991 Zhou ............... H01J 49/0036
                                                    250/252.1
6,894,276 B1 *  5/2005 Takada ............. G01N 33/0057
                                                    250/282
7,158,862 B2 *  1/2007 Liebler ............ H01J 49/0036
                                                    250/281

(Continued)

FOREIGN PATENT DOCUMENTS

WO    2008/151140 A2    12/2008
WO    2013/112677 A2    8/2013

(Continued)

OTHER PUBLICATIONS

Davis, M. T. et al, Journal of the American Society for Mass Spectrometry 1997, 8, 1059-1069.*

(Continued)

*Primary Examiner* — Arlen Soderquist
(74) *Attorney, Agent, or Firm* — Thomas F. Cooney

(57) ABSTRACT

A method for mass spectral analysis of a sample containing a plurality of biomolecule species comprises: (a) mass analyzing a plurality of first-generation ion species generated from a sample portion; (b) automatically recognizing, for each of at least one biomolecule species, a respective subset of m/z ratios corresponding to respective first-generation ion species generated from the each biomolecule species; (c) selecting, from each recognized subset, a single representative m/z ratio; (d) isolating a sub-population of ions having each representative m/z ratio from ions having other m/z ratios; and (e) fragmenting each isolated sub-population of ions so as to generate second-generation ion species.

26 Claims, 40 Drawing Sheets

(56) References Cited

U.S. PATENT DOCUMENTS

| | | | |
|---|---|---|---|
| 7,297,941 B2 | 11/2007 | Senko et al. | |
| 7,407,810 B2* | 8/2008 | Raguram | G01N 33/48 436/71 |
| 7,473,892 B2* | 1/2009 | Sano | G01N 33/6848 250/281 |
| 7,982,181 B1* | 7/2011 | Senko | G01N 30/72 250/281 |
| 8,053,723 B2 | 11/2011 | Senko | |
| 8,105,838 B2* | 1/2012 | Gorenstein | G01N 30/72 436/86 |
| 2002/0119490 A1* | 8/2002 | Aebersold | G01N 33/6803 435/7.1 |
| 2004/0181351 A1 | 9/2004 | Thompson et al. | |
| 2004/0251409 A1* | 12/2004 | Le Blanc | H01J 49/0045 250/288 |
| 2005/0063864 A1* | 3/2005 | Sano | G01N 33/6848 422/68.1 |
| 2005/0098719 A1 | 5/2005 | Thomson | |
| 2006/0284067 A1* | 12/2006 | Senko | G01N 30/8603 250/282 |
| 2007/0095757 A1* | 5/2007 | Kaplan | G01N 30/8675 210/656 |
| 2008/0001079 A1* | 1/2008 | Wang | H01J 49/0036 250/282 |
| 2008/0048109 A1* | 2/2008 | Schwartz | H01J 49/0031 250/282 |
| 2008/0093547 A1 | 4/2008 | Hartmer et al. | |
| 2008/0283740 A1* | 11/2008 | Hashiba | H01J 49/0027 250/288 |
| 2009/0215103 A1* | 8/2009 | Gorenstein | G01N 30/72 435/24 |
| 2010/0133428 A1* | 6/2010 | Matsui | H01J 49/0045 250/281 |
| 2010/0203139 A1* | 8/2010 | Baker, Jr. | A61K 9/1075 424/484 |
| 2010/0213368 A1* | 8/2010 | Wang | H01J 49/0036 250/282 |
| 2010/0276586 A1* | 11/2010 | Senko | H01J 49/429 250/283 |
| 2010/0286927 A1* | 11/2010 | Horn | H01J 49/0036 702/19 |
| 2011/0020910 A1* | 1/2011 | Glass | C07K 14/37 435/252.31 |
| 2011/0288779 A1 | 11/2011 | Satulovsky | |
| 2011/0297823 A1* | 12/2011 | Coon | H01J 49/004 250/282 |
| 2012/0156707 A1 | 6/2012 | Hartmer et al. | |
| 2012/0261568 A1* | 10/2012 | Coon | G06F 19/18 250/282 |
| 2013/0068943 A1* | 3/2013 | Heaven | G01N 30/7233 250/282 |
| 2013/0090862 A1* | 4/2013 | Krokhin | G01N 30/7233 702/21 |
| 2013/0206979 A1* | 8/2013 | Bonner | H01J 49/0031 250/282 |
| 2013/0240722 A1 | 9/2013 | Coon et al. | |
| 2013/0240723 A1* | 9/2013 | Bonner | H01J 49/0045 250/282 |
| 2013/0297226 A1* | 11/2013 | Wang | H01J 49/0036 702/23 |
| 2014/0120565 A1* | 5/2014 | Coon | G01N 33/6848 435/23 |
| 2014/0303903 A1* | 10/2014 | Fujita | H01J 49/0036 702/23 |
| 2014/0357526 A1* | 12/2014 | Caprioli | G01N 33/6848 506/12 |
| 2015/0246913 A1* | 9/2015 | Gray | C07D 471/04 514/253.03 |
| 2015/0247149 A1* | 9/2015 | Feldstein | G01N 33/5308 424/158.1 |
| 2016/0187350 A1* | 6/2016 | Bertozzi | G01N 33/6848 506/12 |
| 2016/0258958 A1* | 9/2016 | Narain | G01N 33/57434 |

FOREIGN PATENT DOCUMENTS

| | | |
|---|---|---|
| WO | 2013/166169 A1 | 11/2013 |
| WO | 2014/116711 A1 | 7/2014 |
| WO | 2014/150040 A2 | 9/2014 |
| WO | 2016/011355 A1 | 1/2016 |

OTHER PUBLICATIONS

Zhang, Z. et al, Journal of the American Society for Mass Spectrometry 1998, 9, 225-233.*
Spahr, C. S. et al, Proteomics 2001, 1, 93-107.*
Davis, M. T. et al, Proteomics 2001, 1, 108-117.*
Li. L. et al, Analytical Chemistry 2001, 73, 3312-3322.*
Syka, J. E. P. et al, Journal of Proteome Research 2004, 3, 621-626.*
Scherl, A. et al, Proteomics 2004, 4, 917-927.*
Stewart, I. I. et al, Rapid Communications in Mass Spectrometry 2004, 18, 1697-1710.*
Venable, J. D. et al, Nature Methods 2004, 1, 1-7.*
Chen, H.-S. et al, Analytical Chemistry 2005, 77, 7816-7825.*
Tabb, D. L. et al, Journal of the American Society for Mass Spectrometry 2006, 17, 903-915.*
Mueller, L. N. et al, Proteomics 2007, 7, 3470-3480.*
Wang, N. et al, Analytical Chemistry 2008, 80, 4696-4710.*
Jaffe, J. D. et al, Molecular & Cellular Proteomics 2008, 7, 1952-1962.*
Schmidt, A. et al, Molecular & Cellular Proteomics 2008, 7, 2138-2150.*
Swaney, D. L. et al, Nature Methods 2008, 5, 959-964.*
Bendall, S. C. et al, Molecular & Cellular Proteomics 2009, 8, 421-432.*
Rudomin, E. L. et al, Journal of Proteome Research 2009, 8, 3154-3160.*
Zerck, A. et al, Journal of Proteome Research 2009, 8, 3239-3251.*
Schmidt, A. et al, Current Opinion in Chemical Biology 2009, 13, 510-517.*
Sweredoski, M. J. et al, Journal of Biomolecular Techniques 2011, 22, 122-126.*
Bonnell, E. et al, in "Sample Preparation in Biological Mass Spectrometry", Ivanov, A. R. et al, editors, Springer, 2011, 691-714.*
Banerjee, S. et al, International Journal of Analytical Chemistry 2012, Article ID 282574, 40 pages.*
Graumann, J. et al, Molecular & Cellular Proteomics 2012, 11, Article 10.1074/mcp.M111.013185, 11 pages.*
Gillet, L. C. et al, Molecular & Cellular Proteomics 2012, 11, Article 10.1074/mcp.O111.016717, 17 pages.*
Rost, H. et al, Molecular & Cellular Proteomics 2012, 11, Article 10.1074/mcp.M111.013045, 540-549.*
Guthals, A. et al, Molecular & Cellular Proteomics 2012, 11, Article 10.1074/mcp.M111.015768, 1084-1096.*
Gallien, S. et al, Molecular & Cellular Proteomics 2012, 11, Article 10.1074/mcp.O112.019802, 1709-1723.*
Cannon, J. R.e et al, Journal of Mass spectrometry 2013, 48, 340-343.*
Zerck, A. et al, BMC Bioinformatics 2013, 14, Article 56, 14 pages*
Zerck A., Dissertation 2013, 142 pages.*
Webber, J. T. et al, Proteomics 2013, 13, 1412-1416.*
Saeed, F. et al, IEEE International Conference on Bioinformatics and Biomedicine (BIBM) 2012, 516-519.*
Pollak, M., "The Game Changer for Post-Translational Modification Analysis" 2014, 2 pages downloaded from https://www.thermofisher.com/blog/proteomics/the-game-changer-for-post-translational-modification-analysis/.*
Covey, T. R. et al, Rapid Communications in Mass Spectrometry 1988, 2, 249-256.*
Mann, M. et al, Analytical Chemistry 1989, 61, 1702-1708.*

(56) References Cited

OTHER PUBLICATIONS

Labowsky, M. et al, Rapid Communications in Mass Spectrometry 1993, 7, 71-84.*
Ashton, D. S. et al, FEBS Letters 1994, 342, 1-6.*
Hofstaler, S. A. et al, Journal of CHemical Education 1996, 73, A82-A87.*
Krishnamurthy, T. et al, Rapid Communications in Mass Spectrometry 1999, 13, 39-49.*
Bruce, J. E. et al, Journal of the American Society for Mass Spectromtery 2000, 11, 416-421.*
Frankevich, V. et al, Rapid Communications in Mass Spectrometry 2003, 17, 2343-2348.*
van der Burgt, Y. E. M. et al, Journal of the American Society for Mass Spectromtery 2007, 18, 152-161.*
Mujezinovic, N. Dissertaion 2007, 142 pages, downloaded from https://www.ac.tuwien.ac.at/files/pub/mujezinovic_07.pdf.*
Barbu, I. M. Thesis 2008, 176 pages, downloaded from https://amolf.nl/publications/fourier-transform-ion-cyclotron-resonance-imaging-mass-spectrometry-development-of-instrumentation-data-acquisition-software-and-data-processing-methods.*
Liu, Z, et al, Journal of the American Society for Mass Spectromtery 2008, 19, 231-238.*
Heck, A. J. R., Nature Methods 2008, 5, 927-933.*
Winkler, R., Rapid Communications in Mass Spectrometry 2010, 24, 285-294.*
Liu, X. et al, Molecular & Cellular Proteomics 2010, 9, 2772-2782.*
Pearcy, J. O. et al, Journal of the American Society for Mass Spectrometry 2001, 12, 599-606.*
Tseng, Y.-H. et al, Analytical Chemistry 2011, 83, 1960-1968.*
Kalli et al., "Evaluation and Optimization of Mass Spectrometric Settings During Data-dependent Acquisition Mode: Focus on LTQ-Orbitrap Mass Analyzers," J. Proteome Res., 2013, 12, pp. 3071-3086.
Senko et al., "Automated Assignment of Charge States from Resolved Isotopic Peaks for Multiply Charged Ions", J Am Soc Mass Spectrom 1995, 6, pp. 52-56.
Horn, et al., "Automated Reduction and Interpretation of High Resolution Electrospray Mass Spectra of Large Molecules," J. Am. Soc. Mass Spectrom., vol. 11, No. 4., (2000), pp. 320-332.

* cited by examiner

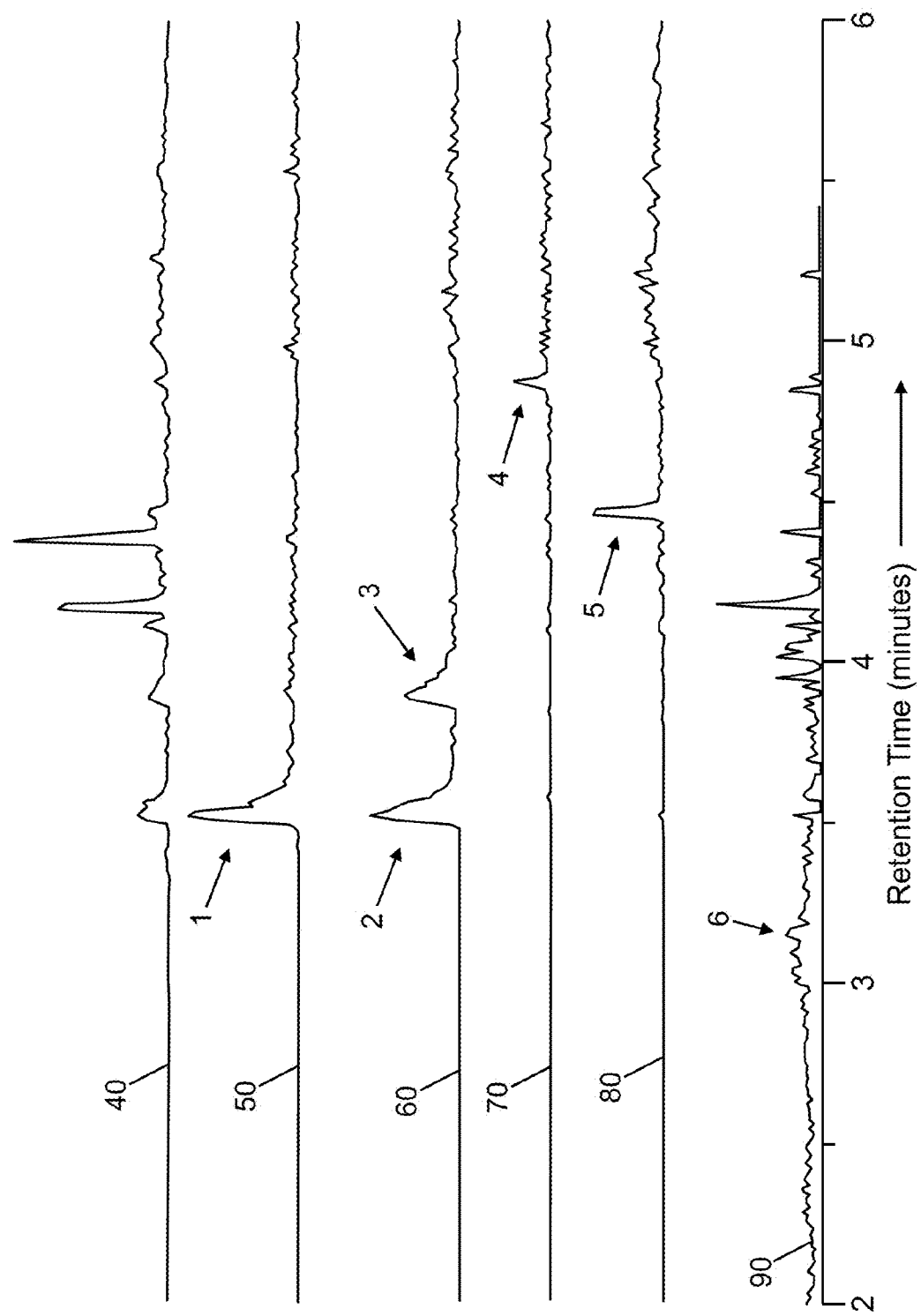

400

Convert Centroid Data to Discretized Array Form

Build Boolean Occupancy Array — 420

Build Relative Separation Matrix (RSM)

$$\mathrm{RSM}_{z1,z2} = \frac{\ln(z_2/z_1)}{D}$$

460

420

Build Boolean Occupancy Array

422 — Subset $\{\mathcal{F}\}$: Filter Centroids by Intensity or S/N

424 — For each $C_i$ in $\mathcal{F}$,
$$T(m/z)_i = \ln\!\left((m/z)_i - M_{\text{proton}}\right)$$
$(i = 1, \ldots, n)$ 426 — Choose greatest, $T(m/z)_{\text{Hi}}$, and smallest, $T(m/z)_{\text{Lo}}$, values in $\mathcal{F}$ 428 — Boolean Occupancy Array $[O_k]$:
$O_k := \text{FALSE}; \ (k = 1, \ldots, L_{\text{occs}})$
$$L_{\text{occs}} = \frac{(T(m/z)_{\text{Hi}} - T(m/z)_{\text{Lo}})}{D}$$

430 — Assign index, $k$, to each $C_i$ in $\mathcal{F}$:
$$k_i := \text{ROUND}\left[\frac{(T(m/z)_i - T(m/z)_{\text{Lo}})}{D}\right]$$

432 — Resolution, $R_i$ known?

434a (Y):
$$k_i^{\text{Lo}} := \frac{(T(m/z)_i - 0.5\,R_i)}{D}$$
$$k_i^{\text{Hi}} := \frac{(T(m/z)_i + 0.5\,R_i)}{D}$$

434b (N):
$k_i^{\text{Lo}} := k_i - 1$
$k_i^{\text{Hi}} := k_i + 1$

436 — $O_k := \text{TRUE}; \quad k_i^{\text{Lo}} \leq k_i \leq k_i^{\text{Hi}}$

End

FIG. 6

Table 1

| No. C$^{12}$ | MW(typical) | Mode(C$^{13}$) | Ave(C$^{13}$) | Ave − Mode |
|---|---|---|---|---|
| 50 | 1100 | 0 | 0.535 | 0.535 |
| 100 | 2200 | 1 | 1.07 | 0.07 |
| 150 | 3300 | 1 | 1.605 | 0.605 |
| 200 | 4400 | 2 | 2.14 | 0.14 |
| 250 | 5500 | 2 | 2.675 | 0.675 |
| 300 | 6600 | 3 | 3.21 | 0.21 |
| 350 | 7700 | 3 | 3.745 | 0.745 |
| 400 | 8800 | 4 | 4.28 | 0.28 |
| 450 | 9900 | 4 | 4.815 | 0.815 |
| 500 | 11000 | 5 | 5.35 | 0.35 |
| 550 | 12100 | 5 | 5.885 | 0.885 |
| 600 | 13200 | 6 | 6.42 | 0.42 |
| 650 | 14300 | 6 | 6.955 | 0.955 |
| 700 | 15400 | 7 | 7.49 | 0.49 |
| 750 | 16500 | 8 | 8.025 | 0.025 |
| 800 | 17600 | 8 | 8.56 | 0.56 |
| 850 | 18700 | 9 | 9.095 | 0.095 |
| 900 | 19800 | 9 | 9.63 | 0.63 |
| 950 | 20900 | 10 | 10.165 | 0.165 |
| 1000 | 22000 | 10 | 10.7 | 0.7 |
| 1050 | 23100 | 11 | 11.235 | 0.235 |
| 1100 | 24200 | 11 | 11.77 | 0.77 |
| 1150 | 25300 | 12 | 12.305 | 0.305 |
| 1200 | 26400 | 12 | 12.84 | 0.84 |
| 1250 | 27500 | 13 | 13.375 | 0.375 |

FIG. 10A

Table 1 (continued)

| No. $C^{12}$ | MW(typical) | Mode($C^{13}$) | Ave($C^{13}$) | Ave − Mode |
|---|---|---|---|---|
| 1300 | 28600 | 13 | 13.91 | 0.91 |
| 1350 | 29700 | 14 | 14.445 | 0.445 |
| 1400 | 30800 | 14 | 14.98 | 0.98 |
| 1450 | 31900 | 15 | 15.515 | 0.515 |
| 1500 | 33000 | 16 | 16.05 | 0.05 |
| 1550 | 34100 | 16 | 16.585 | 0.585 |
| 1600 | 35200 | 17 | 17.12 | 0.12 |
| 1650 | 36300 | 17 | 17.655 | 0.655 |
| 1700 | 37400 | 18 | 18.19 | 0.19 |
| 1750 | 38500 | 18 | 18.725 | 0.725 |
| 1800 | 39600 | 19 | 19.26 | 0.26 |
| 1850 | 40700 | 19 | 19.795 | 0.795 |
| 1900 | 41800 | 20 | 20.33 | 0.33 |
| 1950 | 42900 | 20 | 20.865 | 0.865 |
| 2000 | 44000 | 21 | 21.4 | 0.4 |
| 2050 | 45100 | 21 | 21.935 | 0.935 |
| 2100 | 46200 | 22 | 22.47 | 0.47 |
| 2150 | 47300 | 23 | 23.005 | 0.005 |
| 2200 | 48400 | 23 | 23.54 | 0.54 |
| 2250 | 49500 | 24 | 24.075 | 0.075 |
| 2300 | 50600 | 24 | 24.61 | 0.61 |
| 2350 | 51700 | 25 | 25.145 | 0.145 |
| 2400 | 52800 | 25 | 25.68 | 0.68 |
| 2450 | 53900 | 26 | 26.215 | 0.215 |
| 2500 | 55000 | 26 | 26.75 | 0.75 |

FIG. 10B

Table 1 (continued)

| No. $C^{12}$ | MW(typical) | Mode($C^{13}$) | Ave($C^{13}$) | Ave − Mode |
|---|---|---|---|---|
| 2550 | 56100 | 27 | 27.285 | 0.285 |
| 2600 | 57200 | 27 | 27.82 | 0.82 |
| 2650 | 58300 | 28 | 28.355 | 0.355 |
| 2700 | 59400 | 28 | 28.89 | 0.89 |
| 2750 | 60500 | 29 | 29.425 | 0.425 |
| 2800 | 61600 | 29 | 29.96 | 0.96 |
| 2850 | 62700 | 30 | 30.495 | 0.495 |
| 2900 | 63800 | 31 | 31.03 | 0.03 |
| 2950 | 64900 | 31 | 31.565 | 0.565 |
| 3000 | 66000 | 32 | 32.1 | 0.1 |
| 3050 | 67100 | 32 | 32.635 | 0.635 |
| 3100 | 68200 | 33 | 33.17 | 0.17 |
| 3150 | 69300 | 33 | 33.705 | 0.705 |
| 3200 | 70400 | 34 | 34.24 | 0.24 |
| 3250 | 71500 | 34 | 34.775 | 0.775 |
| 3300 | 72600 | 35 | 35.31 | 0.31 |
| 3350 | 73700 | 35 | 35.845 | 0.845 |
| 3400 | 74800 | 36 | 36.38 | 0.38 |
| 3450 | 75900 | 36 | 36.915 | 0.915 |
| 3500 | 77000 | 37 | 37.45 | 0.45 |
| 3550 | 78100 | 37 | 37.985 | 0.985 |
| 3600 | 79200 | 38 | 38.52 | 0.52 |
| 3650 | 80300 | 39 | 39.055 | 0.055 |
| 3700 | 81400 | 39 | 39.59 | 0.59 |
| 3750 | 82500 | 40 | 40.125 | 0.125 |

FIG. 10C

Table 1 (continued)

| No. C$^{12}$ | MW(typical) | Mode(C$^{13}$) | Ave(C$^{13}$) | Ave − Mode |
|---|---|---|---|---|
| 3800 | 83600 | 40 | 40.66 | 0.66 |
| 3850 | 84700 | 41 | 41.195 | 0.195 |
| 3900 | 85800 | 41 | 41.73 | 0.73 |
| 3950 | 86900 | 42 | 42.265 | 0.265 |
| 4000 | 88000 | 42 | 42.8 | 0.8 |
| 4050 | 89100 | 43 | 43.335 | 0.335 |
| 4100 | 90200 | 43 | 43.87 | 0.87 |
| 4150 | 91300 | 44 | 44.405 | 0.405 |
| 4200 | 92400 | 44 | 44.94 | 0.94 |
| 4250 | 93500 | 45 | 45.475 | 0.475 |
| 4300 | 94600 | 46 | 46.01 | 0.01 |
| 4350 | 95700 | 46 | 46.545 | 0.545 |
| 4400 | 96800 | 47 | 47.08 | 0.08 |
| 4450 | 97900 | 47 | 47.615 | 0.615 |
| 4500 | 99000 | 48 | 48.15 | 0.15 |
| 4550 | 100100 | 48 | 48.685 | 0.685 |
| 4600 | 101200 | 49 | 49.22 | 0.22 |
| 4650 | 102300 | 49 | 49.755 | 0.755 |
| 4700 | 103400 | 50 | 50.29 | 0.29 |
| 4750 | 104500 | 50 | 50.825 | 0.825 |
| 4800 | 105600 | 51 | 51.36 | 0.36 |
| 4850 | 106700 | 51 | 51.895 | 0.895 |
| 4900 | 107800 | 52 | 52.43 | 0.43 |
| 4950 | 108900 | 52 | 52.965 | 0.965 |
| 5000 | 110000 | 53 | 53.5 | 0.5 |

FIG. 10D

Assignment Controls

| | MS1 | MS2 |
|---|---|---|
| Mass Accuracy in ppm: | 10 | 10 |
| Peaks Intensity Threshold: | 50000 | 25000 |
| Peaks S/N Threshold: | 10 | 5 |
| Lowest Charge State: | 1 | 1 |
| Highest Charge State: | 50 | 50 |

FIG. 11B

Clustering Controls

| | MS1 | MS2 |
|---|---|---|
| Minimum Contiguous Charge States | 3 | 3 |
| Minimum Contiguous Isotopes | 5 | 3 |
| Sufficient Contiguous Charge States | 5 | 5 |
| Sufficient Contiguous Isotopes | 7 | 4 |
| Mass Separation | 15 | 15 |

FIG. 11C

Table 2. Accuracy of Calculated Molecular Weights of Standard Proteins

| Protein Name | Theoretical Average MW | Average MW Observed ±1σ | Mode MW Observed ±1σ | PPM Error | Theoretical Monoisotopic MW | Monoisotopic Observed MW | PPM Error |
|---|---|---|---|---|---|---|---|
| Ribonuclease A | 13682.3075 | 13681.7861 ± 0.7069 | 13681.9864 ± 0.4825 | 38.11 / 23.47 | 13673.2534 | 13672.8594 ± 0.5176 | 28.82 |
| Myoglobin | 16951.499 | 16950.7227 ± 0.4876 | 16950.9263 ± 0.3168 | 45.79 / 33.78 | 16940.960 | 16939.7886 ± 0.4256 | 68.97 |
| Trypsin Inhibitor | 19975.6092 | 19976.4137 ± 0.9641 | 19976.6108 ± 0.5140 | 40.28 / 50.14 | 19963.0067 | 19963.4758 ± 0.5249 | 23.50 |
| Carbonic Anhydrase | 29024.4864 | 29024.1855 ± 1.061 | 29024.1855 ± 0.8574 | 5.071 / 1.544 | 29006.7056 | 29005.2291 ± 0.7203 | 50.91 |
| Enolase | 46670.974 | 46670.9273 ± 1.130 | 46670.3255 ± 0.8133 | 1.00 / 13.90 | 46656.209 | N/A | N/A |

FIG. 16

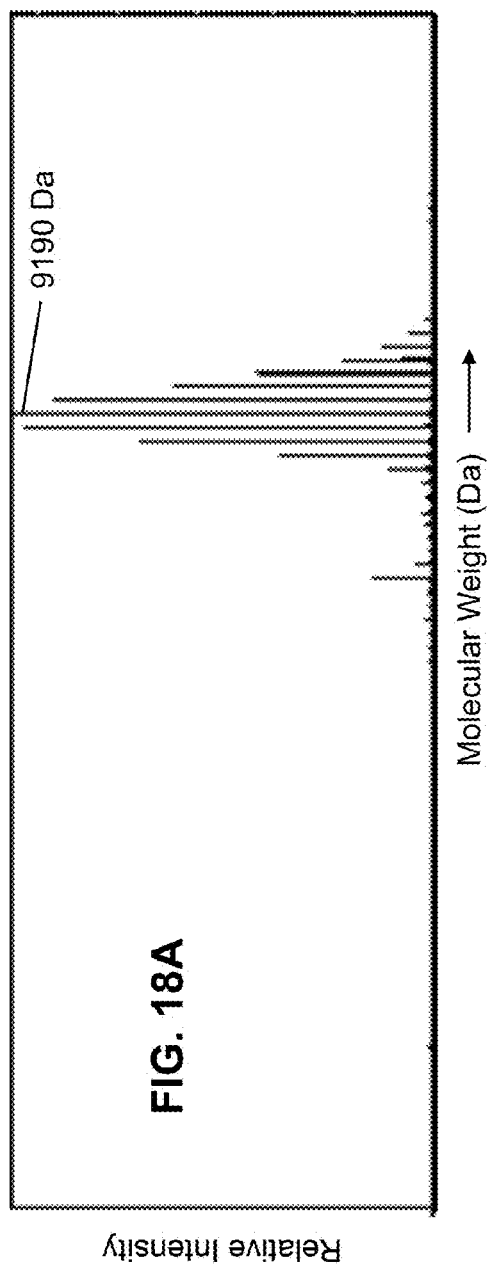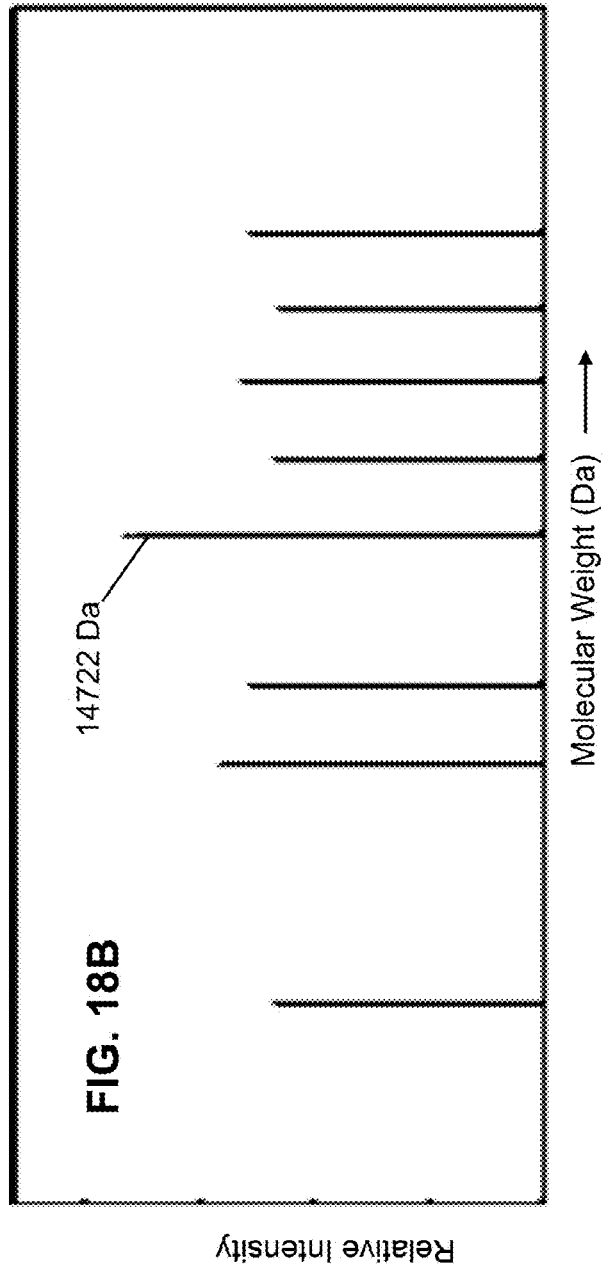

Table 3. Distinguishing Protein Molecular Weights of Closely Related Bacterial Species

| E. coli (11775) | S. sonnei (29930) | S. maltophilia (13637) | P. geniculata (19374) | A. denitrificans (15173) | A. xyloxidans (27061) | P. vulgaris (29905) | P. penneri (33519) |
|---|---|---|---|---|---|---|---|
|  | 8,322 |  | 7,372 |  | 5,232 |  | 10,647 |
| 8,347 |  | 9,072 | 9,057 |  | 9,587 | 10,972 |  |
|  | 9,737 |  |  |  |  |  | 10,987 |
| 11,212 | 11,182 | 9,342 | 9,312 |  | 11,587 | 13,212 |  |
| 14,722 |  | 9,652 |  | 14,542 | 11,822 |  | 15,182 |
|  | 14,747 |  | 9,667 |  | 14,492 | 15,192 |  |
| 16,017 | 15,902 |  | 9,887 | 16,227 | 15,827 |  | 16,137 |
|  |  | 12,647 | 10,512 | 18,667 | 15,842 | 17,137 |  |
| 31,137 | 18,142 |  | 12,407 | 18,682 |  | 18,917 | 17,782 |
| 35,152 |  |  | 12,657 |  | 19,157 | 25,782 |  |
|  | 35,167 |  | 14,342 |  | 30,162 | 29,907 | 28,372 |
| 35,212 |  |  |  |  |  | 35,172 |  |
|  | 43,192 |  |  |  |  |  | 38,287 |
|  |  |  |  |  |  | 43,132 | 38,347 |
|  |  |  |  |  |  | 45,297 | 43,092 |

FIG. 19

Table 4. Accuracy of Yeast Identifications

| Yeast Species | Accuracy |
|---|---|
| C. Africana | 100.00% |
| C. albicans | 100.00% |
| C. dubliniensis | 100.00% |
| C. glabrata | 99.00% |
| C. orthopsilosis | 96.00% |
| C. parapsilosis | 98.00% |
| C. tropicalis | 100.00% |

FIG. 20

Table 6. Calculation Times in Seconds (replicate executions)

| | | | | | |
|---|---|---|---|---|---|
| Fig. 12 | 0.75 | 0.61 | 0.60 | 0.60 | 0.60 |
| Fig. 13 | 0.87 | 1.00 | 0.88 | 0.93 | 0.91 |
| Fig. 14 | 0.14 | 0.24 | 0.14 | 0.15 | 0.14 |
| Fig. 15B | 0.69 | 0.71 | 0.72 | 0.73 | 0.73 |
| Fig. 15D | 0.57 | 0.55 | 0.54 | 0.56 | 0.54 |

FIG. 22

Table 5. Comparison Between Theoretical and Observed Protein Fragment Ion Masses Obtained During Long Gradient LCMS Analysis of Extract of Yeast *Candida albicans*

| Theoretical Mass (Da) | Observed Mass Da | Mass Diff (Da) | Mass Diff (ppm) | PTMs |
|---|---|---|---|---|
| 6319.27 | 6318.3109 | -0.957115 | -151.483 | |
| 6866.67 | 6866.6553 | -0.0125447 | -1.8269 | |
| 6877.63 | 6877.6356 | 0.00807531 | 1.17414 | |
| 6902.42 | 6902.421 | -0.00104166 | -0.150912 | N-acetyl-L-serine (51) |
| 7560.12 | 7559.1275 | -0.991992 | -131.231 | N-acetyl-L-methionine (49) |
| 8756 | 8756.0032 | 0.00558531 | 0.637884 | |
| 9299 | 9299.0047 | 0.00559834 | 0.602036 | N-acetyl-L-serine (51) |
| 9623.1 | 9623.1064 | 0.00215834 | 0.224287 | N-acetyl-L-serine (51) |
| 9674.95 | 9674.994 | 0.0437783 | 4.5249 | N-acetyl-L-methionine (49) |
| 9763.84 | 9763.8452 | 0.00149531 | 0.153148 | |
| 10324.6 | 10323.6059 | -0.999952 | -96.8607 | N-acetyl-L-serine (51) |
| 10371.4 | 10371.4097 | -0.00571469 | -0.551004 | |
| 11512.6 | 11512.6094 | 0.0417183 | 3.62371 | N-acetyl-L-alanine (41) |
| 12828 | 12828.0273 | 0.0138053 | 1.07618 | |

FIG. 21A

Table 4 (Continued).

| Theoretical Mass (Da) | Observed Mass Da | Mass Diff (Da) | Mass Diff (ppm) | PTMs |
|---|---|---|---|---|
| 12915.7 | 12915.6436 | -0.0166717 | -1.29081 | N-acetyl-L-serine (51) |
| 13227.6 | 13226.6345 | -1.00356 | -75.8743 | N-acetyl-L-serine (51) |
| 13602.6 | 13602.591 | 0.0138753 | 1.02005 | |
| 13726.5 | 13725.5442 | -0.999232 | -72.8009 | N-acetyl-L-serine (51) |
| 13911.7 | 13910.6652 | -0.994662 | -71.5035 | N-acetyl-L-serine (51) |
| 13946.1 | 13946.0658 | 0.00875531 | 0.627798 | |
| 13992.5 | 13992.555 | 0.0281583 | 2.01238 | N-acetyl-L-alanine (41) |
| 14005.5 | 14005.5534 | 0.0313083 | 2.23542 | N-acetyl-L-alanine (41) |
| 14045.9 | 14044.8524 | -1.02216 | -72.7786 | |
| 14283.6 | 14283.6049 | 0.00684531 | 0.479242 | |
| 15414.4 | 15413.4307 | -1.00609 | -65.2737 | N-acetyl-L-serine (51) |
| 15598.6 | 15597.6043 | -0.994765 | -63.7768 | |
| 15797.4 | 15796.4189 | -1.00932 | -63.8958 | |
| 15931.4 | 15930.3562 | -1.00556 | -63.1225 | |
| 16889.9 | 16888.8836 | -1.01815 | -60.2855 | |

FIG. 21B

METHODS FOR DATA-DEPENDENT MASS SPECTROMETRY OF MIXED INTACT PROTEIN ANALYTES

CROSS REFERENCE TO RELATED APPLICATION

This application claims priority to and the benefit of the filing date, under 35 U.S.C. § 119(e), of U.S. Provisional Application for Patent No. 62/132,124, filed on Mar. 12, 2015 and titled "Methods for Data-Dependent Mass Spectrometry of Mixed Biomolecular Analytes", said Provisional application assigned to the assignee of the present invention and incorporated herein by reference in its entirety.

FIELD OF THE INVENTION

The present invention relates to mass spectrometry and, more particularly, relates to methods and systems for automatically discriminating between mass spectral signatures of a plurality of biopolymer molecules, such as peptides and proteins, and, based on the discriminated signatures, controlling operation of a tandem mass spectrometer and performing identification of the biopolymer molecules.

BACKGROUND OF THE INVENTION

Structural elucidation of ionized molecules of complex structure, such as proteins, is often carried out using a tandem mass spectrometer that is coupled to a liquid chromatograph. The general technique of conducting mass spectrometry (MS) analysis of ions generated from compounds separated by liquid chromatography (LC) may be referred to as "LC-MS". If the mass spectrometry analysis is conducted as tandem mass spectrometry (MS/MS), then the above-described procedure may be referred to as "LC-MS/MS". In conventional LC-MS/MS experiments a sample is initially analyzed by mass spectrometry to determine mass-to-charge ratios (m/z) corresponding to the peaks of interest. The sample is then analyzed further by performing product ion MS/MS scans on the selected peak(s). Specifically, in a first stage of analysis, frequently referred to as "$MS^1$", a full-scan mass spectrum, comprising an initial survey scan, is obtained. This full-scan spectrum is the followed by the selection (from the results obtained) of one or more precursor ion species. The precursor ions of the selected species are subjected to ion activation (generally, a deposition of energy) followed by one or more reactions, such as fragmentation, such as may be accomplished employing a collision cell or employing another form of fragmentation cell such as those employing surface-induced dissociation, electron-transfer dissociation or photon dissociation. In a second stage, the resulting fragment (product) ions are detected for further analysis (frequently referred to as either "MS/MS" or "$MS^2$") using either the same or a second mass analyzer. A resulting product spectrum exhibits a set of fragmentation peaks (a fragment set) which, in many instances, may be used as a means to derive structural information relating to the precursor peptide or protein or other biochemical oligomer. It should be noted that, using the fragment ions as a starting population, the process of ion selection and subsequent fragmentation may be repeated yet again, thereby yielding an "$MS^3$" spectrum. In the general case, a mass spectrum obtained after (n−1) iterated stages of selection and fragmentation may be referred to as an "$MS^n$" spectrum. This is a time-consuming process because the sample needs to be mass analyzed at least twice and the MS/MS data is only recorded for a limited number of components.

Most presently available mass spectrometers capable of tandem analysis are equipped with an automatic data-dependent function whereby, when selecting the precursor ion for $MS^2$ analysis from the ion peaks in $MS^1$, the ion precursors are selected in decreasing intensities. In a simple data-dependent experiment shown in FIG. 1A, a detector continuously measures total current attributable to ions entering a mass spectrometer detector. A threshold intensity level 8 of the total ion current is set below which only $MS^1$ data is acquired. As a first component—detected as peak 10—elutes, the total ion current intensity crosses the threshold 8 at time t1. When this occurs, an on-board processor or other controller of the mass spectrometer determines the most intense ion in the $MS^1$ spectra and immediately initiates an MS/MS scan with regard to the most intense ion. Subsequently, the leading edge of another elution peak 12 is detected. When the total ion current once again breaches the threshold intensity 8 at time t3, an MS/MS scan is initiated with regard to the most intense ion detected after time t3. Generally, the peak 12 will correspond to the elution of a different chemical component and, thus, the most abundant ion detected after time t3 will be different from the ion for which MS/MS analysis was conducted during the elution peak 10. In this way, both MS and MS/MS spectra are acquired on each component as it elutes.

The simple data dependent experiment described above works well with chromatographically resolved or partially resolved components, as are illustrated in FIG. 1A. However, in a very complex mixture there may be components whose elution peaks completely overlap, as illustrated in the graph of ion current intensity versus retention time in FIG. 1B. In this example elution peak 11 represents the ion current attributable to ion m11, and elution peak 13 represents the ion current attributable to ion m13, the masses of these ions being schematically illustrated in the mass spectrum representation in inset box 16. In the hypothetical situation shown in FIG. 1B, there is almost perfect overlap of the elution of the compounds that give rise to ions m11 and m13, with the mass spectral intensity of ion m11 always being greater than that of ion m13 during the course of the elution. Under these conditions, the simple data-dependent technique discussed above with reference to FIG. 1A will fail to ever initiate MS/MS analysis of ion m13 (and possibly other important ions), since only the most intense component (m11) will be selected for MS/MS.

The hypothetical two-ion situation illustrated in FIG. 1B is a simplified example. Most modern mass spectrometer instruments are capable of performing a series of MS/MS analyses with regard to each respective one of several abundant ions detected in an MS 1 analysis. Typically, instead of choosing just a single most-abundant precursor, modern instruments will select the "top P number of the most abundant precursors" for tandem mass analysis based on the information of a preceding $MS^1$ data acquisition, where the number P is either a constant or perhaps a variable input by a user. Nonetheless, the basic issue demonstrated by FIG. 1B remains, especially for multicomponent samples of biopolymer analytes which may give rise to tens to hundreds of mass spectral peaks in a single mass spectrum. Regardless of how such a sample is introduced into a mass spectrometer (for example, by chromatographic separation, flow injection, or capillary electrophoresis; as a chemical separate delivered from a lab-on-a-chip device, by infusion or other method), more than one analyte may be represented in a single mass spectrum from a single time point, and each such analyte may give rise to many ions, as illustrated in hypothetical mass spectrum illustrated in FIG. 1C. In FIG. 1C, solid vertical lines outlined by envelope 208 represent centroids of a first set of mass spectral peaks generated from a first analyte compound and dotted vertical lines outlined by envelope 206 represent centroids of a second set of mass spectral peaks generated from a second co-eluting analyte compound. It is evident that, even if the number, P, of most-abundant peaks to be analyzed is equal to 10, for example, than only the ions of only one of the analyte compounds will be selected for MS/MS analysis using the traditional data dependent methods described above. Information relating to the second analyte will be lost. Further, the data so obtained will comprise redundant information on the same component.

To more successfully address the complexities of mass spectral analysis of co-eluting compounds, many mass spectral instruments also employ the so-called "Dynamic Exclusion" principle by which a mass-to-charge ratio is temporarily put into an exclusion list after its $MS^n$ spectrum is acquired. The excluded mass-to-charge ratio is not analyzed by $MS^n$ again until a certain time duration has elapsed after the prior $MS^n$ spectrum acquisition. This technique minimizes a chance of fragmenting the same precursor ion in several subsequent scans, and allows a mass spectrometer to collect $MS^n$ spectra on other components having less intense peaks which would otherwise not be examined. After a selected period of time the excluded ion will be removed from the list so that any other compounds with the same mass-to-charge ratio can be analyzed. This time duration during which the ion species is on the exclusion list is generally estimated based on an average or estimated chromatographic peak width. Thus, use of the Dynamic Exclusion principle allows more data to be obtained on more components in complex mixtures.

Unfortunately, existing dynamic exclusion techniques may perform poorly for analyzing mass spectra of mixtures of complex biomolecules. For example, consider once again the hypothetical situation illustrated in FIG. 1C. If the ions depicted in FIG. 1C are analyzed using the dynamic exclusion principle, then at least 10 ion species derived from a single analyte (outlined by envelope 208) will be analyzed, in decreasing order of their intensities in the illustrated $MS^1$ spectrum, by $MS^n$ analysis prior to any peaks from the less abundant analyte (outlined by envelope 206) being considered. This sequence will occur regardless of the fact that each precursor each ions species is placed onto an exclusion list after its respective analysis. The amount of time consumed performing ten unnecessarily redundant $MS^n$ analyses may then lead to expiration of the exclusion time of the most abundant ion (or may lead to exhaustion of the time available to fully analyze a small number of most abundant ions), after which the entire sequence may of $MS^n$ analyses may be repeated.

A further complicating factor in the application of the dynamic exclusion principle to mass analysis of mixtures of complex biomolecules derives from the fact that the elution profiles of the various compounds are highly variable and difficult to predict. Different biopolymer compounds may exhibit different elution profiles as a result of complex interactions between a chromatographic stationary phase and a biopolymer with multiple molecular interaction sites. Moreover, the time profiles of various ions generated from even a single such compound may fail to correlate with the elution profile of the un-ionized compound or with the profiles of one another as a result of ionization suppression within an ionization source of a mass spectrometer.

As an example of the elution profile variability that may be encountered, FIG. 2 illustrates a set of chromatograms collected from a single liquid chromatography-mass spectrometry experimental run of an *E. Coli* extract. Total ion current is shown in the topmost chromatogram (curve 40) and various extracted ion chromatograms, illustrating the ion current that is contributed by respective m/z-ratio ranges are shown in the lowermost five plots (curves 50, 60, 70, 80 and 90). Curve 50 represents the m/z range 660.0-660.5 Da. Similarly, curves 60, 70, 80 and 90 represent m/z ranges 700.5-701.5 Da, 1114.5-1114.5 Da, 942.5-943.5 Da and 540.5-540.5 Da. Peaks 1, 2 and 3 are examples of peaks with broad chromatographic profiles. Peaks 4 and 5 are examples of narrow profiles. Peak 6 shows an extremely broad peak. The peak widths span over an order of magnitude, therefore severely limiting the applicability of an exclusion list having a pre-defined exclusion time duration.

The existing data dependent and dynamic exclusion workflow techniques and corresponding algorithms were developed for small molecules, small peptides and other analytes which acquire a limited number of charges (for example, 1-3 charges) in the electrospray ionization process. When applied to higher-molecular-weight biopolymer analytes (most commonly, intact proteins during the course of so-called "top-down" proteomics studies) these conventional methodologies significantly under-perform due to a combination of different electrospray behavior and computational limitations. More specifically: (1) intact high mass analytes in general, and proteins in particular, develop many more charge states (up to 50 charges or more per molecule, e.g., FIG. 1C) than do small molecules during the electrospray ionization process because of a greater number of charge acquiring sites which results in much more complex MS spectra; (2) in complex mixtures such as cell lysates or their fractions, there is a wide distribution of molecular weights and copy numbers which results in a very complex overlap of charge state distribution patterns of varying intensities; (3) variability in physiochemical properties of the high-mass analytes of the same or different chemical nature results in significant variability of chromatographic peak shapes and analyte retention on the column; (4) if the mass spectra are acquired on a mass spectrometer with high resolving power such as an Orbitrap™ mass analyzer (a type of electrostatic trap mass analyzer) or a time-of-flight (TOF) mass analyzer, corresponding peaks further resolve into a number of isotopes in a series of clusters whose quality is often far from a theoretical binomial distribution; (5) matrix ionization effects of a variety of different proteins can greatly influence the observed intensity of multiply overlapping species so as to distort the true ratios of protein intensities found in any given standard or sample. These factors make it difficult to estimate a time for placing analyte-specific m/z values on a dynamic exclusion list. Additional levels of complexity are introduced by oxidized species of the same analyte or adducts, overlaps of isotope clusters and inability of existing software tools correctly calculate charge state for high mass species.

It is not uncommon for a single protein to generate greater than hundreds of resolved peaks (including both charge states and isotopes) per MS mass spectrum on high resolution/mass accuracy instruments. In practical terms, the above considerations imply that, in the case of intact proteins and other biopolymers, existing data dependent algorithms are being confounded and MS/MS is being performed in a redundant fashion on a number of different charge states from the same biopolymer. Also, when isotopic clusters do not match the traditional binomial distribution patterns defined by the number of carbon, hydrogen, nitrogen, oxygen, nitrogen and sulfur atoms present in a given biopolymer, or do not meet intensity threshold or signal-to-noise requirements, redundancy occurs from fragmenting multiple isotopes which belong to the same isotopic cluster. This duplication of work leads to redundancy in identification of the most abundant/ionizable proteins, while the information about other species is lost and provides very little opportunity for triggering an $MS^n$ analysis.

There is thus a need in the art of mass spectrometry of biomolecules for improved methods of analysis that can efficiently differentiate signal from noise, correctly allocate related m/z values into proper isotopic clusters, correctly determine charge states and properly organize the various charge states into distribution envelopes. Such improvements are required for success in both data acquisition and post acquisition processing workflows.

Preferably, the improved methods and algorithms should be able to work in a "real-time" environment such that automated data-dependent decisions may be made while mass spectra are being acquired. Such methods and algorithms should be able to not only extract as much information from each mass spectrum as possible, but also to direct subsequent $MS^n$ analysis in a desired way based on the information gathered in a preceding mass spectrum. The present disclosure addresses these needs.

SUMMARY

The current invention eliminates the above described limitations and enables both effective (1) non-redundant data dependent mass spectrometry analysis and (2) post-acquisition data processing for individual high mass analytes and their mixtures of different complexities. For data dependent mass spectrometry analysis, the herein-described novel "Top P Unique Analyte-Specific Clusters" workflow and associated computation replaces the previous state-of-the-art "Top P Most Abundant Precursors" logic. Each such species-correlative envelope is a set of related mass spectral lines (m/z values) which are indicated, according to the methods of the present teachings, to all be generated from a single unique molecule. Each species-correlative envelope groups together various charge states and isotopic clusters that are indicated to have been produced from a single molecule. However, the species-correlative envelope can exclude adducts if desired, which are removed prior to data analysis.

Tandem mass spectrometry (or, more-generally, $MS^n$ analysis) is performed only on selected representatives of a given species-correlative charge state distribution envelope after which data acquisition is directed to the next species-correlative charge state distribution envelope (i.e., of a different compound) that is determined in a preceding MS spectrum, and so on. Prior to $MS^n$ analysis, computed charge state distribution patterns are filtered so as to exclude oxidized (or other specified) species of the same analyte and various other unwanted adducts. In this approach, the most possible abundant information on the analytes in a sample is retrieved either on a chromatographic time scale, or in experiments in which sample is introduced into a mass spectrometer by infusion, flow injection or by means of any other sample introduction device. In all cases, data-acquisition redundancy is either totally eliminated or significantly reduced.

The "Top P Unique Analyte-Specific Clusters" workflow may include one or more of (1) correct computational assignment of charge state to each peak (centroid) in isotopic clusters found in a scan; (2) the use of information on charge state to assign isotopic clusters (either resolved or unresolved) to the appropriate charge-state envelope(s); (3) optional determination of molecular weights; and (4) the control of data-dependent acquisition in a way to allow only one (or a selected number) of $MS^n$ event(s) per each individual charge state envelope. The "Top P Unique Cluster" method can be set up to work with the most intense charge state for a given biopolymer, the median charge state between the highest charge state detected and the most intense charge state observed, or any other desired charge state. The method is therefore well-suited for use with a variety of ion activation methods including but not limited to collision-induced dissociation (CID) and electron-transfer dissociation (ETD), defined for a given molecular weight range, or in instances in which the least abundant proteins species are interrogated first. Similar methods may be employed for post-acquisition data processing, in which the same computation logic is applied to raw MS spectra for which acquisition is completed prior to execution of the novel methods. Post-acquisition data processing may further include molecular weight determination and analyte identification.

These principles of the present teachings can be applied for analytes of various molecular weights and chemical nature on high resolution tandem mass spectrometry systems including but not limited to mass spectrometer instruments that are based on or include an Orbitrap™ mass analyzer. Such instruments include Orbitrap Fusion™, Orbitrap Velos-Pro™, Q-Exactive™, and Orbitrap Elite™ as well as quadrupole time-of-flight (QTOF) mass spectrometers and Fourier transform ion cyclotron resonance (FT-ICR) mass spectrometers. Further, the same principles can be applied to isotopically unresolved charge state envelopes which can be seen in mass spectra obtained on high resolution mass spectrometry systems for comparatively very high mass analytes, or to unit resolution mass spectra obtained on mass analyzers such as linear ion traps or any other Paul trap configuration. In instances, instead of making charge determinations based on a distance between individually resolved lines of isotopic clusters, these are instead calculated using distances between charge states within the same charge state envelope. Again, this clustering based strategy can be applied to unit resolution data as well as to data generated by linear ion traps and triple quadrupole instrumentation.

When used in conjunction with chromatographic separation, the proposed workflow methods maximize information from each individual mass spectrum obtained during the course of a chromatographic run. The novel methods may also be employed in conjunction with mass spectral experiments in which sample is introduced by infusion or flow injection. In most experimental situations, the novel methods significantly reduce total analysis time. When applied to data already acquired, the novel "Top P Unique Analyte-Specific Clusters" workflow methods can maximize the information yield from MS spectra and can calculate the molecular weights of the analytes in real time.

The novel principles, workflows and algorithms and methods described and taught in this disclosure are applicable in all cases when several analytes are mass spectrometrically (MS) detectable within the same mass spectrum. For example, the novel teachings may be employed in cases in which two or more analytes co-elute from a chromatographic column and the co-eluting analytes are simultaneously introduced into a mass spectrometer. As a second example, the novel teachings may be employed in cases in which two or more analytes are introduced into a mass spectrometer using a flow injection methodology. In yet a third example, the novel teachings may be employed in cases in which two or more analytes are introduced into a mass spectrometer using syringe infusion. In still yet other examples, the novel teachings may be employed in cases in which analytes are introduced into a mass spectrometer after separation by a capillary electrophoresis apparatus or a lab-on-a-chip apparatus. The novel methods may be employed in conjunction with mass spectrometers employing any known ionization technique, such as, without limitation, photo-ionization, thermospray ionization, electrospray ionization (ESI), desorption electrospray ionization (DESI), paper spray ionization, atmospheric pressure chemical ionization (APCI) and matrix-assisted laser desorption ionization (MALDI).

BRIEF DESCRIPTION OF THE DRAWINGS

To further clarify the above and other advantages and features of the present disclosure, a more particular description of the disclosure will be rendered by reference to specific embodiments thereof, which are illustrated in the appended drawings. It is appreciated that these drawings depict only illustrated embodiments of the disclosure and are therefore not to be considered limiting of its scope. Accordingly, the disclosure will be described and explained with additional specificity and detail through the use of the accompanying drawings, not necessarily drawn to scale, in which:

FIG. 2 is a set of chromatograms collected from a single liquid chromatography-mass spectrometry experimental run of an *E. Coli* extract, including a total ion current chromatogram (top curve) and also illustrating various extracted ion chromatograms (lower curves) that contribute to the total ion current, each extracted ion chromatograph representing a respective m/z ratio range;

FIG. 6 is a flowchart of a method in accordance with the present teachings for constructing a Boolean occupancy array within a mathematically transformed mass-to-charge space from experimentally determined mass spectral centroid data;

FIG. 10A and continuations on FIGS. 10B, 10C and 10D, is a table showing typical molecular weights, expected number of $C^{13}$ atoms in the most abundant isotope (mode), expected average number of $C^{13}$ atoms among all isotopes and the difference between the expected average number and the mode, as they vary with the total number of $C^{12}$ atoms in a protein;

FIGS. 11A, 11B, 11C and 11D are depictions of computer screen user interfaces which may be employed in conjunction with user control of and information display from computer software that employs methods in accordance with the present teachings;

FIG. 16 is a table of the accuracy of molecular weights, as calculated in accordance with the presently taught methods, of five standard proteins;

FIG. 18A is a plot of a first portion of calculated molecular weights, as calculated in accordance with the presently taught methods, of mass analyzed proteins from a lysate of the bacterium *E. Coli* after treatment of the lysate with a proton transfer reagent;

FIG. 18B is a plot of a second portion of the calculated molecular weights of the sample of FIG. 18A;

FIG. 19 is a table of molecular weights of proteins that are diagnostic for distinguishing between closely related bacterial species, as determined by mass spectrometric analyses used in conjunction with methods in accordance with the present teachings;

FIG. 20 is a table of the accuracy of identifications of various yeast species, using mass spectrometric analyses in conjunction with methods in accordance with the present teachings;

FIGS. 21A and 21B are a table illustrating a comparison between theoretical and observed protein fragment ion masses obtained during long gradient LCMS analysis of an extract of the yeast *Candida albicans*; and FIG. 22 is a table of times required for calculating the mass spectrometry deconvolution results that are shown in various of the accompanying figures.

DETAILED DESCRIPTION

The present disclosure describes various improved and novel methods for data-dependent mass spectrometry of biopolymer molecules as well as novel methods for analyzing and interpreting mass spectra of biopolymer molecules. The following description is presented to enable any person skilled in the art to make and use the invention, and is provided in the context of a particular application and its requirements. Various modifications to the described embodiments will be readily apparent to those skilled in the art and the generic principles herein may be applied to other embodiments. Thus, the present invention is not intended to be limited to the embodiments and examples shown but is to be accorded the widest possible scope in accordance with the features and principles shown and described.

1. Mass Spectrometer Hardware Examples

Figure 1A:
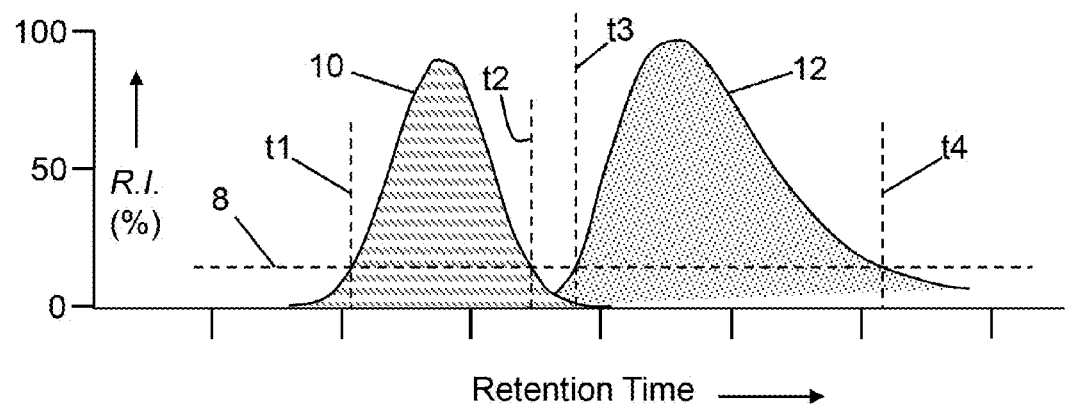
FIG. 1A is a schematic illustration of simple intensity-threshold-based data dependent mass spectral analysis of two analytes exhibiting well-resolved chromatographic peaks.
Figure 1B:
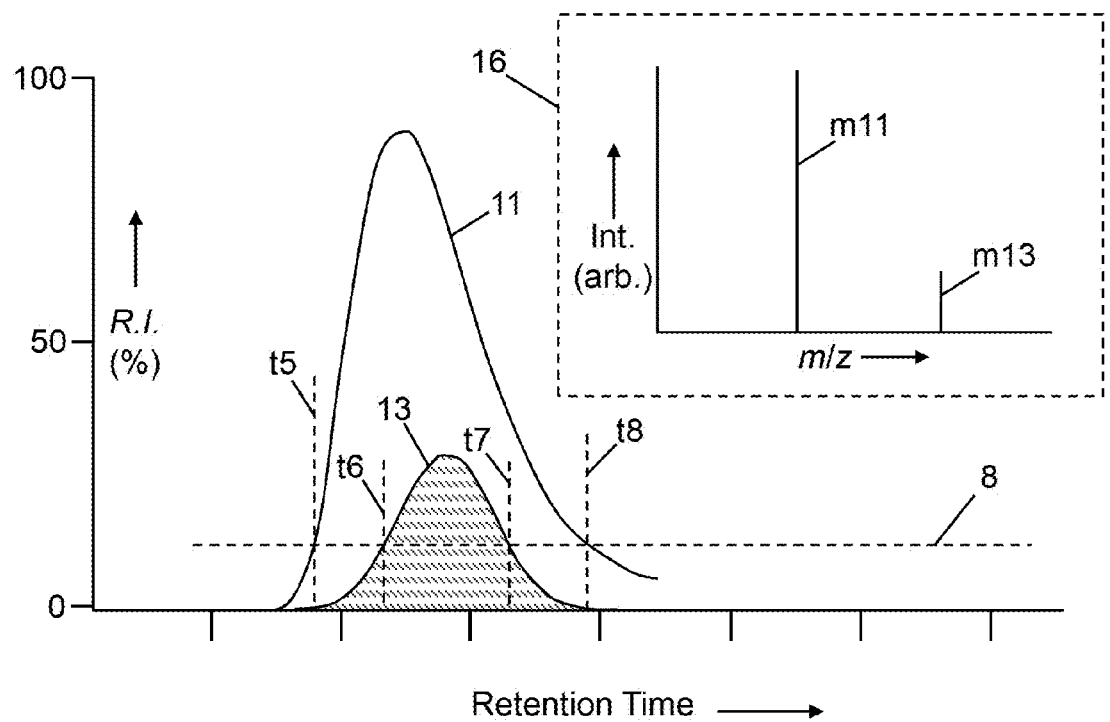
FIG. 1B is a schematic illustration of a portion of a chromatogram with highly overlapping elution peaks, both of which are above an analytical threshold.
Figure 1C:
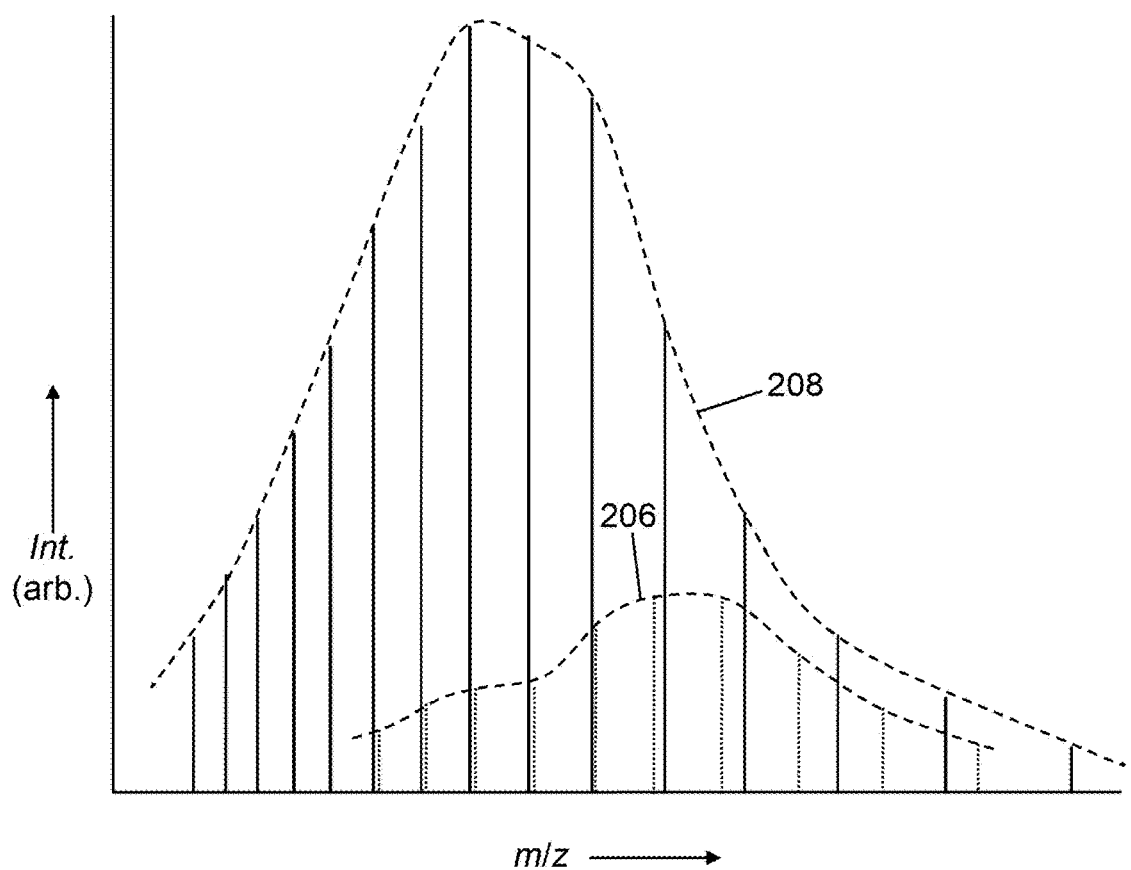
FIG. 1C is an illustration of multiple interleaved mass spectral peaks of two simultaneously eluting biopolymer analytes.
Figure 3A:
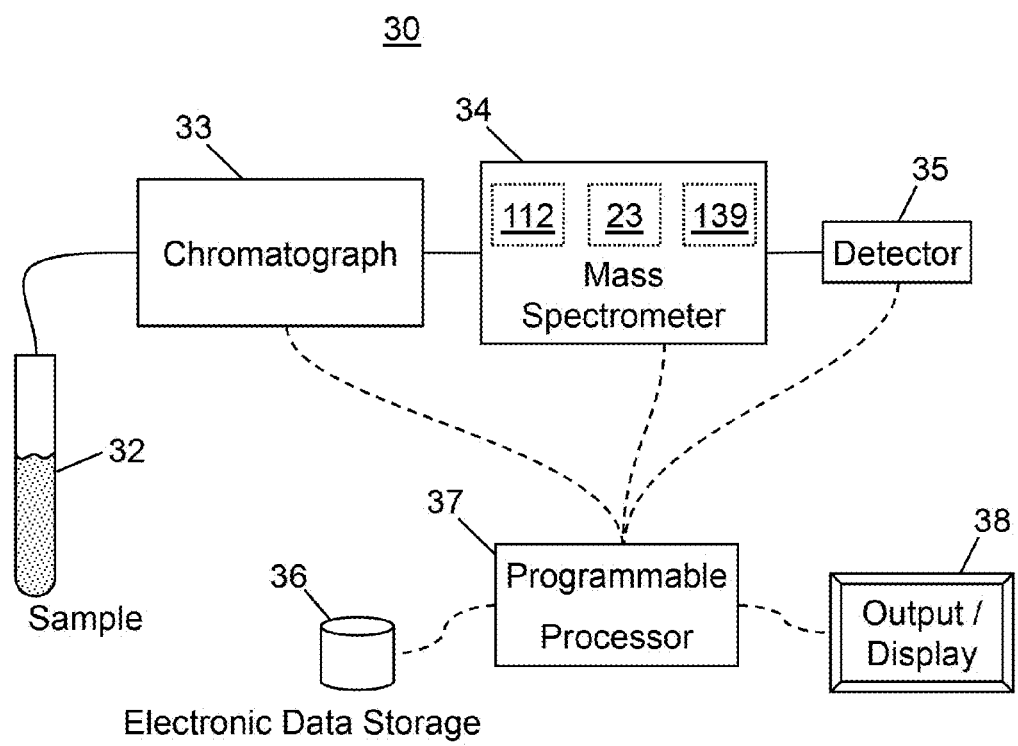
FIG. 3A is a schematic diagram of a system for generating and automatically analyzing chromatography/mass spectrometry spectra in accordance with the present teachings.

FIG. 3A is a schematic example of a general for generating and automatically analyzing chromatography/mass spectrometry spectra as may be employed in conjunction with the methods of the present teachings. A chromatograph 33, such as a liquid chromatograph, high-performance liquid chromatograph or ultra high performance liquid chromatograph receives a sample 32 of an analyte mixture and at least partially separates the analyte mixture into individual chemical components, in accordance with well-known chromatographic principles. The resulting at least partially separated chemical components are transferred to a mass spectrometer 34 at different respective times for mass analysis. As each chemical component is received by the mass spectrometer, it is ionized by an ionization source 112 of the mass spectrometer. The ionization source may produce a plurality of ions comprising a plurality of ion species (i.e., a plurality of precursor ion species) comprising differing charges or masses from each chemical component. Thus, a plurality of ion species of differing respective mass-to-charge ratios may be produced for each chemical component, each such component eluting from the chromatograph at its own characteristic time. These various ion species are analyzed—generally by spatial or temporal separation—by a mass analyzer 139 of the mass spectrometer and detected by a detector 35. As a result of this process, the ion species may be appropriately identified according to their various mass-to-charge (m/z) ratios. As illustrated in FIG. 3A, the mass spectrometer comprises a reaction cell 23 to fragment or cause other reactions of the precursor ions, thereby generating a plurality of product ions comprising a plurality of product ion species.

Still referring to FIG. 3A, a programmable processor 37 is electronically coupled to the detector of the mass spectrometer and receives the data produced by the detector during chromatographic/mass spectrometric analysis of the sample(s). The programmable processor may comprise a separate stand-alone computer or may simply comprise a circuit board or any other programmable logic device operated by either firmware or software. Optionally, the programmable processor may also be electronically coupled to the chromatograph and/or the mass spectrometer in order to transmit electronic control signals to one or the other of these instruments so as to control their operation. The nature of such control signals may possibly be determined in response to the data transmitted from the detector to the programmable processor or to the analysis of that data as performed by a method in accordance with the present teachings. The programmable processor may also be electronically coupled to a display or other output 38, for direct output of data or data analysis results to a user, or to electronic data storage 36. The programmable processor shown in FIG. 3A is generally operable to: receive a precursor ion chromatography/mass spectrometry spectrum and a product ion chromatography/mass spectrometry spectrum from the chromatography/mass spectrometry apparatus and to automatically perform the various instrument control, data analysis, data retrieval and data storage operations in accordance with the various methods discussed below.

Figure 3B:
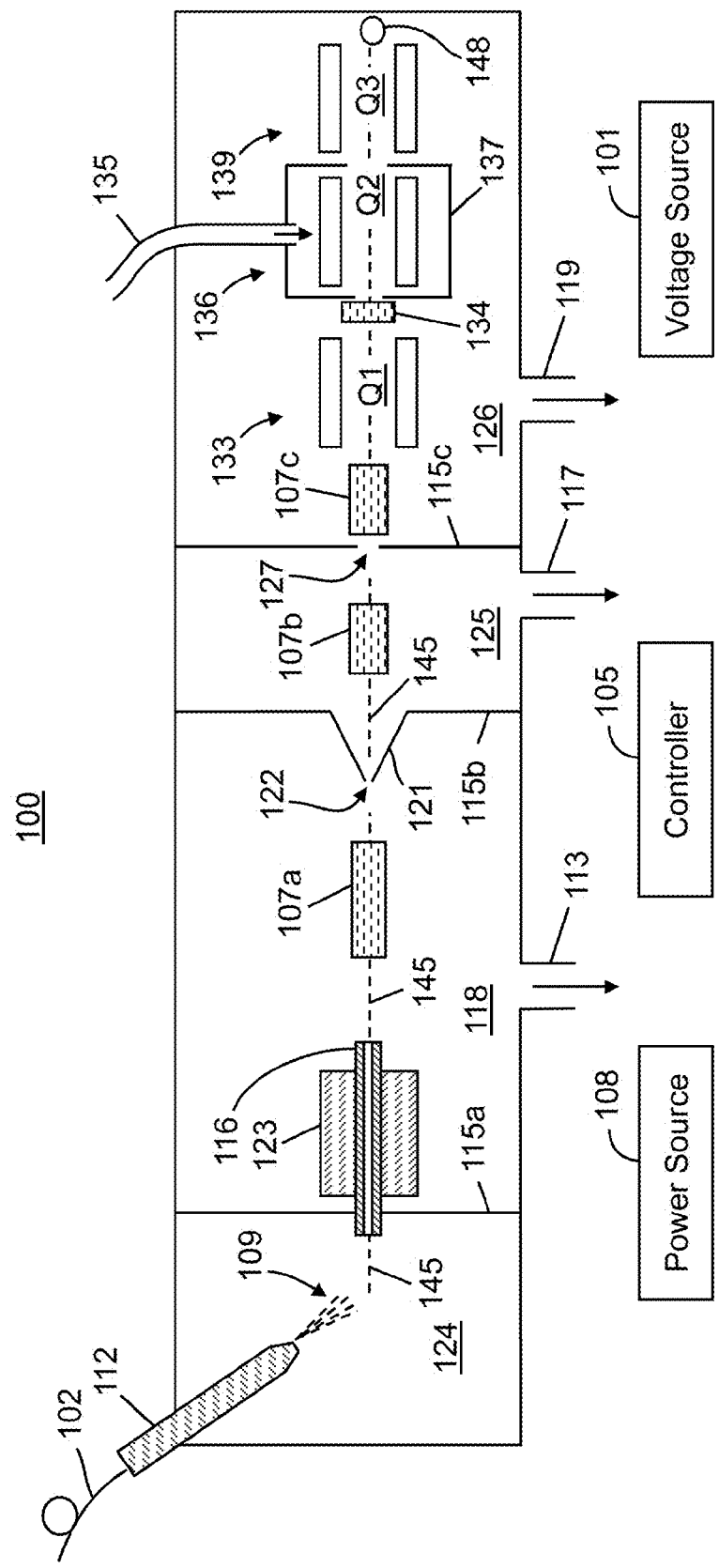
FIG. 3B is a schematic illustration of an example of a conventional triple quadrupole mass spectrometer in which $MS^n$ mass spectrometry may be performed.

FIG. 3B is a schematic illustration of an example of a conventional triple quadrupole mass spectrometer system, shown generally at 100, generally capable of performing $MS^1$ or $MS^2$ analysis. Referring to FIG. 3B, an ion source 112 housed in an ionization chamber 124 is connected to receive a liquid or gaseous sample from an associated apparatus such as for instance a liquid chromatograph or syringe pump through a capillary 102. As but one example, an atmospheric pressure electrospray source is illustrated. However, any ion source may be employed, such as a heated electrospray ionization (H-ESI) source, an atmospheric pressure chemical ionization (APCI) source, an atmospheric pressure matrix assisted laser desorption (MALDI) source, a photoionization source, a desorption ionization (DESI) source, a paper spray ion source or a source employing any other ionization technique or a combination of the above techniques. The ion source 112 forms charged particles 109 (either ions or charged droplets that may be desolvated so as to release ions) representative of the sample. The charged particles 109 are subsequently transported from the ion source 112 to the mass analyzer 139 in high-vacuum chamber 126 through intermediate-vacuum chambers 118 and 125 of successively lower pressure in the direction of ion travel. In particular, the droplets or ions are entrained in a background gas and may be transported from the ion source 112 through an ion transfer tube 116 that passes through a first partition element or wall 115a into an intermediate-vacuum chamber 118 which is maintained at a lower pressure than the pressure of the ionization chamber 124 but at a higher pressure than the pressure of the high-vacuum chamber 126. The ion transfer tube 116 may be physically coupled to a heating element or block 123 that provides heat to the gas and entrained particles in the ion transfer tube so as to aid in desolvation of charged droplets so as to thereby release free ions.

Due to the differences in pressure between the ionization chamber 124 and the intermediate-vacuum chamber 118 (FIG. 3B), gases and entrained ions are caused to flow through ion transfer tube 116 into the intermediate-vacuum chamber 118. A second partition element or wall 115b separates the intermediate-vacuum chamber 118 from a second intermediate-pressure region 125, likewise a third partition element or wall 115c separates the second intermediate pressure region 125 from the high-vacuum chamber 126. A first ion optical assembly 107a provides an electric field that guides and focuses the ion stream leaving ion transfer tube 116 through an aperture 122 in the second partition element or wall 115b that may be an aperture of a skimmer 121. A second ion optical assembly 107b may be provided so as to transfer or guide ions to an aperture 127 in the third partition element or wall 115c and, similarly, another ion optical assembly 107c may be provided in the high vacuum chamber 126 containing a mass analyzer 139. The ion optical assemblies or lenses 107a-107c may comprise transfer elements, such as, for instance a multipole ion guide and/or one or more ion lenses, so as to direct the ions through aperture 122 and into the mass analyzer 139. The mass analyzer 139 comprises one or more detectors 148 whose output can be displayed as a mass spectrum. Vacuum ports 113, 117 and 119 may be used for evacuation of the various vacuum chambers.

The mass spectrometer system 100 (as well as other such systems illustrated herein) is in electronic communication with a controller 105 which includes hardware and/or software logic for performing data analysis and control functions. Such controller may be implemented in any suitable form, such as one or a combination of specialized or general purpose processors, field-programmable gate arrays, and application-specific circuitry. In operation, the controller effects desired functions of the mass spectrometer system (e.g., analytical scans, isolation, and dissociation) by adjusting voltages (for instance, RF, DC and AC voltages) applied to the various electrodes of ion optical assemblies 107a-107c and quadrupoles or mass analyzers 133, 136 and 139, and also receives and processes signals from detector 148. The controller 105 may be additionally configured to store and run data-dependent methods in which output actions are selected and executed in real time based on the application of input criteria to the acquired mass spectral data. The data-dependent methods, as well as the other control and data analysis functions, will typically be encoded in software or firmware instructions executed by controller. A power source 108 supplies an RF voltage to electrodes of the devices and a voltage source 101 is configured to supply DC voltages to predetermined devices.

As illustrated in FIG. 3B, the conventional mass spectrometer system 100 is a triple-quadrupole system comprising a first quadrupole device 133, a second quadrupole device 136 and a third quadrupole device 139, the last of which is a mass analyzer comprising one or more ion detectors 148. The first, second and third quadrupole devices may be denoted as, using common terminology, as Q1, Q2 and Q3, respectively. A lens stack 134 disposed at the ion entrance to the second quadrupole device 136 may be used to provide a first voltage point along the ions' path. The lens stack 134 may be used in conjunction with ion optical elements along the path after stack 134 to impart additional kinetic energy to the ions. The additional kinetic energy is utilized in order to effect collisions between ions and neutral gas molecules within the second quadrupole device 136 thereby generating product ions. If collisions are desired, the voltage of all ion optical elements (not shown) after lens stack 134 are lowered (assuming positively charged ions) relative to lens stack 134 so as to provide a potential energy difference which imparts the necessary kinetic energy.

Conventional triple-quadrupole systems, such as the system 100 depicted in FIG. 3B, may generally only be operated so as to provide one stage of ion fragmentation (thereby, in such operation, performing an $MS^2$-type experiment). Under special operation, they can be configured to perform, at most, one additional stage of ion fragmentation in the vicinity of an aperture 122 of a skimmer 121. This type of operation requires proper configuration of the electrical potential applied to the skimmer and to an electrode upstream from the skimmer. Although this approach can yield a form $MS^3$ operation, it does not allow for initial selection of a precursor ion but, instead, causes fragmentation of all ion species as they cross the skimmer interface.

Figure 3C:
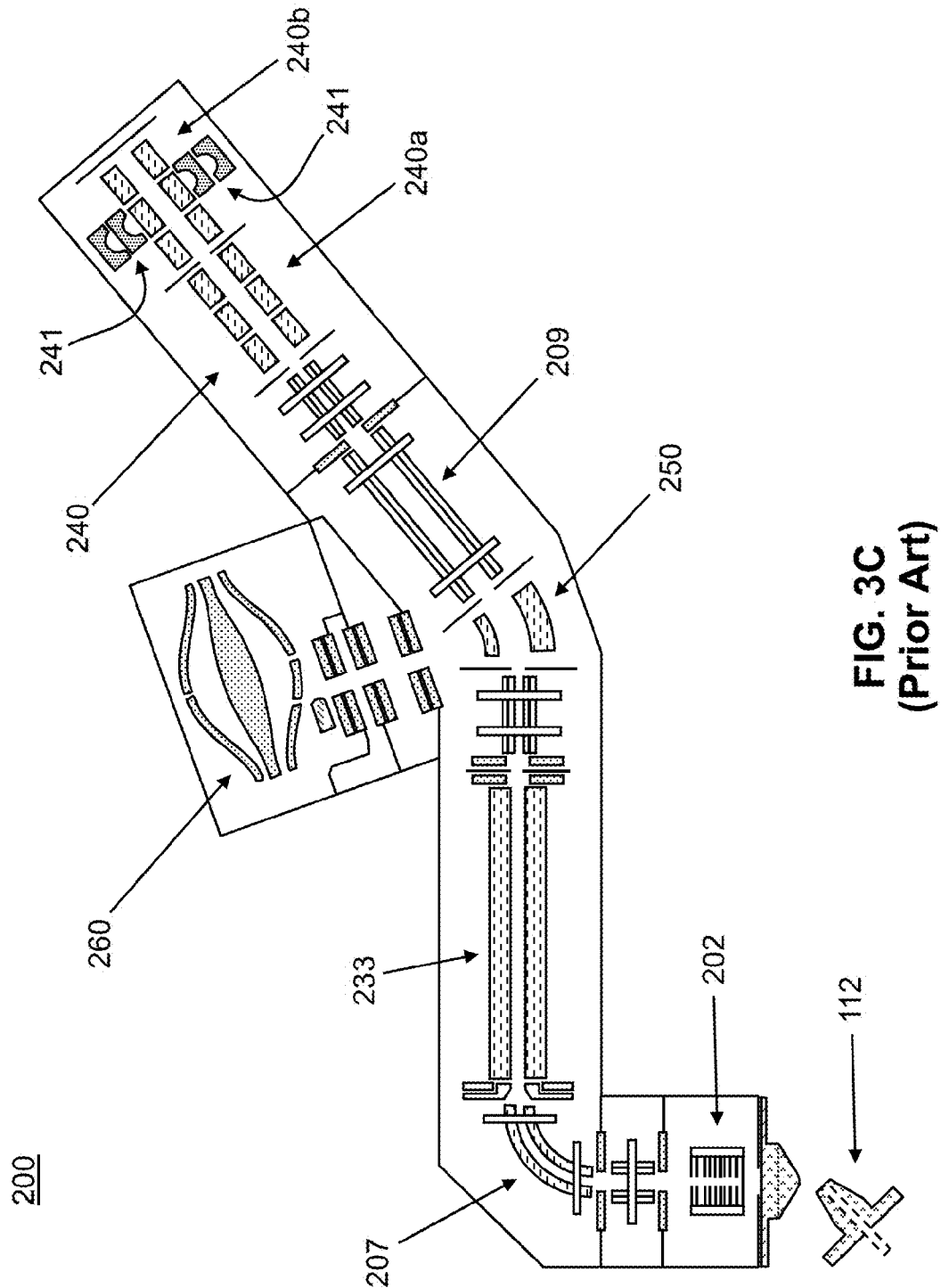
FIG. 3C is a schematic illustration of a known multi-component, multi-analyzer mass spectrometer in which $MS^n$ mass spectrometry may be performed.

Other types of mass spectrometer systems can provide capability to perform general $MS^n$ experiments and the flexibility to adapt such experiments to particular samples or conditions. FIG. 3C schematically illustrates one such system, which is marketed and sold under the Thermo Scientific™ Orbitrap Fusion™ mass spectrometer name by Thermo Fisher Scientific of Waltham, Mass. USA. The system 200 illustrated in FIG. 3C is a composite system comprising multiple mass analyzers including: (a) a dual-pressure linear ion trap analyzer 240 and (b) an Orbitrap™ mass analyzer (a type of electrostatic trap analyzer) 260. A key performance characteristic of this instrument is its high duty cycle, which is realized by efficient scan scheduling, so that master scans are acquired with one analyzer while data-dependent $MS^n$ scans are acquired with the other analyzer. In addition to the two mass analyzers, the system 200 further includes a quadrupole mass filter 233 which may be employed for precursor ion selection, a C-trap ion trap 250 which is operational to route ions into the Orbitrap™ mass analyzer and an ion-routing multipole ion guide 209 which may be configured to either store ions or fragment ions by collision-induced dissociation (CID) and is capable of routing ions in the direction of either the C-trap ion trap 250 or the dual-pressure linear ion trap analyzer 240.

The dual-pressure linear ion trap analyzer 240 comprises a high-pressure cell portion 240a and a low-pressure cell portion 240b. The high-pressure cell portion 240a may be infused with either an inert gas for purposes of enabling ion fragmentation by collision-induced dissociation or with a reagent gas for purposes of enabling ion fragmentation by electron transfer dissociation (ETD). The low-pressure cell portion 240b is maintained under high vacuum and includes ion detectors 241 for operation as a linear ion trap mass analyzer. Thus, the system 200 provides ion fragmentation capability in either the multipole ion guide 209 or in the high-pressure cell portion 240a of the dual-pressure linear ion trap analyzer 240. The system may be operated so as to perform multiple successive stages of ion fragmentation—that is, (n−1) stages of fragmentation for $MS^n$ analysis—of ions derived from an initially introduced batch of ions by shuttling the ions or the derived ions between the multipole ion guide 209 and the high-pressure cell portion.

In operation of the system 200, ions introduced from ion source 112 are efficiently guided and focused into an evacuated chamber by stacked ring ion guide 202. A bent active beam guide 207 causes ions to change their trajectory whereas neutral molecules follow a straight-line trajectory which enables them to be vented by the vacuum system (not illustrated). The ions then pass into the quadrupole mass filter which may be operated, in known fashion, such that only ions comprising a certain pre-determined ink range or ranges pass through in the direction of the C-trap 250. From the C-trap, ions may be directed into the Orbitrap mass analyzer for high-accuracy mass analysis or may be caused to pass into the multipole ion guide 209 or the ion trap analyzer 240 for either fragmentation, mass analysis or both. After fragmentation, product ions may be routed back to the C-trap 250 for subsequent injection into the Orbitrap mass analyzer for high-accuracy mass analysis.

Invention embodiments in accordance with the present teachings may be used in conjunction with operation of any of the above-described mass spectrometer systems as well as others that are not specifically shown. For example, the invention described herein has been successfully run in conjunction with operation of a Q-Exactive™ mass spectrometer system, which lacks the dual-pressure linear ion trap analyzer 240 and associated detectors 241 shown in FIG. 3C and instead includes a higher-energy collisional dissociation cell (HCD cell) in the general position to the right-hand-side (as illustrated in FIG. 3C) of the C-trap 250. Thus, the a Q-Exactive™ mass spectrometer system essentially combines precursor-ion selection by a high-performance quadrupole mass filter with high-resolution mass analysis and detection by an Orbitrap™ mass analyzer. During operation, the HCD cell is used for fragmentation or storage of ions for subsequent analysis by the Orbitrap analyzer.

2. Computational Methods

As biological samples are generally very complex, a single MS spectrum can easily contain hundreds to even thousands of peaks which belong to different analytes—all interwoven over a given m/z range in which the ion signals of very different intensities overlap and suppress one other. The resulting computational challenge is to trace each peak back to a certain analyte(s). The elimination of "noise" and determination of correct charge assignments are the first step in tackling this challenge. Once the charge of a peak is determined, then one can further use known relationships between the charge states in a charge state envelope to group analyte related charge states. This information can be further used to determine molecular weight of analyte(s) in a process which is best described as mathematical decomposition (also referred to, in the art, as mathematical deconvolution).

Obviously, the computations are much more challenging in real time during an automatic top-down data dependent analysis since this should occur very fast, especially when chromatographic separation is involved. To succeed, one needs to have a data acquisition strategy that anticipates multiple mass spectral lines for each ion species and an optimized real time data analysis strategy as is described below. As a general rule, the mathematical deconvolution process should not be any slower than the mass spectrometric instrumental time for a typical tandem mass spectrometry (i.e, MS/MS or $MS^2$) experiment or run. Typically, this requires that the deconvolution process should be accomplished in less than one second of time. In the following, the inventors describe an algorithm that achieves the required analyses of complex samples within such time constraints, running as application software. Alternatively, the algorithm could be encoded into a hardware processor coupled to a mass spectrometer instrument so as to run even faster.

2.1. Key Features of Self Consistent Map Charge Assignment Algorithm 2.1.1. Use of Centroids Exclusively.

Standard mass spectral charge assignment algorithms (e.g., Senko et al., 1995) use full profile data of the lines in a mass spectrum. By contrast, the novel approach which is employed in the present methods uses centroids. The key advantage of using centroids over line profiles is data reduction. Typically the number of profile data points is about an order of magnitude larger than that of the centroids. Any algorithm that uses centroids will gain a significant advantage in computational efficiency over that standard assignment method. For applications that demand real-time charge assignment, it is preferable to design an algorithm that only requires centroid data. The main disadvantage to using centroids is imprecision of the m/z values. Factors such as mass accuracy, resolution and peak picking efficiency all tend to compromise the quality of the centroid data. But these concerns can be mostly mitigated by factoring in the m/z imprecision into the algorithm which employs centroid data.

2.1.2. Intensity is Binary.

Another key departure from most existing algorithms is the encoding of intensities as binary (or Boolean) variables (true/false or present/absent) according to the present methods. The present methods only take into consideration whether a centroid intensity is above a threshold or not. If the intensity value meets a user-settable criterion based on signal intensity or signal-to-noise ratio or both, then that intensity value assumes a Boolean "True" value, otherwise a value of "False" is assigned, regardless of the actual numerical value of the intensity. Again the encoding of a numerical value as a simple binary value results in a significant data reduction. In many programming languages, a double-precision value uses eight bytes of memory storage whereas a binary (or Boolean) value uses just a single byte. Also, comparing Booleans is intrinsically much faster than comparing double-precision variables. A well known disadvantage of using a Boolean value is the loss of information. However, if one has an abundance of data points to work with—for example, thousands of centroids in a typical high resolution spectrum, the loss of intensity information is more than compensated for by the sheer number of Boolean variables. Accordingly, the inventors' approach and, consequentially, the algorithms taught herein, exploit this data abundance to achieve both efficiency and accuracy.

Nonetheless, additional accuracy without significant computational speed loss can be realized by using, in alternative embodiments, approximate intensity values rather than just a Boolean true/false variable. For example, one can envision the situation where only peaks of similar heights are compared to each other. One can easily accommodate the added information by discretizing the intensity values into a small number of low-resolution bins (e.g., "low", "medium", "high" and "very high"). Such binning can achieve a good balance of having "height information" without sacrificing the computational simplicity of a very simplified representation of intensities. As a further example, given an observed centroid of interest and a putative charge state, Z, if a neighboring centroid (either a neighbor that is putatively part of an isotopic cluster or charge state distribution with the given centroid) has a very reduced intensity, say 10× smaller than the given centroid, one should not count this neighbor towards the score for that putative charge state Z. Excluding vastly smaller neighbors can improve the robustness of the charge assignment against random noise interference.

In order to achieve computational efficiency comparable to that using Boolean variables alone while nonetheless incorporating intensity information, one approach is to encode the intensity as a byte, which is the same size as the Boolean variable. One can easily achieve this by using the logarithm of the intensity (instead of raw intensity) in the calculations together with a suitable logarithm base. One can further cast the logarithm of intensity as an integer. If the logarithm base is chosen appropriately, the log(intensity) values will all fall comfortably within the range of values 0-255, which may be represented as a byte. In addition, the rounding error in transforming a double-precision variable to an integer may be minimized by careful choice of logarithm base. The inventors have found that using a logarithm base of 1.1 works very well. Thus each log level differs by only 10% from its two nearest log levels. Stated differently, the loss of precision from transforming the raw intensity to single-byte form is only 10%. Since most experimental precision in intensity exceeds 10%, and the difference we are interested in is more than 10×, the precision of 10% is sufficient.

To further minimize any performance degradation that might be incurred from byte arithmetic (instead of Boolean arithmetic), the calculations may that are employed to separate or group centroids only need to compute ratios of intensities, instead of the byte-valued intensities themselves. The ratios can be computed extremely efficiently because: 1) instead of using a floating point division, the logarithm of a ratio is simply the difference of logarithms, which in this case, translates to just a subtraction of two bytes, and 2) to recover the exact ratio from the difference in log values, one only needs to perform an exponentiation of the difference in logarithms. Since such calculations will only encounter the exponential of a limited and predefined set of numbers (i.e. all possible integral differences between 2 bytes (−255 to +255), the exponentials can be pre-computed and stored as a look-up array. Thus by using a byte representation of the log intensities and a pre-computed exponential lookup array, computational efficiency will not be compromised.

2.1.3. Mass-to-Charge Values are Transformed and Assembled into Low-Resolution Bins and Relative Charge State Intervals are Pre-Computed Once and Cached for Efficiency.

Another innovation of the approach taught in the present disclosure is in transformation of m/z values of mass spectral lines from their normal linear scale in Daltons into a more natural dimensionless logarithmic representation. As may be seen from the detailed discussion following, this transformation greatly simplifies the computation of m/z values for any peaks that belong to the same protein, for example, but represent potentially different charge states. This transformation involves no compromise in precision. When performing calculations with the transformed variables, one can take advantage of cached relative m/z values to improve the computational efficiency.

2.1.4. Simple Counting-Based Scoring and Statistical Selection Criterion.

Combining the encoding of centroid intensities as Boolean values, and the transformation of m/z values, the present approach encodes the whole content of any mass spectrum in question into a single Boolean-valued array. The scoring of charge states reduces to just a simple counting of yes or no (true or false) of the Boolean variables at transformed m/z positions appropriate to the charge states being queried. Again, this approach bypasses computationally expensive operations involving double-precision variables. Once the scores are compiled for a range of potential charge states, the optimal value can easily be picked out by a simple statistical procedure. Using a statistical criterion is more rigorous and reliable than using an arbitrary score cutoff or just picking the highest scoring charge state.

2.1.5. Iterative Process to Achieve Optimality and Defined by Complete Self Consistency of Charge Assignment.

The final key feature of the present novel approach is the use of an appropriate optimality condition that leads the charge-assignment towards a solution. The optimal condition is simply defined to be most consistent assignment of charges of all centroids of the spectra. Underlying this condition is the reasoning that the charge state assigned to each centroid should be consistent with those assigned to other centroids in the spectrum. The present algorithm implements an iterative procedure to generate the charge state assignments as guided by the above optimality condition. This procedure conforms to accepted norms of an optimization procedure. That is, an appropriate optimality condition is first defined and then an algorithm is designed to meet this condition and, finally, one can then judge the effectiveness of the algorithm by how well it satisfies the optimality condition. Most existing approaches lack this logical framework, and their theoretical merits are therefore difficult to assess objectively.

2.2. Details of Decomposition Algorithm

Figure 4:
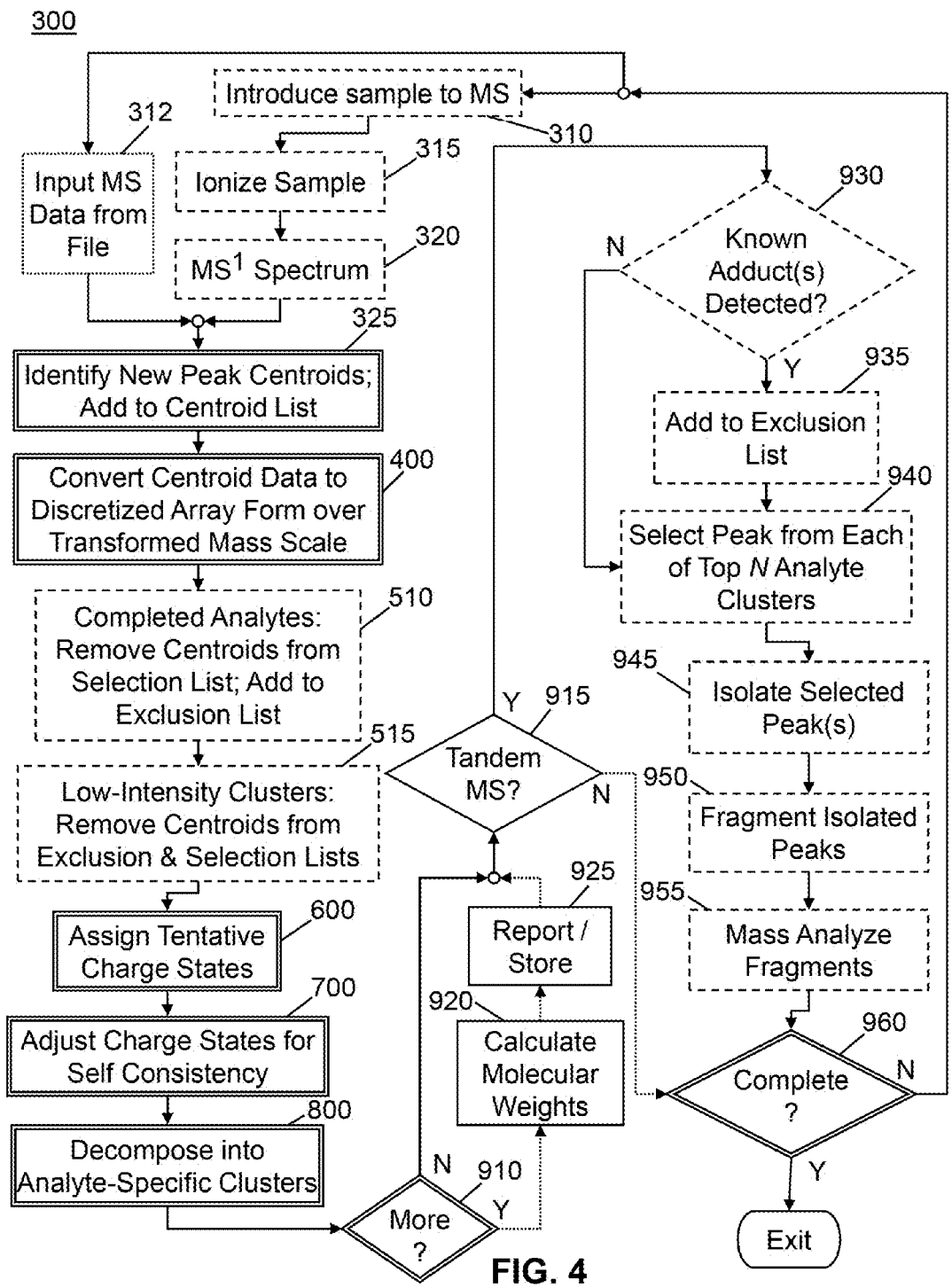
FIG. 4 is a flowchart of a general set of steps employed by various methods in accordance with the present teachings.

The inventors have developed methods that, inter alia, are capable of assigning self-consistent charge states to mass spectral lines and decomposing complex mass spectra comprising overlapping information pertaining to several analytes into multiple sets of lines, wherein each set of lines corresponds to a respective analyte. FIG. 4 is an overview flowchart of a general set of steps in accordance with the present teachings for accomplishing these results. Several operations listed in FIG. 4 are illustrated in greater detail in other flow diagrams of the accompanying set of drawings.

2.2.1. High-Level Methods.

As shown, FIG. 4 depicts at least two general execution or workflow pathways. According to a first general execution pathway or workflow—here termed "File-Deconvolution Workflow" only for purposes of reference—the methods of the present teachings are employed for the purposes of analyzing and possibly interpreting previously collected and stored mass spectral data. According to a second general execution pathway or workflow—here termed "Data-Dependent-Acquisition Workflow" only for purposes of reference—the methods of the present teachings are employed in a "real-time" or "online" fashion at the time that mass spectral data is being acquired and at least some aspects of the course of data acquisition are determined or controlled based on the results of computations or algorithms in accordance with the invention. Some steps illustrated in FIG. 4 are common to both of the above-defined execution pathways and are denoted in FIG. 4 by boxes defined by double lines. Other steps are exclusive to the Data-Dependent-Acquisition Workflow pathway and are denoted by boxes defined by dashed lines. At least one step—step 312 is exclusive to the File-Deconvolution Workflow pathway and is denoted by a box defined by a dotted line. Finally, steps 920 and 925, which are depicted by boxes with single solid lines, are optional with regard to the Data-Dependent-Acquisition Workflow but will generally be performed in conjunction with the File-Deconvolution Workflow. The File-Deconvolution Workflow will typically follow the general pathway indicated by dotted arrows at the lower portion of FIG. 4.

Still with reference to FIG. 4, the File-Deconvolution Workflow commences at step 312, in which previously acquired and stored mass spectral data in the form of at least one mass spectrum is input from an electronic storage device and made available for use in subsequent analysis. The mass spectrum may be an $MS^1$ spectrum, an $MS^2$ spectrum or, generally, any form of $MS^n$ spectrum. By contrast, the Data-Dependent-Acquisition Workflow begins at step 310 in which a sample is introduced into a mass spectrometer and is subsequently ionized in step 315. The sample introduction may be from a chromatograph, by means of injection or by other means. An $MS^1$ spectrum of the ions is generated in step 320. It is assumed that steps similar to steps 310, 315 and 320 would have been formed in the generation of the data that is input in the alternative pathway that includes step 312.

In step 325, new peak centroids (i.e., centroids not previously identified during the experiment in question or in a prior $MS^1$ spectrum of the input data); are identified and added to a list of centroids. In the next step 400, the m/z values of the centroids are transformed and the intensity data is converted to a Boolean-valued data array in which bins are assigned over the transformed m/z scale. The step 400 comprises a first substep 420 of constructing and populating a Boolean occupancy array and a second substep 460 of constructing and populating a relative separation matrix (see FIG. 5). The details of these substeps are described in greater detail in a subsequent section of this disclosure.

In step 510, which only applies to the Data-Dependent-Acquisition Workflow, centroids of analytes for which $MS^n$ analysis has been completed are removed from a "selection list" and added to an "exclusion list". The selection list includes one or more mass-to-charge (m/z) values or value ranges which are to be analyzed or which are being analyzed by the mass spectrometer by tandem mass analysis (MS/MS analysis) or possibly by $MS^n$ analysis, each such m/z value or range corresponding to a chemical component of the sample as identified by the methods of the present teachings. The exclusion list includes one or more mass-to-charge (m/z) values or value ranges which are to be excluded from future analysis either for the duration of an experiment or for a temporary time period during the experiment. The temporary time period, if employed, may be determined according to methods of the present teachings, as described in a subsequent portion of this disclosure. Alternatively for direct infusion or flow injection analysis, the one or more mass-to-charge values or value ranges which are to be excluded from future analysis can be performed on signal rank basis. Centroids depicting low-intensity mass spectral lines are removed from the exclusion and selection lists in step 515. The removed m/z values or ranges may be later added to the selection list if the corresponding mass spectral signal intensities subsequently increase during an experimental run.

Figure 8:
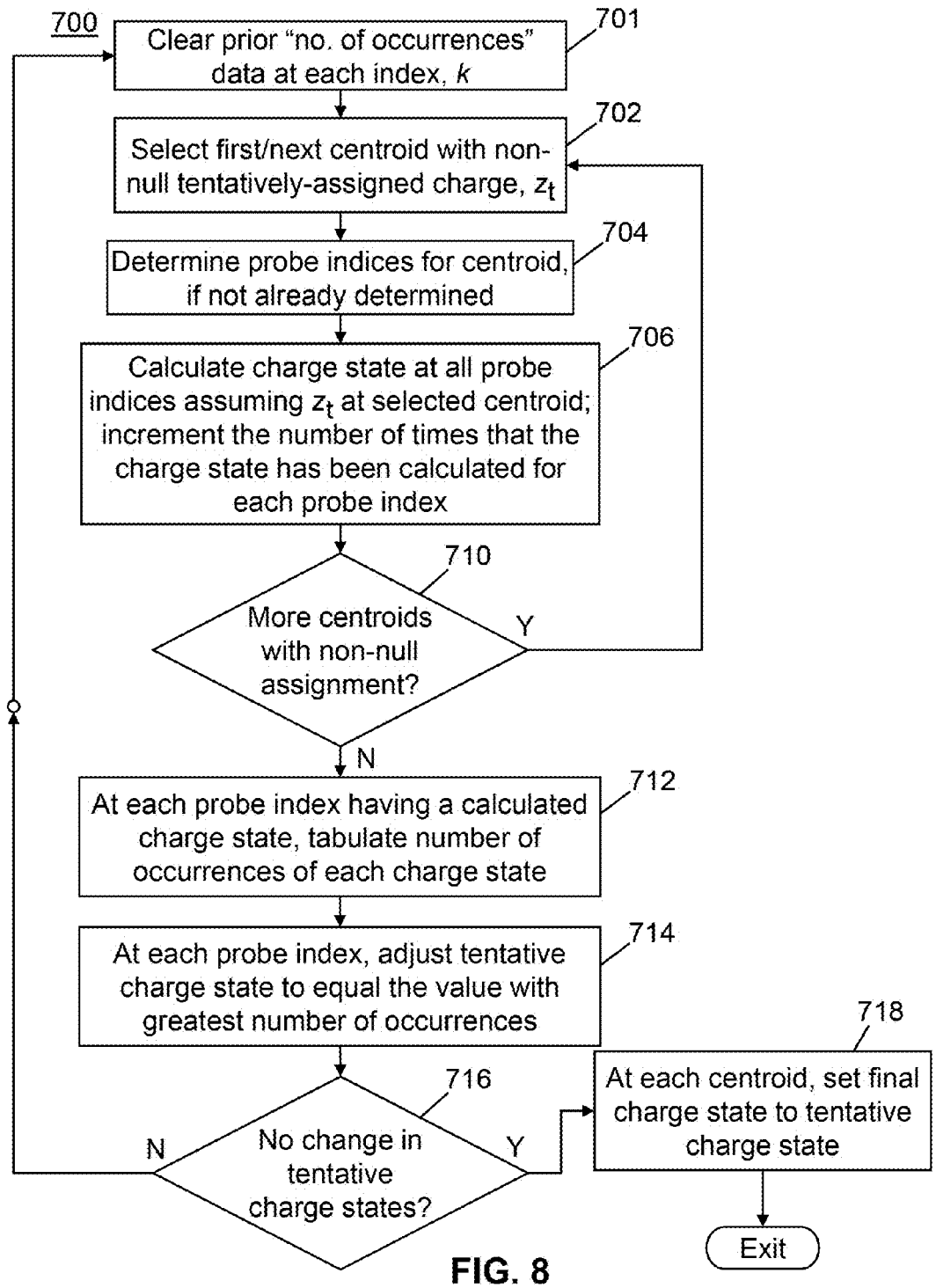
FIG. 8 is a flowchart of a method in accordance with the present teachings for adjusting a set of previously tentatively assigned charge states such that the resulting final assigned charge states are self-consistent.
Figure 9:
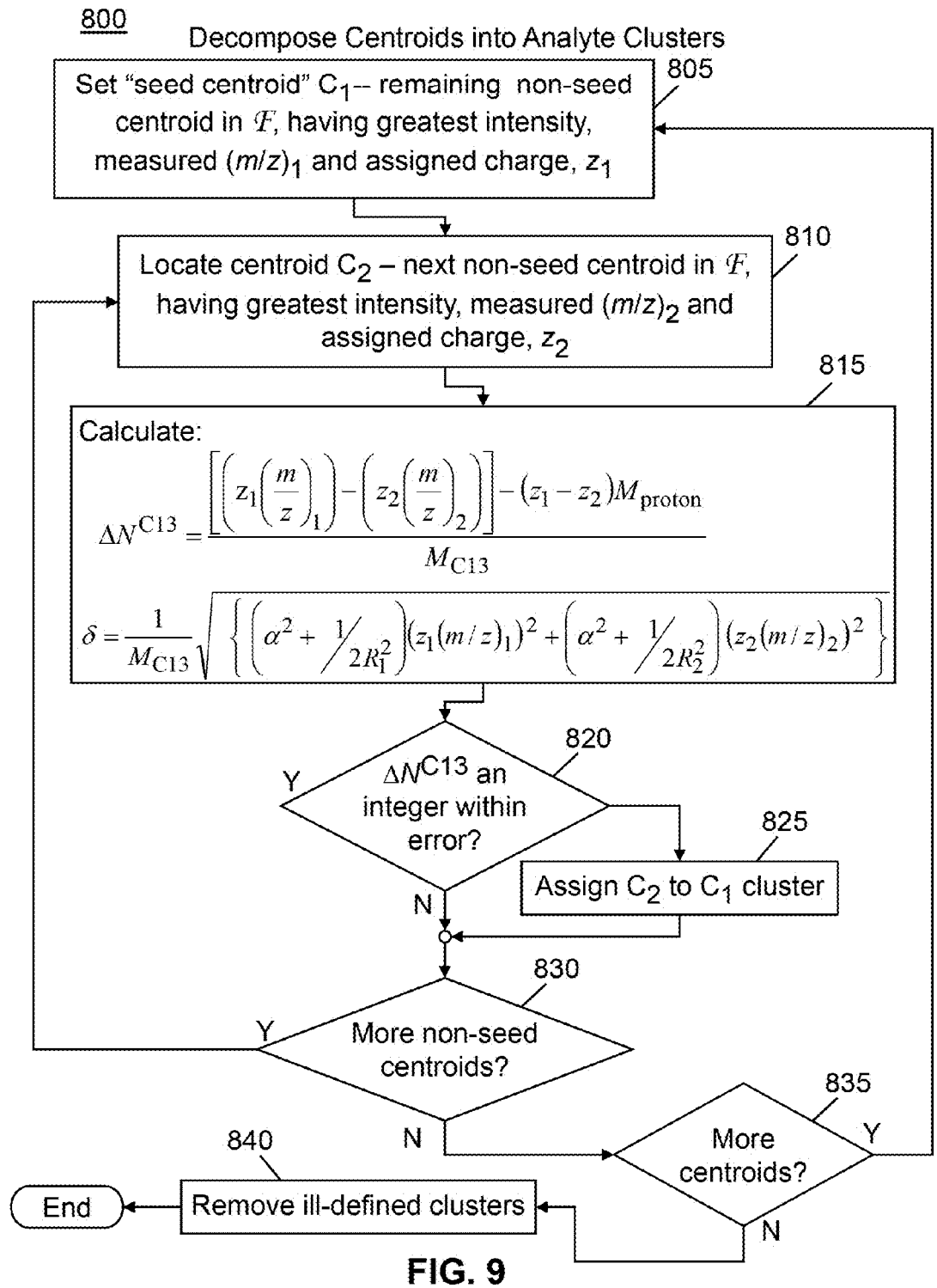
FIG. 9 is a flowchart of a method in accordance with the present teachings for decomposing a set of experimentally determined centroids having assigned charge states into analyte-specific clusters.

In step 600 tentative charge states assignments are made as outlined in FIG. 7 and further discussed below with reference to that figure. Then, in step 700, the tentatively assigned charge states are adjusted and final charge state assignments are made using requirements for self-consistency. The details of this process are outlined in FIG. 8 and further discussed below with reference to that figure. Once the final charge state assignments have been made, the experimentally observed centroids are decomposed into analyte-specific clusters in step 800 using information derived from the spacing of isotopic clusters. The details of step 800 are illustrated in FIG. 9 and described further with reference to that figure.

The execution of the method 300 may branch at step 910 along one of two possible execution paths indicated by solid-line arrows and dotted-line arrows, respectively. If real-time tandem mass spectrometry is being controlled by the results of the prior data analysis, then the method execution may follow the "N" branch (denoted by solid lines) from step 910 directly to step 915, thereby skipping steps 920 and 925. Alternatively, if more data analysis operations are to be conducted upon $MS^1$ data measured in step 320 or if data was previously input in step 312, then the "Y" branch of step 910 is followed whereafter molecular weights may be calculated or analyte species identified (step 920) and the results of the calculations may be reported or stored (step 925). As determined at step 915, if tandem mass spectrometry is to be performed, as will generally be true if the Data-Dependent-Acquisition Workflow execution path is being followed, then the method branches along the "Y" branch to step 930. Otherwise, execution proceeds, along the "N" branch to step 960.

Considering, now, the "online" execution path illustrated on the right-hand side of FIG. 4, a determination is made in step 930 if centroids attributable to known adducts are present in the considered set of centroids. If so (the "Y" branch of step 930) then the centroids corresponding to adduct species or to otherwise-modified species (for instance, species generated from loss of a neutral molecule) are added to the exclusion list in step 935. Otherwise, step 935 is bypassed. Step 940 is the commencement of top-down analysis in which a representative peak is selected for fragmentation from each of top P analyte-specific clusters determined in step 800. The following steps 945, 950 and 955 are conventional steps of, respectively, isolating ions of the m/z ratios corresponding to the selected centroids, fragmenting the isolated ions and performing a mass analysis ($MS^2$) of the product ions.

Execution of the method 300 may end after step 960, if either the mass spectral experimentation or the data analysis is complete. Otherwise, execution passes back to either step 310 at which the next portion of sample is introduced to the mass spectrometer or to step 312 at which the next portion of mass spectral data is input.

2.2.2. Building a Boolean-Valued Occupancy Array.

FIG. 6 shows the details of the step 420 of building an occupancy array, $[O_k]$. The values of the array are Boolean variables and the indices of the array correspond to the discretized transformed mass/charge values. The step 420 takes, as input, a collection of centroids, $C_i(1 \leq i \leq L)$ where L is an observed number of mass spectral lines. Each $C_i$ is characterized by its mass/charge $(m/z)_i$, its intensity $I_i$, its signal-to-noise ratio $(S/N)_i$ and its resolution $R_i$. Next, a filtering of the centroids is performed (step 422) by collecting the subset $\{\mathcal{F}\}$ of centroids which pass a user settable criterion of intensity and signal to noise thresholds. Next, in step 424, a mass/charge transformation is performed on each $C_i$ in $\{\mathcal{F}\}$ by taking the natural log of the mass/charge value minus that of the mass of a proton, $M_{proton}$ as in Eq. 1.

$$T(m/z)_i = \ln((m/z)_i - M_{proton}) \qquad \text{Eq. (1)}$$

After this transformation, each centroid, $C_i$ in the subset $\{\mathcal{F}\}$ is characterized by $T(m/z)_i$, $I_i$, $(S/N)_i$ and $R_i$. The greatest, $T(m/z)_{High}$, and the smallest, $T(m/z)_{low}$, values of the $T(m/z)$ values from subset $\{\mathcal{F}\}$ are noted in step 426. This information is then used to create the array $[O_k]$ of values, where each element of the array is a Boolean-valued "occupancy" which maintains a record of whether or not a "signal" is deemed to occur at the respective transformed mass-to-charge value, $T(m/z)_k$, associated with the array element. Upon creation, each element, $O_k$, of the array is initialized to the Boolean value "FALSE". The number of discrete elements in the array, or "length" of the array $[O_k]$ is denoted as $L_{occs}$, which is determined as $$L_{occs} = \frac{(T(m/z)_{high} - T(m/z)_{low})}{D} \qquad \text{Eq. (2)}$$

where D is the width of each bin in the array and is $D = MA/10^6$, where MA, typically 10, denotes a user settable parameter of the mass accuracy of the spectrum of interest.

After creation and initialization, the array $[O_k]$ must be populated (performed in step 436) with meaningful values. The elements of the occupancy array $[O_k]$ are indexed by the variable, $k(1 \leq k \leq L_{occs})$ whereas the elements of the filtered centroid subset $\{\mathcal{F}\}$ are indexed by the variable, i. The latter indices are converted into corresponding k-values in step 430, in which, for each centroid, $C_i$, in the subset $\{\mathcal{F}\}$, the corresponding index, $k_i$, is determined as follows:

$$k_i = \frac{(T(m/z)_i - T(m/z)_{low})}{D} \qquad \text{Eq. (3)}$$

and is rounded to the nearest integer (the rounding operation is indicated by the operator "ROUND[ ]" in FIG. 6. If the resolution, $R_i$, of the centroid $C_i$ is available (some spectra such as those collected in the centroid mode, may not have this defined), then the "Y" branch of the decision step 432 is followed, in which the additional indices $k_i^{Lo}$ and $k_i^{Hi}$ are calculated in step 434a as follows $$k_i^{Lo} = \frac{(T(m/z)_i - 0.5(R_i))}{D} \qquad \text{Eq. (4a)}$$

$$k_i^{Hi} = \frac{(T(m/z)_i + 0.5(R_i))}{D} \qquad \text{Eq. (4b)}$$

with values rounded to the nearest integer. For mass spectrometer instruments that include Fourier-Transform based mass analyzer, such as instrument systems employing an Orbitrap™ electrostatic trap mass analyzer, the instrument acquisition software automatically calculates the centroid resolution values, $R_i$, and, thus, these values become attributes of the centroids. These, along with other attributes, are captured in the raw file that the instrument generates during the measurement procedure and, thus, the calculation algorithms in accordance with the present teachings may simply input these values from the file. For ion-trap-type instruments, the centroid information is not as complete in the raw file and, in such situations, the user can enter an appropriate resolution value. In cases in which $R_i$ is not available, these indices are instead set to $k_i-1$ and $k_i+1$, respectively, in step 434b. Finally, in step 436, array values are all set to the Boolean value "TRUE" for indices ranging from $k_i^{Lo}$ to $k_i^{Hi}$, namely $$O_k := \text{TRUE}; k_i^{Lo} \leq k \leq k_i^{Hi} \qquad \text{Eq. (5)}$$

2.2.3. Building a Relative Separation Matrix (RSM).

Figure 5:
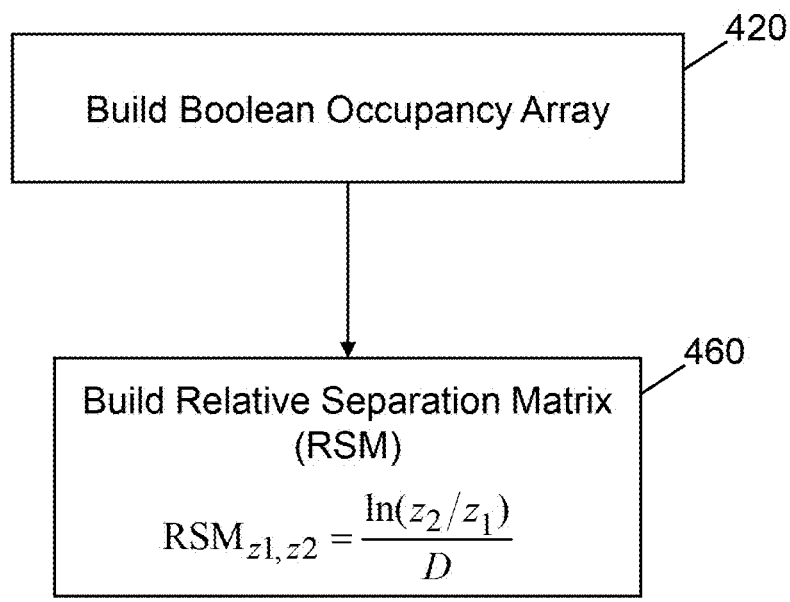
FIG. 5 is a flowchart of a method to convert experimentally measured mass spectral centroids to a transformed matrix form, in accordance with the present teachings.

As shown in FIG. 5, step 460 is the step of constructing a relative separation matrix and is the second sub-step of the general step 400. The creation of a relative separation matrix is motivated by observation that, given two centroids $C_1$ and $C_2$, then, if they belong to the same protein isotopic peak but differ just in charge states, then their mass/charge values are related as $$|z_1| \times ((m/z)_1 - M_{proton}) = |z_2| \times ((m/z)_2 - M_{proton}) \qquad \text{Eq. (6)}$$

in which $z_1$ are the charge state of the centroids $C_1$ and $C_2$ respectively, and $M_{proton}$ is the mass of a proton. The charge state values, $z_1$ and $z_2$, will generally be either all positive or all negative depending on the mode of ionization used in the mass spectrometer instrument conducting the analyses. Performing the transformation as described in Eq. (1) yields the relationship that $$T(m/z)_1 = T(m/z)_2 + \ln|z_2/z_1| \qquad \text{Eq. (7)}$$

The important property of Eq. (7) is that the transformed $T(m/z)_i$ values at different charge states are related by an additive factor that is independent of the transformed values. Thus one can pre-compute and cache the quantities $\ln(z_2/z_1)$ as a matrix that can be reused in subsequent calculations by simple look-ups by pre-computing the RSM. The absolute values of the charge states will generally range between unity and some maximum value, $|Z_{max}|$ or, more specifically, $1 \leq z_1, z_2 \leq |Z_{max}|$. The last step is to discretize the $\ln|z_2/z_1|$ matrix by dividing by D as in Eq. (4):

$$RSM_{z1,z2} = \frac{\ln|z_2/z_1|}{D} \qquad \text{Eq. (8)}$$

The limits of the matrix, determined by $Z_{max}$, may be set by a user anticipating the maximum and minimum charge states that will be encountered in a set of spectra. Alternatively, $Z_{max}$ may be a pre-determined or pre-calculated value. Typically, the absolute values of the charge states range from 1 to 50 for a top down experiment. So in such a case, RSM will be a 50×50 anti-symmetric matrix.

2.2.4. Building a Scoring Distribution for Each Centroid and Using it to Assign Tentative Charge States.

Figure 7A:
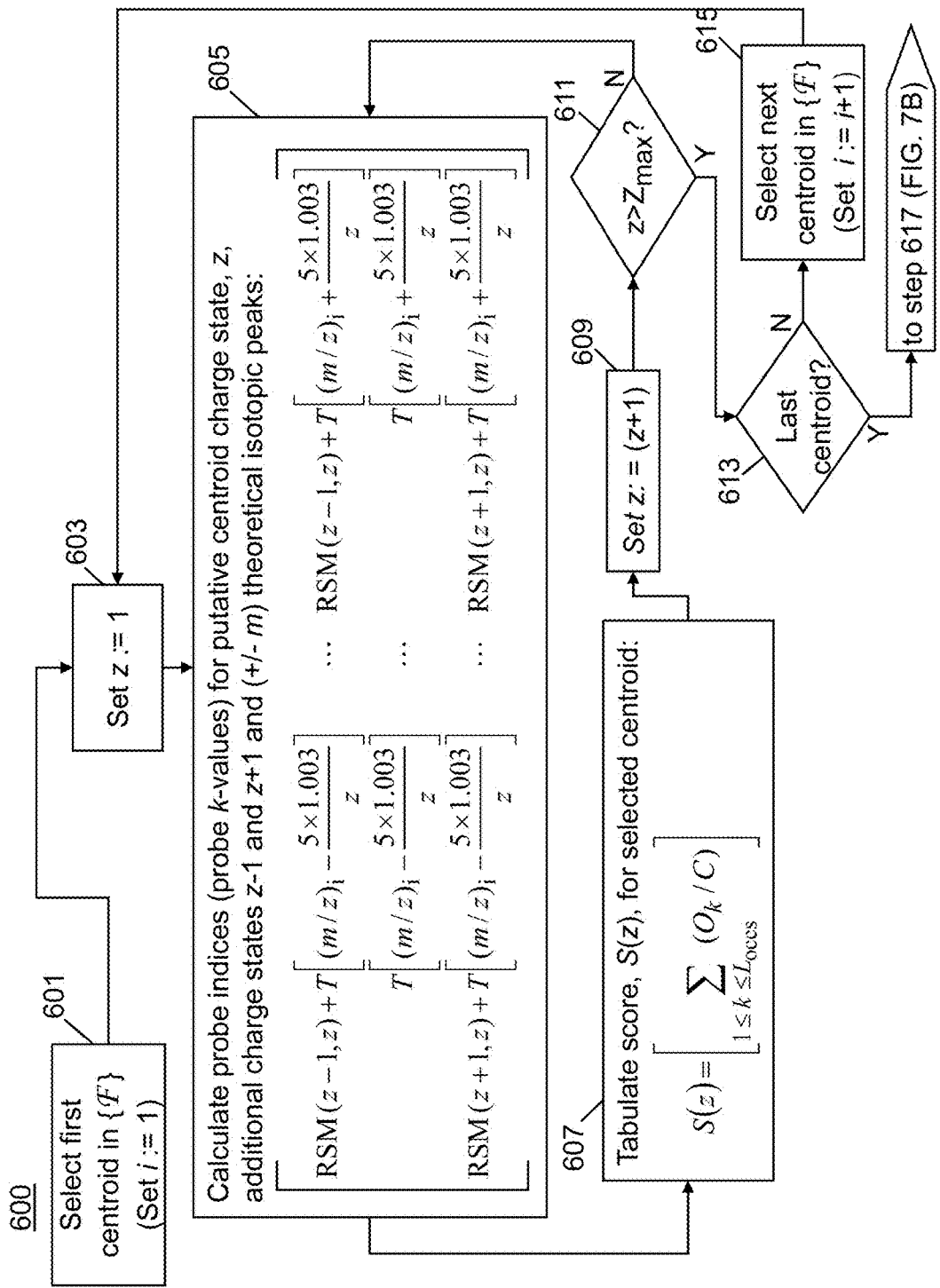
FIG. 7, comprising FIG. 7A and continuation on FIG. 7B, is a flowchart of a method in accordance with the present teachings for assigning tentative charge states for a plurality of experimentally determined mass spectral centroids.
Figure 7B:
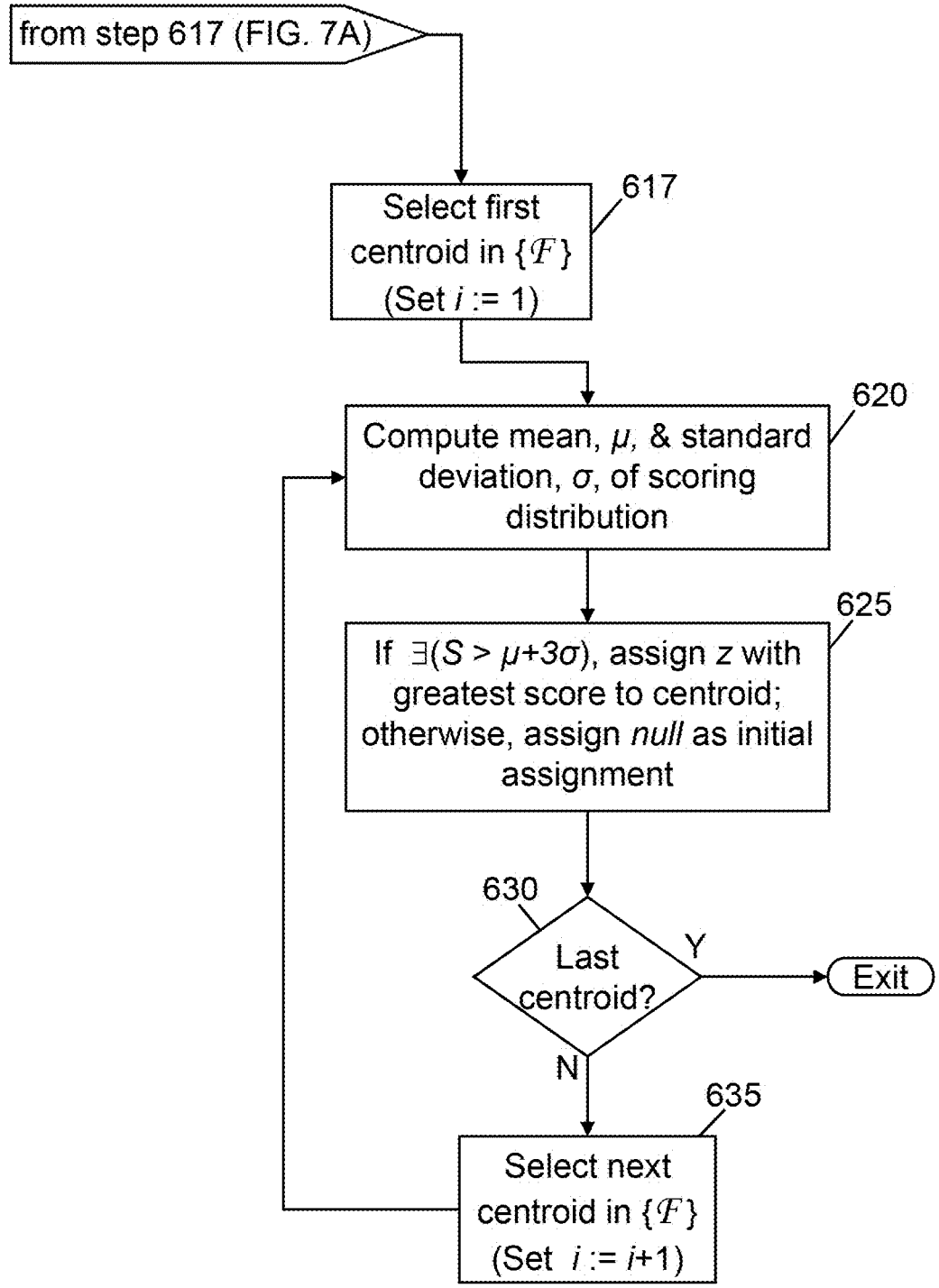

Before a self-consistent set of charge assignments may be determined by iteration (in step 700, FIG. 8), a reasonable initial set of tentative charge assignments must be formulated. The step 600, the details of which are shown in FIGS. 7A and 7B, generates this initial set of by assigning a likely charge state to various of the centroids of subset $\{\mathcal{F}\}$. Steps

601-615 consider each such centroid, in turn, and, for each considered centroid, step through various putative values of putative charge state, z, from a minimum charge state value, $Z_{min}$ up to a maximum charge state value, $Z_{max}$. For example, putative charge states from z=1 through z=50 might be considered for each centroid. For each combination of a centroid, $C_i$ (as selected in step 601 or step 615) and a putative charge state $z_i$, (as set in either step 603 of 609), a set of "probe indices" $k_p(C_i, z_i)$ is calculated in step 605. The probe indices are a set of k-values that reference bins of the occupancy array, $[O_k]$, for purposes of testing for "TRUE" values at each of these indices. The $k_p(C_i, z_i)$ matrix includes a first row having the indices corresponding to the discretized $T(m/z)_i$ values of the (+/−m) theoretical isotopic peaks of the selected centroid $C_i$. For example, if m=5, the probe indices corresponding to the (+/−5) theoretical isotopic peaks are the transformed values of:

$$(m/z)_i - \frac{(5)(1.003)}{z}, (m/z)_i - \frac{(4)(1.003)}{z}, \ldots, (m/z)_i + \frac{(5)(1.003)}{z}$$

The $k_p(C_i, z_i)$ matrix also includes two additional rows, the elements of which are calculated by generating, for each of the 2 m probe indices in the row described above, an additional probe index corresponding to expected location of the z−1 peak and another additional probe index corresponding to the expected location of the z+1 peaks. Specifically, the indices $[k_p(C_i, z_i) + RSM(z_i-1, z_i)]$ and $[k_p(C_i, z_i) + RSM(z_i+1, z_i)]$ are generated, where RSM is the pre-computed and cached relative separation matrix described above. Note that the $k_i$ index of the centroid $C_i$, itself, is excluded from the probe indices matrix because, at this stage of execution of the algorithm, it is given that the occupancy array contains a value of "TRUE" at such index. Similarly, one can also increase the probe matrix in include more charge states of (z−m, z−m+1, . . . , z+m−1, z+m) instead of just (z−1, z, z+1) as described above.

In step 607, a score value is calculated for each tested z value and each centroid $C_i$. The set of scores is used to generate a scoring distribution for each z value. Each score S(z) is calculated by summing, for each possible value of $z_i$, the experimentally-derived occupancy values. Specifically, the score for each value of z is determined by $$S(z) = \Sigma O_k / C \qquad \text{Eq. (9)}$$

where the sum is over k of $k_p(C_i, z_i)$ such that $(1 \le k \le L_{occs})$ and C is just the number of such k's. In other words, the score at z is just the fraction of $k_p(C_i, z_i)$ indices that are "occupied" by a measured above-threshold mass spectral signal (i.e., a value of "TRUE") as coded in occupancy array constructed in step 420 (FIG. 5). Thus, the calculation in step 605 is a form of streamlined approximate "inner product" calculation, with the greatest possible score of any single calculation being unity. The score distribution is formed by summing the scores for each value of z from the lowest to the highest user settable limits. Using our example of 1 and 50 as the low and high limits, we will end up with a distribution of 50 scores for each centroid.

Decision step 611 determines, for each centroid, if the maximum value of z has been considered. If not then execution returns to step 605 for calculation of probe indices with a new value of z (as set in step 609). Otherwise, execution branches to decision step 613 which determines if the last centroid in the subset $\{\mathcal{F}\}$ has been considered. If not, then execution proceeds to step 615 in which the next centroid is selected and then to step 603 in which the z-value is reset to its initial state. Otherwise, execution proceeds to step 617 (FIG. 7B) at which the process of formulating tentative charge assignments is begun.

Steps 617-635 shown in FIG. 7B illustrate the process of making tentative charge assignments using the scoring distributions previously generated in multiple iterations of step 607 (FIG. 7A). In step 617, the first centroid is selected; later the choice of centroid being considered is updated in step 635. After either of these two steps, the mean, $\mu$, and standard deviation, $\sigma$, of the respective scoring distribution is computed in step 620. Thus, repeated iteration of steps 620-635 causes these statistical measures to be computed for the scoring distribution associated with each centroid. In step 625, if there are any scores larger than mean $\mu+3\sigma$, then the z-value with the largest score is assigned to the centroid as the initial charge-state assignment. If there are no scores larger than $\mu+3\sigma$, then a null value as provided as the initial assignment for the centroid in question.

2.2.5. Achieving Optimality of Completely Self Consistent Charge Assignment by Iteration.

After the tentative charge-state assignments have been made in step 600, execution of the method 300 (FIG. 4) proceeds to step 700 in which the tentative charge state assignments are adjusted. Details of the step 700 are shown in FIG. 8. The optimal condition is simply defined to be most consistent assignment of charges of all centroids of the spectra. Underlying this condition is the reasoning that the charge state assigned to each centroid should be consistent with those assigned to other centroids in the spectrum.

The details of the step 700 shown in FIG. 8 implement an iterative procedure to generate the charge state assignments as guided by the above optimality condition. Each centroid with a non-null assignment (as assigned in step 625 of FIG. 7B) is considered, in turn. Each of these may be associated with a set of probe indices as indicated in step 605 of FIG. 7A. This process is repeated for all centroids with a non-null assignment, and a new charge state distribution is determined at each probe index. Specifically, in step 702, the first or next centroid having a non-null tentatively assigned charge state, $z_t$, is selected. In step 704, the probe indices for the centroid in question are generated, as previously described with respect to step 605 of FIG. 7A, if necessary. Then, in step 706, a charge state is calculated at each of the probe indices corresponding to the centroid in question, assuming that the charge state of the selected centroid is $z_t$. For each probe index, a record is kept of how many times each charge state is calculated for that probe index. Before beginning each loop through steps 702-710, these records are cleared (re-set zero) in step 701. Thereafter, during each loop, each time that a charge state is calculated for a probe index in step 706, the number of times that the charge state has been so calculated at that probe index is incremented. If, at step 710, there are additional centroids with a non-null assignment, then execution returns to step 702 and the next such centroid is selected.

After the last centroid has been considered, execution branches to step 712. In step 712, the number of occurrences of each charge state (as calculated in step 706) are tabulated at each probe index, thereby generating a charge state distribution for each probe index. Using the new charge-state distributions, a "charge assignment by majority" (CAM) is obtained in step 714 by adjusting tentative charge state at each probe index so at to equal the charge state with the highest number of tabulated at the respective index. The set of all such CAM charge assignments forms an array of values—the charge assignment by majority array.

The charge assignments are considered to be inconsistent if, at step 716, the values of the CAM array differ from the charge-state values used in the generation of the CAM array. By contrast, a completely self consistent charge assignment is defined as the assignment of charge at each index such that it is in complete concordance with that from the CAM array resulting from it. Thus, at step 716, the adjusted tentative charge states are compared to their prior values. If there has been a change that is greater than a certain tolerable limit, then the charge assignments are not self-consistent. In this case, the "N" branch of step 716 is followed and execution returns to step 701 whereby a new set of calculations are performed so as to achieve self consistency. Thus, a set of repetitions of the CAM array determination are performed by using the charges from each CAM to generate a subsequent CAM. Optimality is achieved when convergence is achieved—that is, the CAM generates the same CAM.

In practice, one might not achieve exact convergence by this procedure. However, the inventors' experience shows that, after a few iterations, the incidence of non-concordance becomes negligibly small and thus one can stop the iteration at a very good charge-state assignment. Accordingly, in step 716, convergence is considered to be operationally achieved when the difference in successive CAM arrays is within a certain tolerable limit (i.e., within a certain tolerance). In this case, execution branches to step 718 at which the final self-consistent charge state and each centroid is set to be equal to the tentative charge state at which the operational convergence occurred.

2.3. Determination of Analyte-Specific Clusters

The clustering approach starts with the clustering criterion defined by Eq. (10), in which the number of $C^{13}$ non-monoisotopic peaks, $\Delta N^{C13}$, that are reasonably expected to occur within a restricted m/z range is given by $$\text{Number of } C^{13} \text{ Peaks} = \frac{[(z_1(m/z)_1) - (z_2(m/z)_2)] - (z_1 - z_2)M_{proton}}{M_{C13}} \quad \text{Eq. (10)}$$

in which $z_1$ are the charge states assigned to mass spectral lines, $(m/z)_1$ and $(m/z)_2$ are the experimentally measured mass to charge values, $M_{C13}$ is the mass difference between the isotopes of carbon, $C^{13}$ and $C^{12}$, and $M_{proton}$ is the mass of a proton. The error ($\delta$) or standard deviation associated with the calculation is computed from a user-supplied value of accuracy, $\alpha$, which is defined in ppm (e.g., see FIG. 11B), as well as the resolutions $R_1$ and $R_2$ of the centroids under consideration as described in Eq. (11)

$$\delta = \frac{1}{M_{C13}} \sqrt{\{(\alpha^2 + 1/2R_1^2)(z_1(m/z)_1)^2 + (\alpha^2 + 1/2R_2^2)(z_2(m/z)_2)^2\}} \quad \text{Eq. (11)}$$

To determine if any two centroids (peaks) belong to the same analyte-specific cluster (associated with a particular bio-molecule such as a protein), the theoretical $\Delta N^{C13}$ value is calculated using Eq. (10). If the calculated $\Delta N^{C13}$ value is an integer within the measurement error, as computed as in Eq. (11), then the two centroids are considered to belong to the same analyte-specific cluster, provided that the number of $C^{13}$ peaks does not exceed a user defined limit (typically 10 to 15). Of course, one skilled in the art can easily use a multitude of other similar statistical tests such as the z-test, or t-test to determine whether the two peaks differ by an integral number of $C^{13}$, given the uncertainties of their m/z's as encoded in $\alpha$ and the resolution R's.

The step 800 of decomposing the mass spectral lines into analyte-specific clusters shown in FIG. 9 makes use of the above reasoning. The step 800 considers centroids for which charge assignments have been made, as previously described. Step 805 begins with the charge-assigned centroid that has the greatest experimentally-observed intensity. The so-selected centroid is then uses as a "seed" for the first cluster. Then, proceeding in order of decreasing intensity (steps 810 through 830), a check is made to determine if the next centroid in the list clusters with the seed centroid of this cluster. This check is performed by first calculating $\Delta N^{C13}$ and its error, $\delta$, using Eq. 10 and Eq. 11, respectively (step 815). If it is noted, in the decision step 820, that the presently-calculated value of $\Delta N^{C13}$ is an integer, within the calculated error, then execution follows along the "Y" branch to step 825 in which the centroid under consideration is grouped together with the seed centroid as belonging to a single cluster. If not, then the "N" branch is followed such that, in step 830, if there are remaining non-seed centroids, execution returns to step 810 in which the next-intense non-seed centroid is selected for cluster checking. If, at step 830, the list of non-seed centroids is exhausted (that is, there are no remaining non-seed centroids having intensities less than the presently considered centroid) but there are remaining non-clustered centroids (determined in step 835), then execution returns to step 805 in which a new cluster is started with using the most-intense non-seed centroid as the new seed. Subsequent iterations check against all cluster seeds created and create new clusters if the new centroid does not cluster with any preceding clusters.

Finally, in step 840, a simple heuristic is employed to determine if any cluster created by the clustering algorithm is "healthy". In our initial implementation, we use the simple rule that a "healthy" cluster must have at least four distinct charge states or at least N (user settable, but defaulting to 15) member centroids. We filter out clusters that are not "healthy" according to these criteria. After the removal of "unhealthy" clusters, the remaining are the final analyte-specific clusters, each representing a different bio-polymer or other high-mass compound.

2.4. Protein Molecular Weight Calculations

One of the more common ways of calculating the mono-isotopic molecular weight, $M_{mono}$, of a protein from an experimental high-resolution spectrum is to use the so-called "Averagine" method (Senko, M. W, Beu, S. C. and McLafferty, F. W., 1995, Determination of monoisotopic masses and ion populations for large biomolecules from resolved isotopic distributions. J. Am. Soc. Mass Spectrom., 6: 229-233), which itself is an extension of an earlier method for low-resolution data (Zubarev, R. A. and Bonddarenko, P. V., 1991, An a-priori relationship between the average and monoisotopic masses of peptides and oligonucleotides. Rapid Commun. Mass Spectrom., 5: 276-277). Briefly, the Averagine method first models an experimental isotopic cluster by a hypothetical model molecule—the "Averagine" molecule. By optimizing the fit between the experimental and the theoretical isotopic distribution, one can arrive at an estimate of the mono-isotopic mass desired.

The Averagine technique is used within various mass spectrometry peak decomposition and analysis algorithms that are commercially available from Thermo Fisher Scientific of Waltham Mass. USA. Although the Averagine method has been highly successful, the present inventors are motivated to develop a different approach based on the following considerations: (1) Calculation speed. Averagine fitting may be time consuming, a not insignificant consideration for real-time applications, such as those described herein in which decisions are automatically made, in real time, regarding which of several observed ions to fragment. It should be noted, however, that, in situations where a large number of spectral fits are not required, calculation speed may not pose any concern; and (2) Mass accuracy. For a larger molecular weight protein whose signature appears in a crowded spectrum, the corresponding isotopic cluster tends to be noisy and incomplete (missing isotopes—especially the edges, missing charge states etc). The use of an Averagine fit may not be appropriate in such instances.

The present inventors therefore here teach an approach that promises to produce a robust estimate of the mono-isotopic mass that is very easy to calculate and more resistant to noise and artifacts. The main goal is robustness and precision, accepting the compromise that the estimate might be biased. In short, the estimate might not be the "true" mono-isotopic mass (but nonetheless very close to it), but it should be robust/stable in face of experimental imperfections. The error should deviate from the true mono-isotopic mass by either 0 or +/−1 dalton (1 Da) precisely, after taking mass accuracy into consideration. The inventors here point out that robustness, in many cases, is more important than accuracy. For example, if one were to build a molecular weight database based on experimental data, the ability to produce the same answer both while building the database and while testing the database by new data is generally desired, even if the estimates are potentially off by 1 Da from the true molecular weight but nonetheless are identical from experiment to experiment.

The approach starts with three simple observations: (1) the isotopic patterns for most proteins are due to the $C^{12}/C^{13}$ binomial distribution and all the other isotopes are of too low an abundance to warrant consideration; (2) the mode (i.e., the peak having the greatest intensity) of a binomial distribution is a very robust feature of the binomial distribution compared to either the average, the standard deviation, or the exact boundaries of the distribution, and (3) for the binomial distribution, the mode is located less than 1 Da to the left of the average (see Table 1 in FIGS. 10A, 10B, 10C, and 10D). This means that the mode is a very usable replacement for the average, which itself is more difficult to estimate for more noisy data. For example, a distribution truncated at the edges will give rise to an unreliable average estimate while the mode, unless the distribution is highly distorted, is very stable against such truncations.

The starting point for the calculation is defined by $\overline{M}$, the observed mode of an isotopic cluster. Zubarev's approach to calculate the first approximation of the monoisotopic mass is then employed where:

$$M_1 = \overline{M} \times 0.999316 \qquad \text{Eq. (12)}$$

The second approximation of the monoisotopic mass is then defined by:

$$M_2 = \overline{M} - n \times 1.003 \qquad \text{Eq. (13)}$$

where n is the smallest integer such that $M_2 \geq M_1$. Finally, in the calculation of the monoisotopic mass, $M_{mono}$, if there is an experimental peak of the cluster which is within 1 Dalton greater than $M_2$ then:

$$M_{mono} = M_2 + 1.003 \qquad \text{Eq. (14a)}$$

otherwise, $$M_{mono} = M_2 \qquad \text{Eq. (14b)}$$

This method of calculating the mono-isotopic mass has been incorporated in the results illustrated herein. The inventors' results show that the predictions compare very favorably to those predicted by the Averagine method. For large proteins, testing on standard proteins indicates that the mono-isotopic mass estimate is stable. In addition, a cluster molecular weight is also calculated for closely related peaks or proteoforms. We term the result of such a calculation as the "Cluster Molecular Weight". After all the proteoforms have been discovered in a batch, a cluster analysis of all the proteoforms is performed using the more discriminatory error function:

$$\text{Error} = \min|w_1 - w_2 - N \times 1.003| \qquad \text{Eq. (15)}$$

over $-3 \leq N \leq 3$. If Error<0.5 $(w_1 + w_2) \times 10$ ppm, then $w_1$ and $w_2$ should be considered equivalent. Each proteoform will then be mapped into clusters of equivalent proteoforms represented by a consensus monoisotopic mass. This mass is termed and stored as "consensus MW".

2.5. Program Input and Output

Figure 11A:
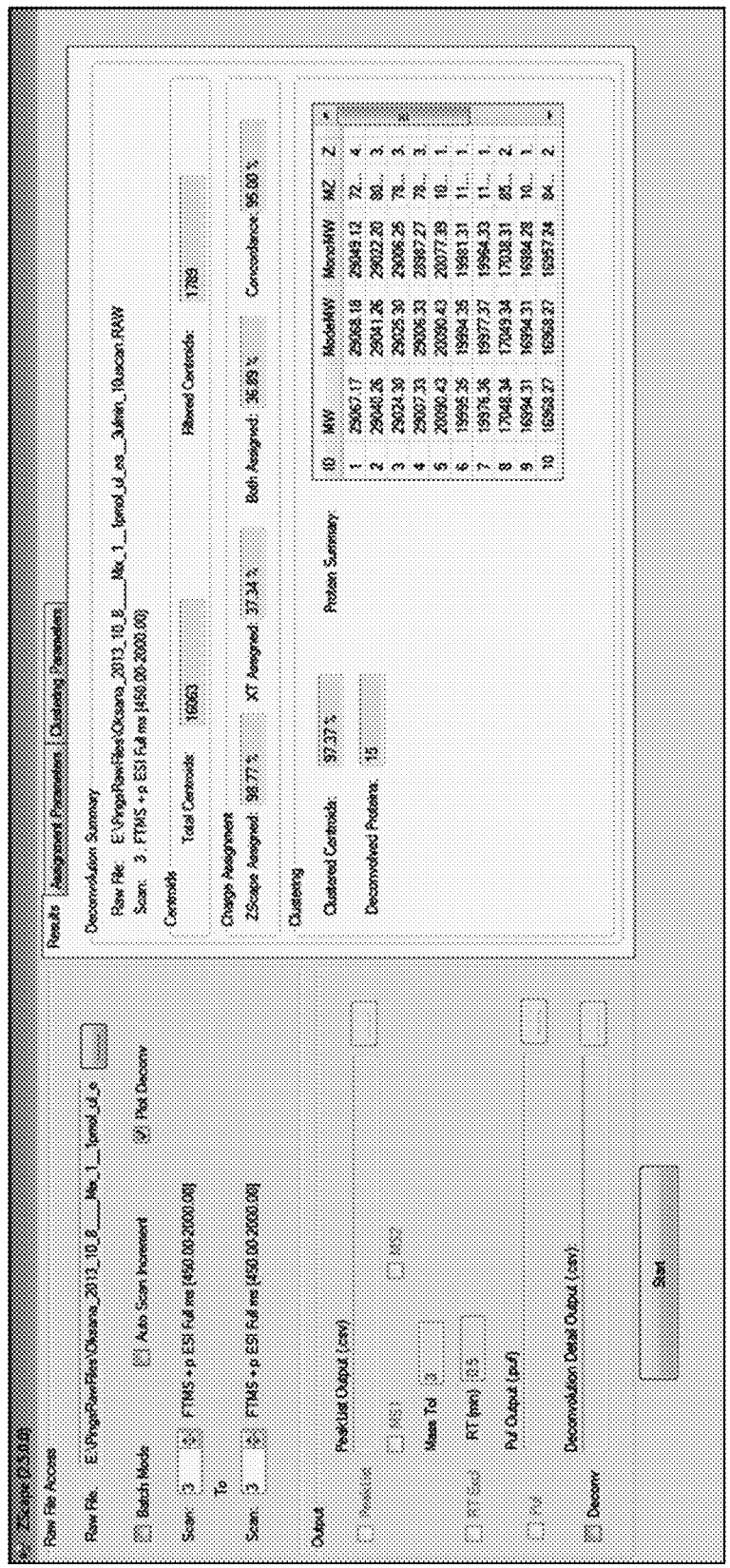

FIG. 11A shows the starting page (i.e., a visual display screen capture) of a post-data-acquisition version of a computer program that employs the data dependent methods described herein. On the left hand side of the display illustrated in FIG. 11A, the "Raw File" box serves as the input line for the mass spectrometry data file to be processed. The "Batch Mode" check box can be enabled, thereby allowing a user to process multiple data files, while the "Auto Scan Increment" check box is used to enable processing of consecutive spectra. Results from the post-data-acquisition version of the program can be plotted in a display by the user enabling the "Plot Deconv" check box. The minimum and maximum spectrum (scan) number to process is set by the "Scan buttons" which directly default to the file length (in scans) or which can be set by the user.

Output can be controlled as seen in the lower left hand side of FIG. 11A, by causing results to be output to a peak list and by the user specifying the output as either MS1 or MS2 type data (in csv file format). The "Mass Tol" parameter governs how tightly the mono-isotopic masses found by are clustered across different scans (each "scan" essentially being a measurement of a respective mass spectrum at a respective time). For each scan, the deconvolution algorithm produces a list of mono-isotopic masses corresponding to the deconvoluted proteins it has discovered. But each scan is processed independently. As a result, a protein may appear over many scans, and the algorithm will calculate its mono-isotopic mass for each scan independently. In such a case, there might be scan-to-scan differences in the calculated isotopic mass, even for the same protein. The main factor contributing to the variation in mass is data quality. For example, for less abundant proteins, the isotopic clusters tend to be poorly defined and variable from scan to scan, leading to variation in the determined mono-isotopic mass. For most cases, the differences in mass for the same protein are all multiples of the 1.003 Dalton, with the multiples less than 3×. Sometimes, especially for larger proteins (30 KD), that multiple could be as large as 10×. The mass tolerance (Mass Tol) parameter limits how much such variation is considered to be acceptable and defaults to 3; however this parameter can be set by the user.

Figure 11D:
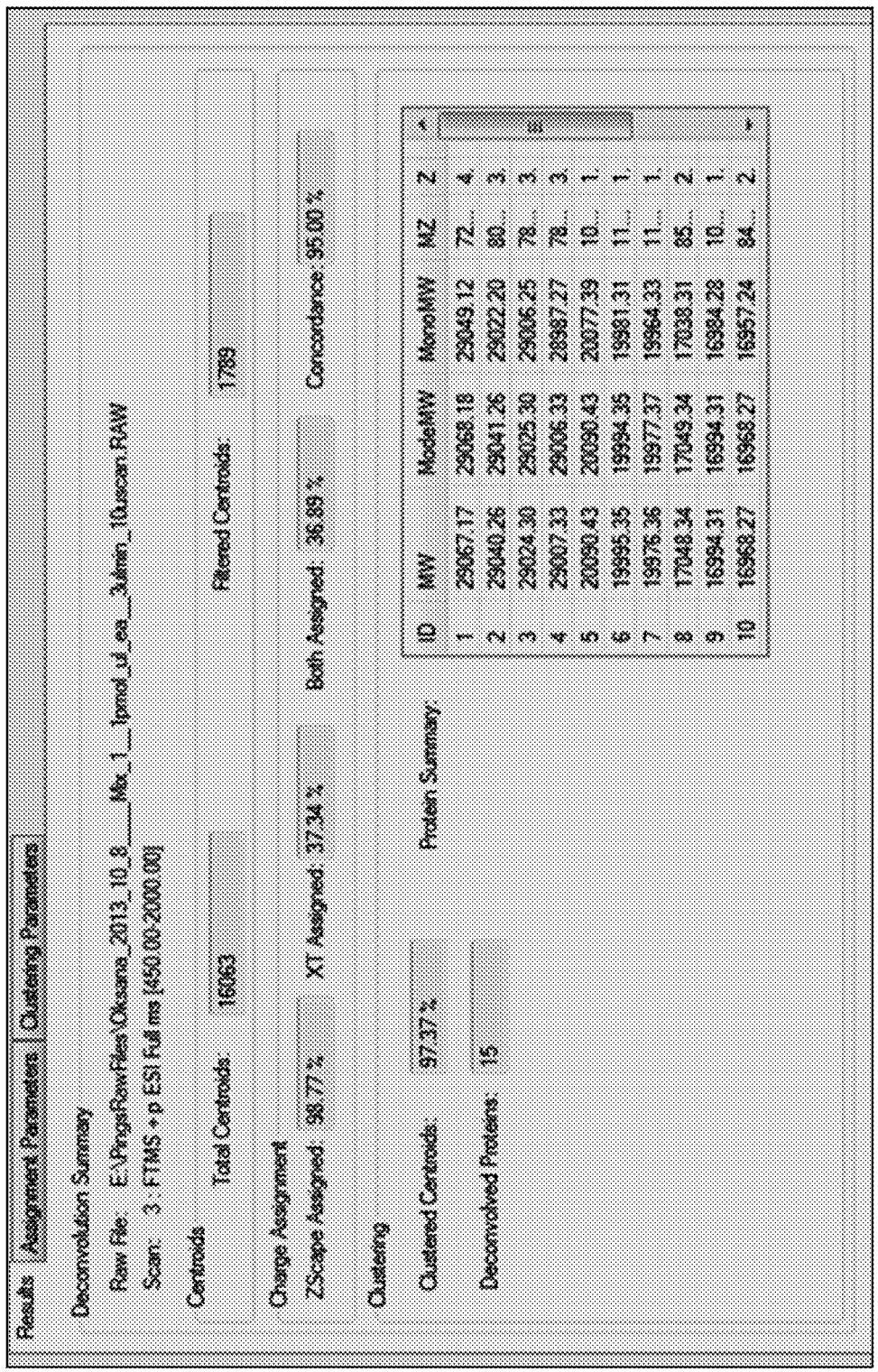

Output can also be produced in a .puf file format for input into the ProSight™ PC protein identification program. Details of the spectral decomposition results (also referred to herein as "deconvolution" results) can also be stored in a .csv file format for further data analysis. The deconvolution summary in the "Results" tab lists the data file(s) and scan(s)

analyzed to produce the report. Moving down the tab are the total number of centroids detected along with the number filtered as part of the program. The percentage of peaks successfully receiving charge-state assignments is found in the "Zscape" box along with a comparison to results (indicated by "XT" on the results tab illustrated in FIG. 11A) as calculated by one of the leading existing deconvolution programs (known as Extract) currently used by those skilled in the state-of-the-art. The "both assigned" and "concordance" boxes measure the agreement between the two programs. Moving to the bottom of the "Results" tab, the percentage of cluster assigned and the total number of unique proteins deconvoluted are shown. An expanded view of this tab is shown in FIG. 11D.

Two of the tabs located on the right hand side of the display shown in FIG. 11A provide for choosing the assignment and clustering parameters associated with the deconvolution process. In FIG. 11B, the "Assignment Parameters" tab includes the mass accuracy in parts per million (ppm), the minimum peak intensity threshold, the minimum signal-to-noise ratio (s/n) needed, and the lowest and highest charge state expected for the deconvolution process. These parameters are further divided into two columns one each for $MS^1$ and $MS^2$ analysis.

The "Clustering Parameters" tab shown in FIG. 11C is also divided into two columns relating to $MS^1$ and $MS^2$ analysis respectively. Provision is made for user input of the minimum number of contiguous charge states and isotopes for the clustering convergence calculation described above. The "Sufficient Contiguous Charge States", "Sufficient Contiguous Isotopes" and "Mass Separation" parameter input displays are also present on this input tab.

2.6. Examples

Figure 12A:
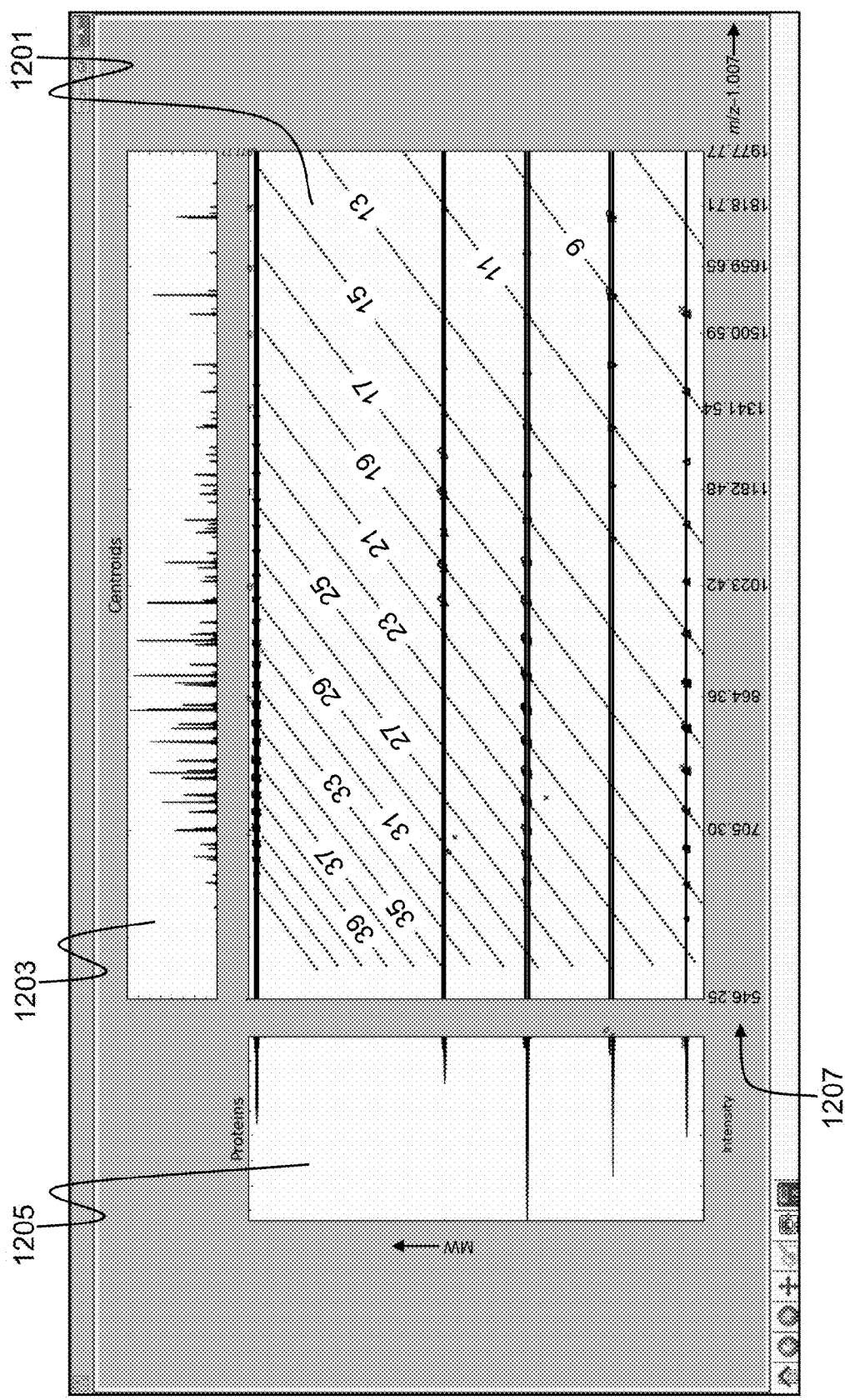
FIG. 12A is a depiction of a computer screen information display illustrating peak cluster decomposition results, as generated by computer software employing methods in accordance with the present teachings, calculated from a mass spectrum of a five-component protein mixture consisting of cytochrome-c, lysozyme, myoglobin, trypsin inhibitor, and carbonic anhydrase.
Figure 12B:
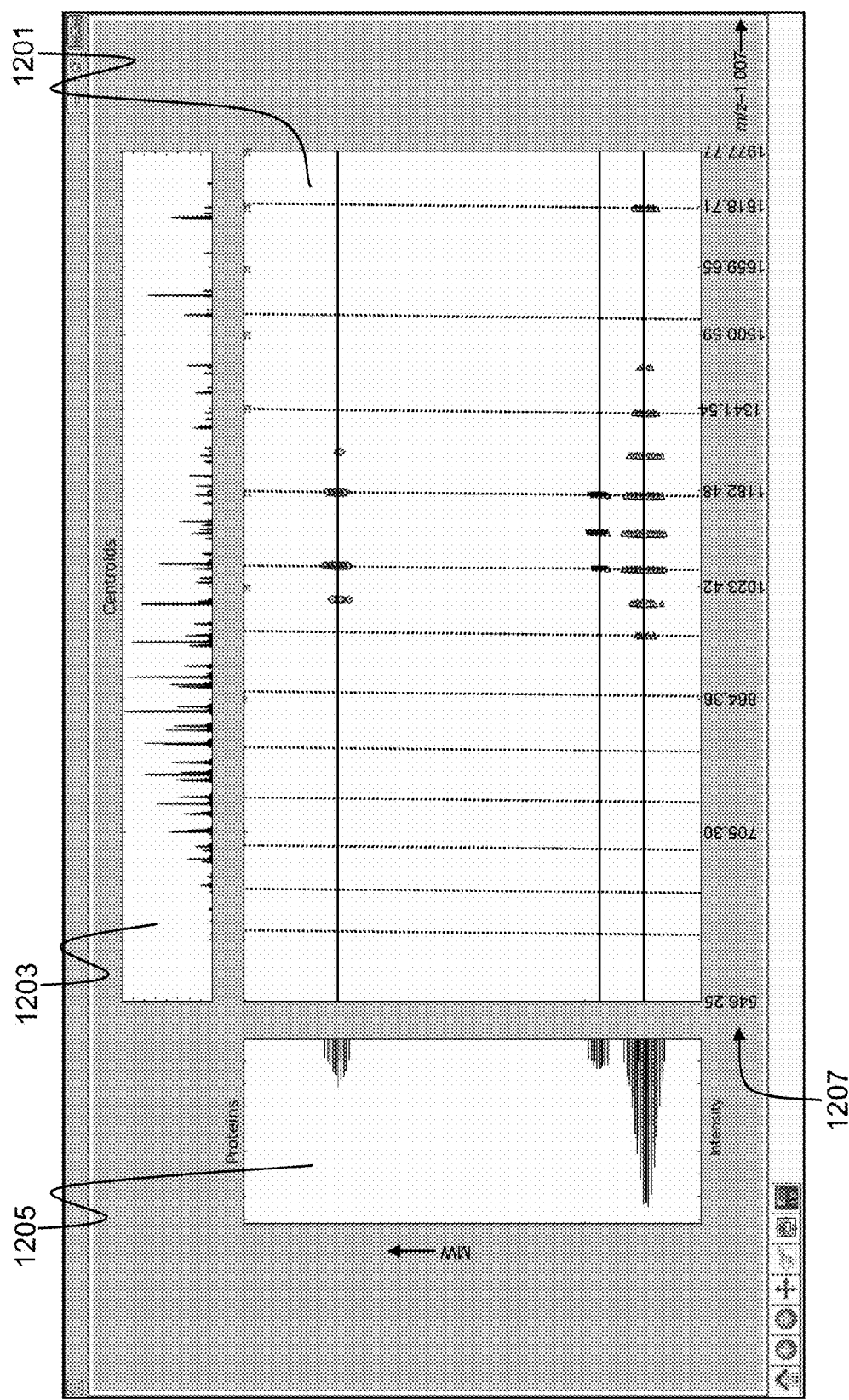
FIG. 12B is a depiction of a computer screen information display illustrating peak cluster decomposition results, as generated by computer software employing methods in accordance with the present teachings, the display illustrating an expanded portion of the decomposition results shown in FIG. 12A.
Figure 12C:
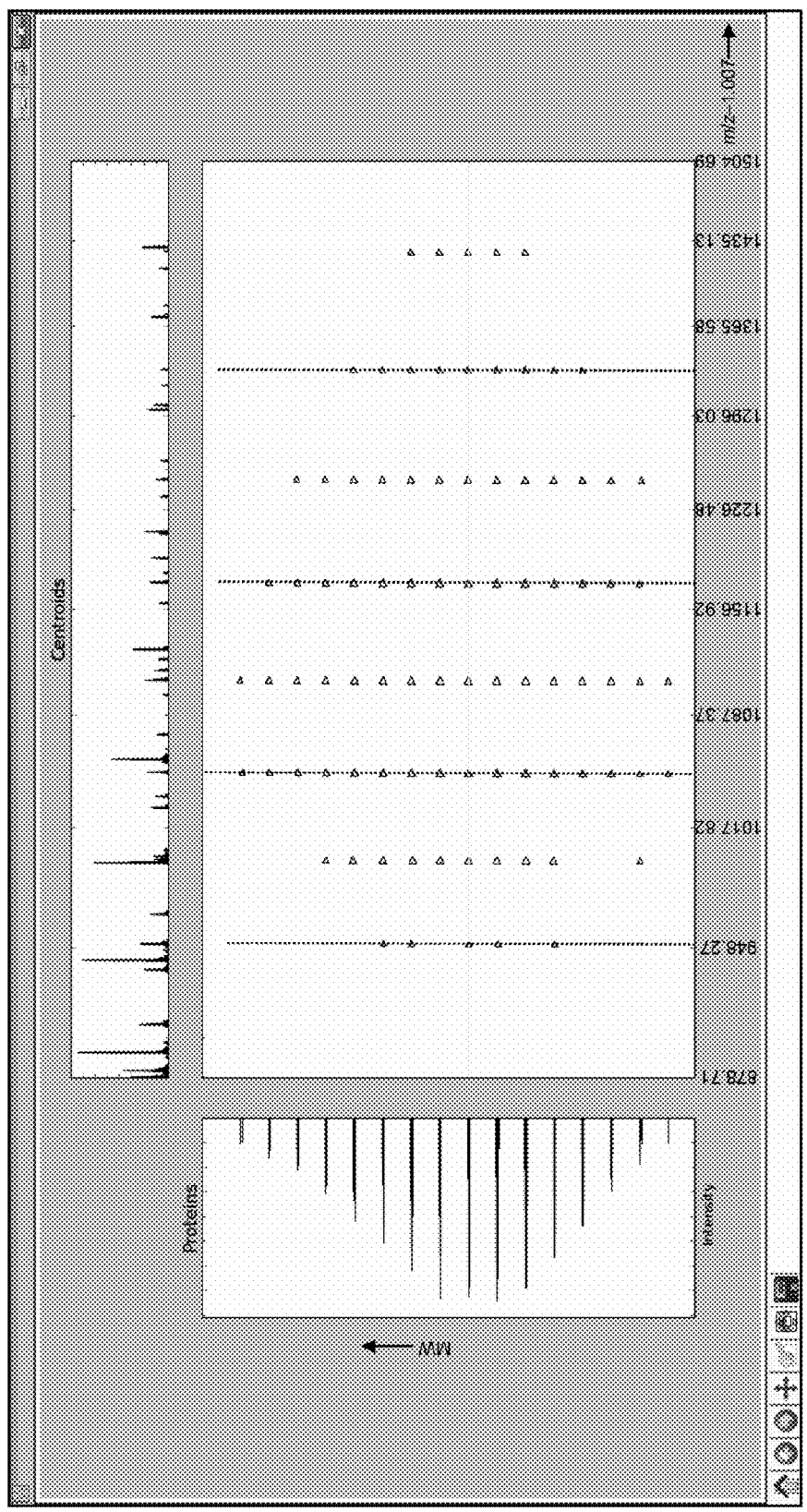
FIG. 12C is a depiction of a computer screen information display illustrating peak cluster decomposition results, as generated by computer software employing methods in accordance with the present teachings, the display illustrating an even-further expanded portion of the decomposition results shown in FIG. 12B.

FIG. 12A shows the deconvolution result from a five component protein mixture consisting of cytochrome c, lysozyme, myoglobin, trypsin inhibitor, and carbonic anhydrase. A top display panel 1203 of the display shows the acquired data from the mass spectrometry represented as centroids. A centrally located main display panel 1201 illustrates each peak as a respective symbol. The horizontally disposed mass-to-charge (m/z) scale 1207 for both the top panel 1203 and central panel 1201 is shown below the central panel. The computer display may also include (not specifically shown in FIG. 12A) the settings for mass accuracy (expressed in ppm), the peaks/isotope cluster setting, the minimum intensity threshold and signal-to-noise settings, and the minimum and maximum charge states associated with the calculation. The panel 1205 on the left hand side of the display shows the calculated molecular weight(s), in daltons, of protein molecules. The molecular weight (MW) scale of the side panel 1205 is oriented vertically on the display, which is perpendicular to the horizontally oriented m/z scale 1207 that pertains to detected ions. Each horizontal line in the central panel 1201 indicates the detection of a protein in this example with the dotted contour lines corresponding to the ionic charge states, which are displayed as a direct result of the transformation calculation discussed previously. In FIG. 12B is shown a display pertaining to the same data set in which the molecular weight (MW) scale is greatly expanded with respect to the view shown in FIG. 12A. The expanded view of FIG. 12B illustrates well-resolved isotopes for a single protein charge state (lowermost portion of left hand panel 1205) as well as potential adduct or impurity peaks (two present in the display). The most intense of these three molecules is that of trypsin inhibitor protein. A further-expanded view in FIG. 12C shows the exact detail of the trypsin inhibitor protein at the isotopic level. The symbol size used to represent the individual isotopes is scaled according to the intensity of each isotope peak.

Figure 13A:
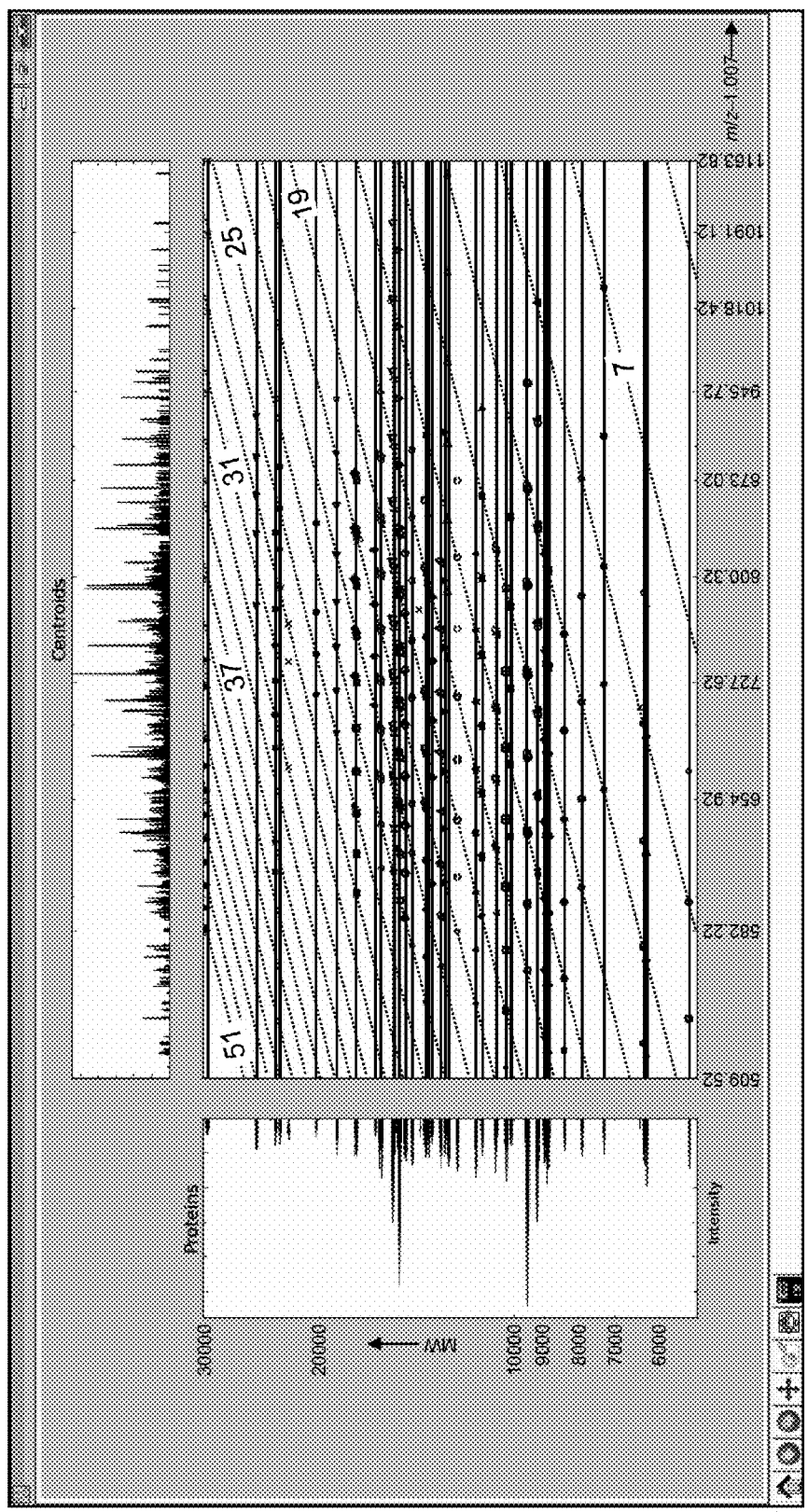
FIG. 13A is a depiction of a computer screen information display illustrating peak cluster decomposition results, as generated by computer software employing methods in accordance with the present teachings, the display illustrating peak cluster decomposition results calculated from a single-stage mass spectrum of a crude extract from the bacterium *E. coli* directly infused into a mass spectrometer.
Figure 13B:
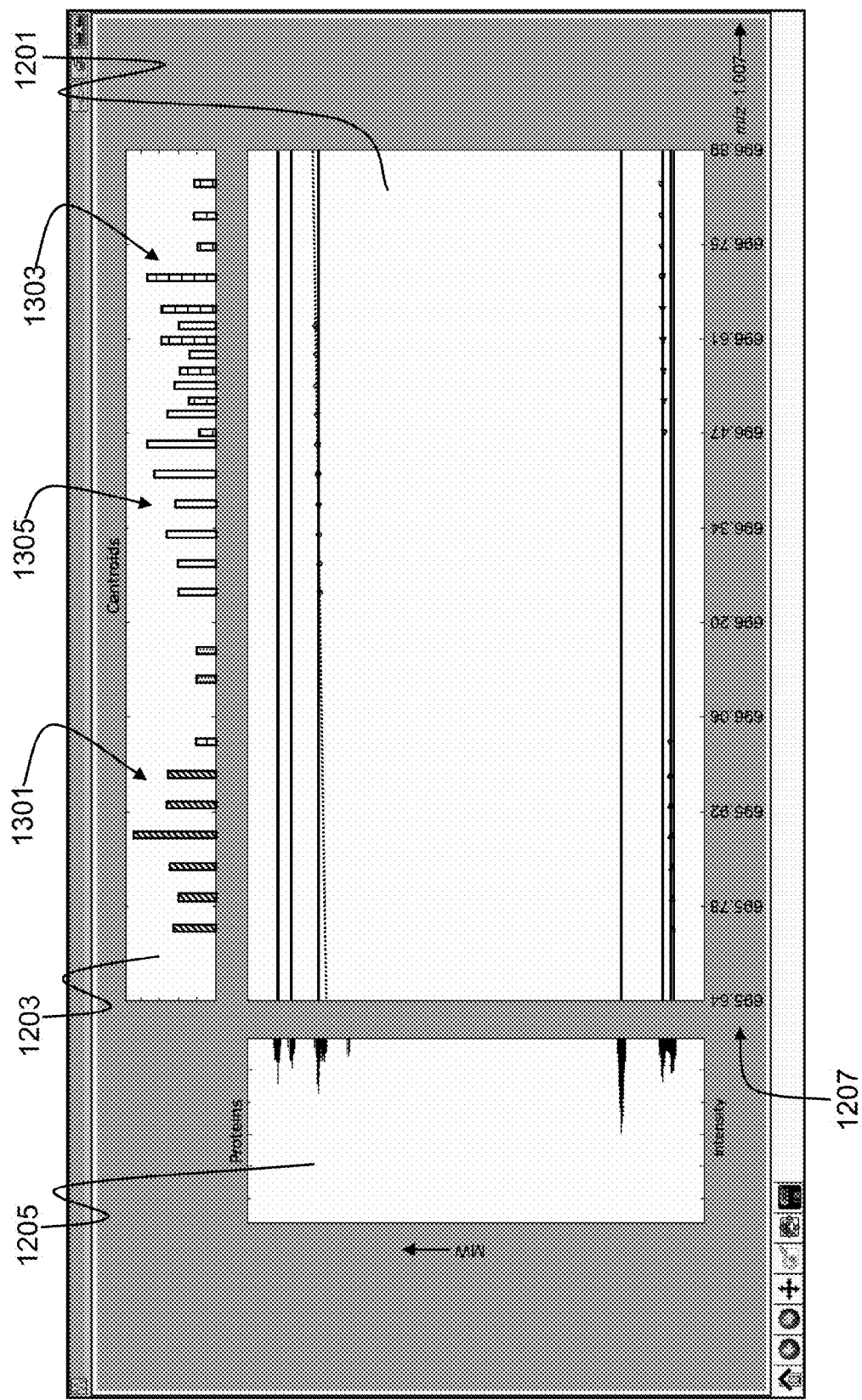
FIG. 13B is a depiction of a computer screen information display illustrating peak cluster decomposition results, as generated by computer software employing methods in accordance with the present teachings, the display illustrating an expanded portion of the decomposition results shown in FIG. 13A.
Figure 13C:
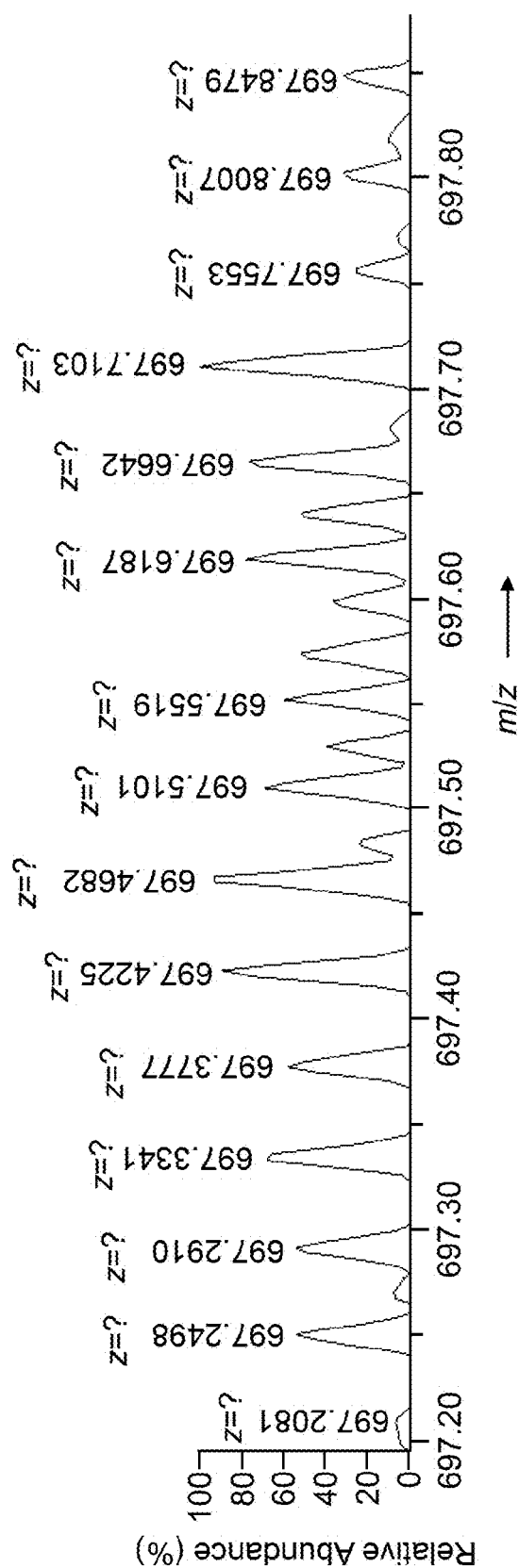
FIG. 13C is a depiction of the mass spectral data whose peak cluster decomposition is shown in FIGS. 13A-13B, showing peak positions and charge-state assignments as provided by a conventional mass spectral peak analysis computer program.
Figure 13D:
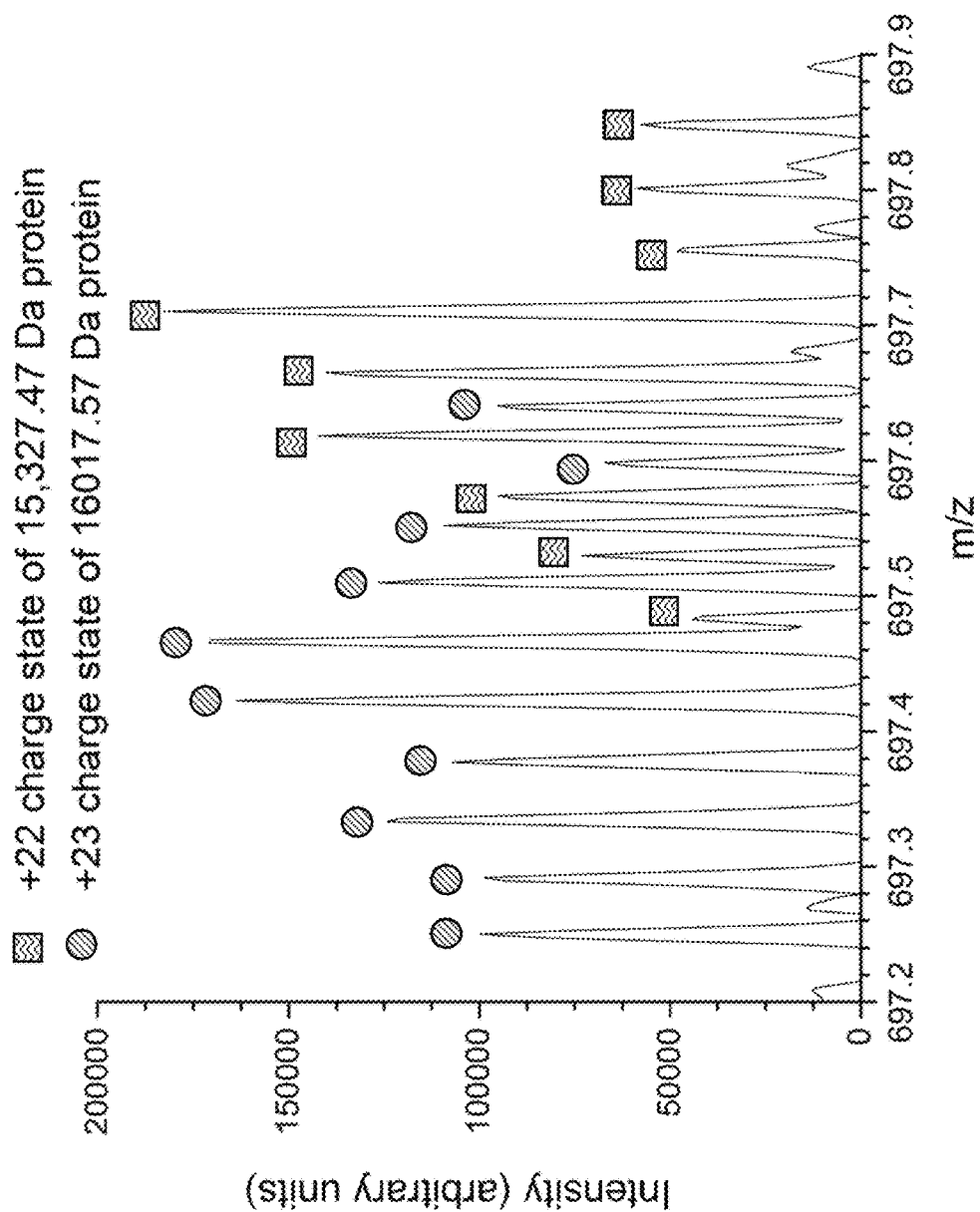
FIG. 13D is a depiction of the mass spectral data whose peak cluster decomposition is shown in FIGS. 13A-13B, showing charge-state assignments as provided by methods in accordance with the present teachings.

FIG. 13A shows the data and deconvolution results of a crude extract from the bacterium E. coli. This sample was directly infused into the mass spectrometer using only a single stage of mass spectrometry. The calculated results, obtained using methods in accordance with the present teachings, indicate the presence of 58 unique discernable proteins in this sample. Many of the proteins in this example have overlapping charge states which are easily clustered using the aforementioned algorithm. FIG. 13B illustrates another display corresponding to the same data set showing an expanded view of the m/z scale in the vicinity of m/z=700 Dale (as well as an expanded view of the MW scale in Daltons) showing three distinct charge states depicted by differently patterned centroids in the top panel 1203. The centroids 1301 in the top panel 1203 of the display correspond to a +22 isotopically resolved charge state of a protein of mass 15,305.76 Da. In this case, this is the only charge state distribution present in the displayed window (note that there are other charge states for this protein over all m/z space), yet the algorithm correctly identifies the cluster even though the centroid bars 1303 and 1305 occur within 1 Da of the charge state in question. Many currently available deconvolution programs cannot correctly assign charge state to independent distributions (two different proteins) within a 3 Da window. Also, the centroid bars 1305 represent the +23 charge state of a protein from E. coli of mass 16,017.57 Da. Note that the +23 charge state of this protein directly overlaps with the centroid bars 1303 of a separate +22 charge state protein of mass 15327.47 Da. Typical deconvolution programs are unable to correctly assign peaks in spectra having this kind of closely spaced or overlapping charge states as can be seen by comparison to FIG. 13C, which shows the same mass spectrum acquired and processed using a program employing a conventional algorithm. The conventional approach is unable to make any charge state assignments in this region of the spectrum, as is indicated by the "question marks" over the peaks of interest in the figure. FIG. 13D has the correctly labeled charge states of the original profile data as assigned by our algorithm employing the novel methods taught herein for the two overlapping charge states described above.

Figure 14A:
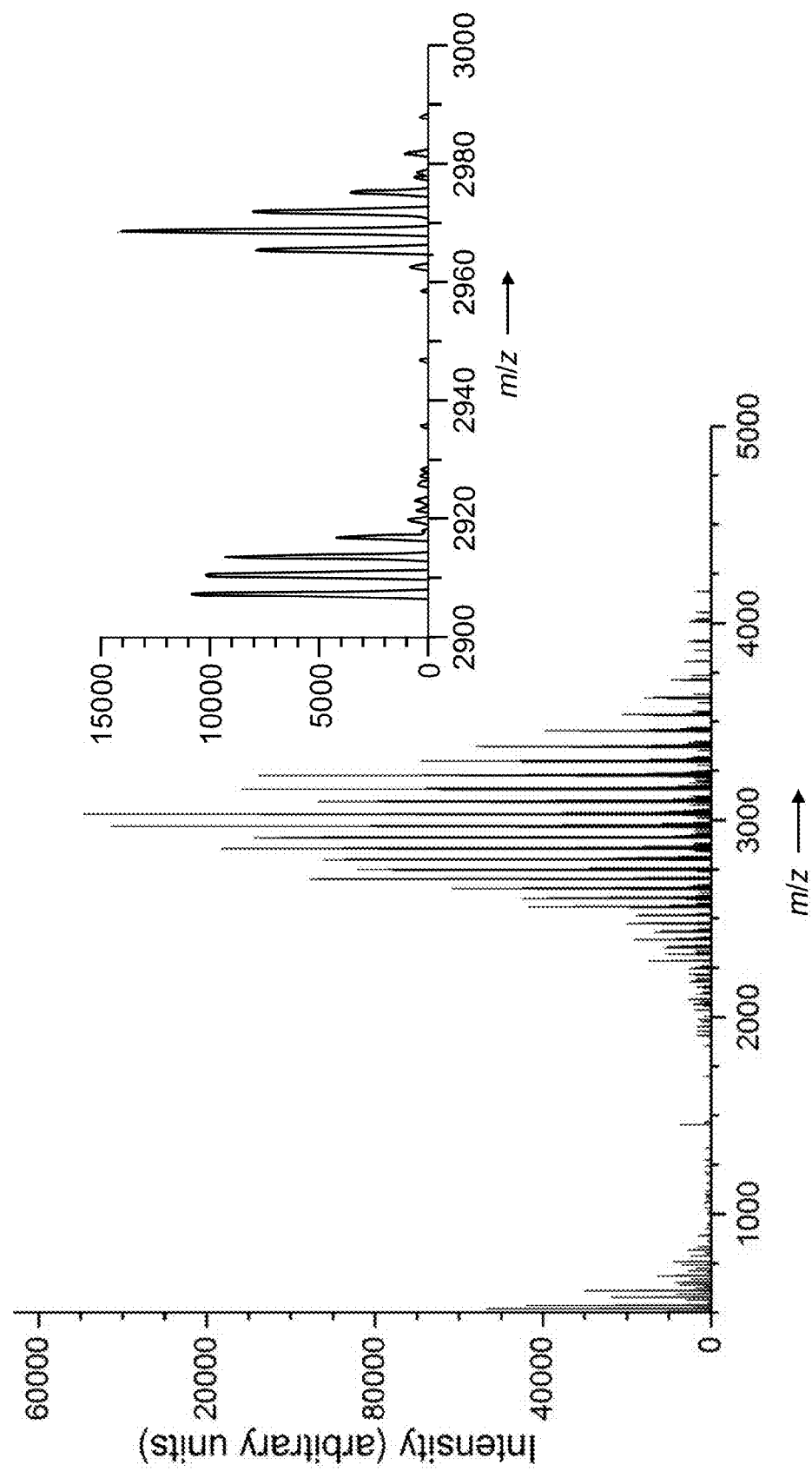
FIG. 14A is a depiction of a mass spectrum of an intact antibody having varying degrees of glycosylation (main plot) also showing (inset) an expanded portion of the spectrum illustrating the different glycoforms of the antibody.
Figure 14B:
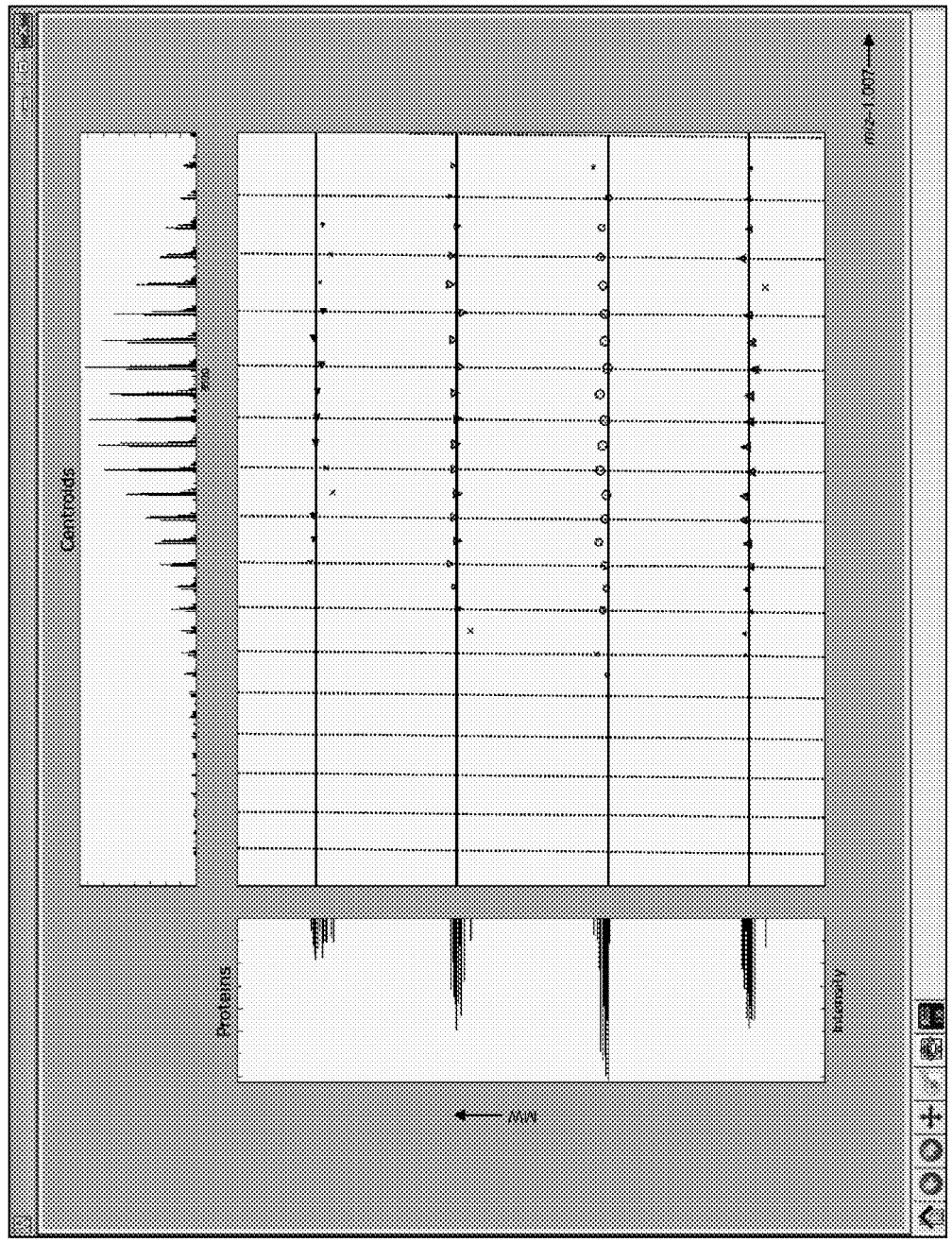
FIG. 14B is a depiction of a computer screen information display illustrating peak cluster decomposition results, as generated by computer software employing methods in accordance with the present teachings, calculated from the mass spectral data shown in FIG. 14A, showing the calculated molecular weights of the four decomposed glycoforms of the antibody ranging from 148378 Da to 148763 Da.

The program employing methods in accordance with the present teachings can also determine charge states for those peaks that do not contain individually resolved isotopes. In another example, illustrated in FIG. 14A, the mass spectrum of an intact antibody is shown with varying degrees of glycosylation. An example of the different glycoforms of the antibody are displayed in the inset of FIG. 14A. FIG. 14B illustrates the deconvoluted molecular weights of the four deconvoluted glycoforms ranging from 148378 Da to 148763 Da.

Figure 15A:
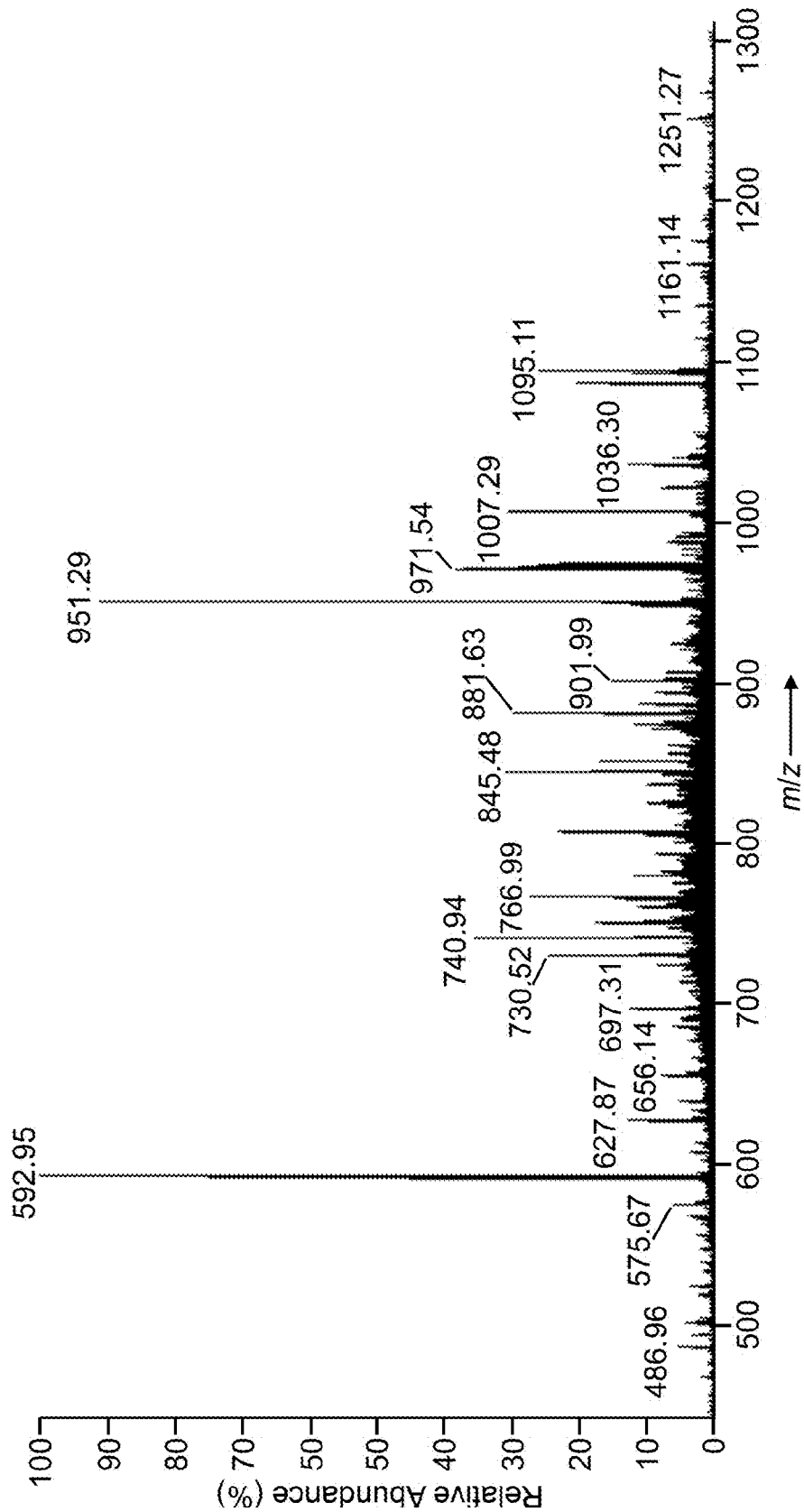
FIG. 15A is a depiction of an $MS^2$ spectrum of the protein carbonic anhydrase II, generated by collision-induced dissociation of the +26 charge state of the protein occurring at m/z=807.00 Da, showing peak assignments as determined by a conventional mass spectral analysis method.
Figure 15B:
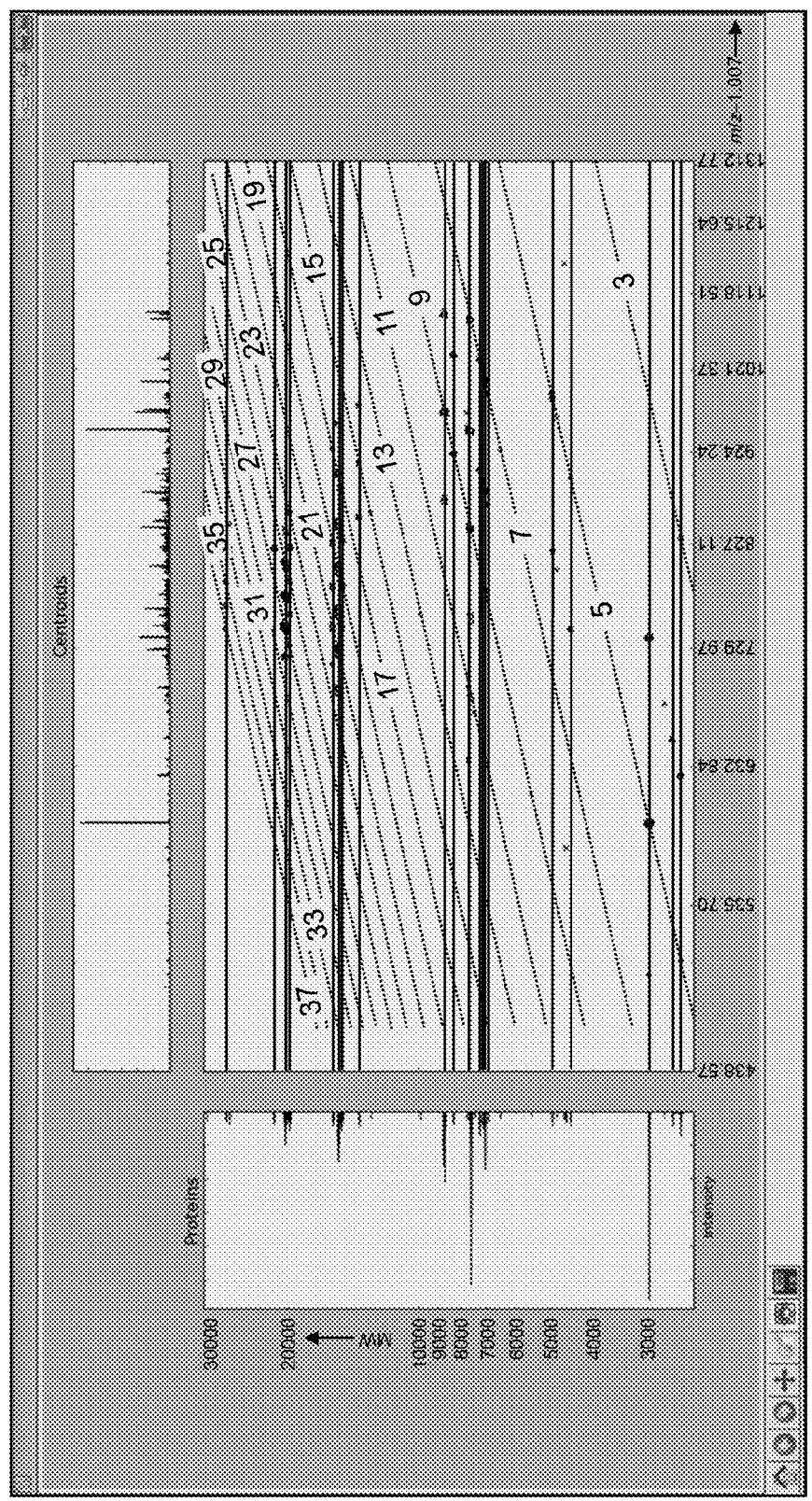
FIG. 15B is a depiction of a computer screen information display illustrating peak cluster decomposition results, as generated by computer software employing methods in accordance with the present teachings, calculated from the $MS^2$ mass spectral data shown in FIG. 15A.
Figure 15C:
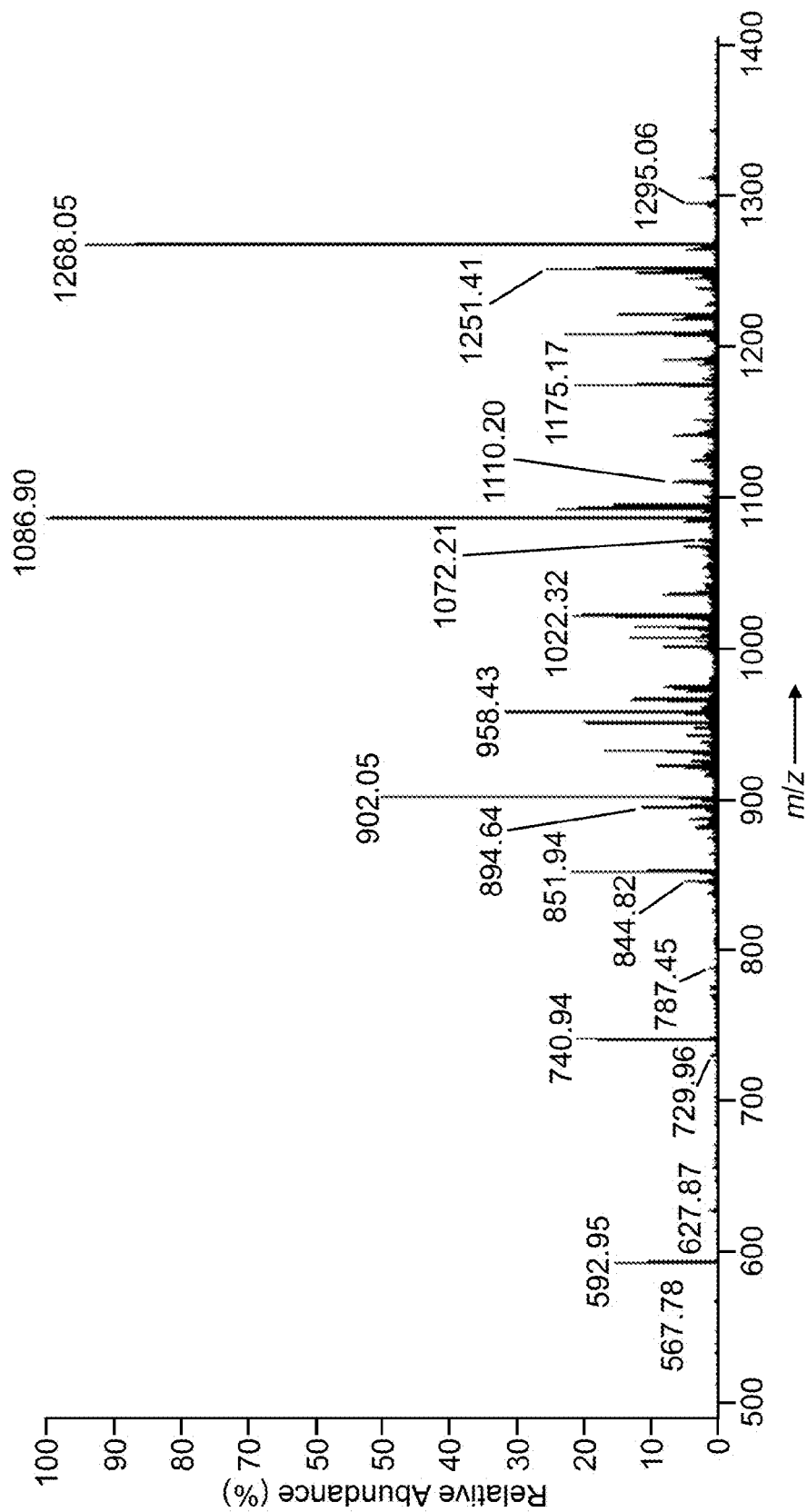
FIG. 15C is a depiction of a second $MS^2$ spectrum of the protein carbonic anhydrase II, generated by collision-induced dissociation of the +21 charge state of the protein at m/z=1001.00 Da, showing peak assignments as determined by a conventional mass spectral analysis method.
Figure 15D:
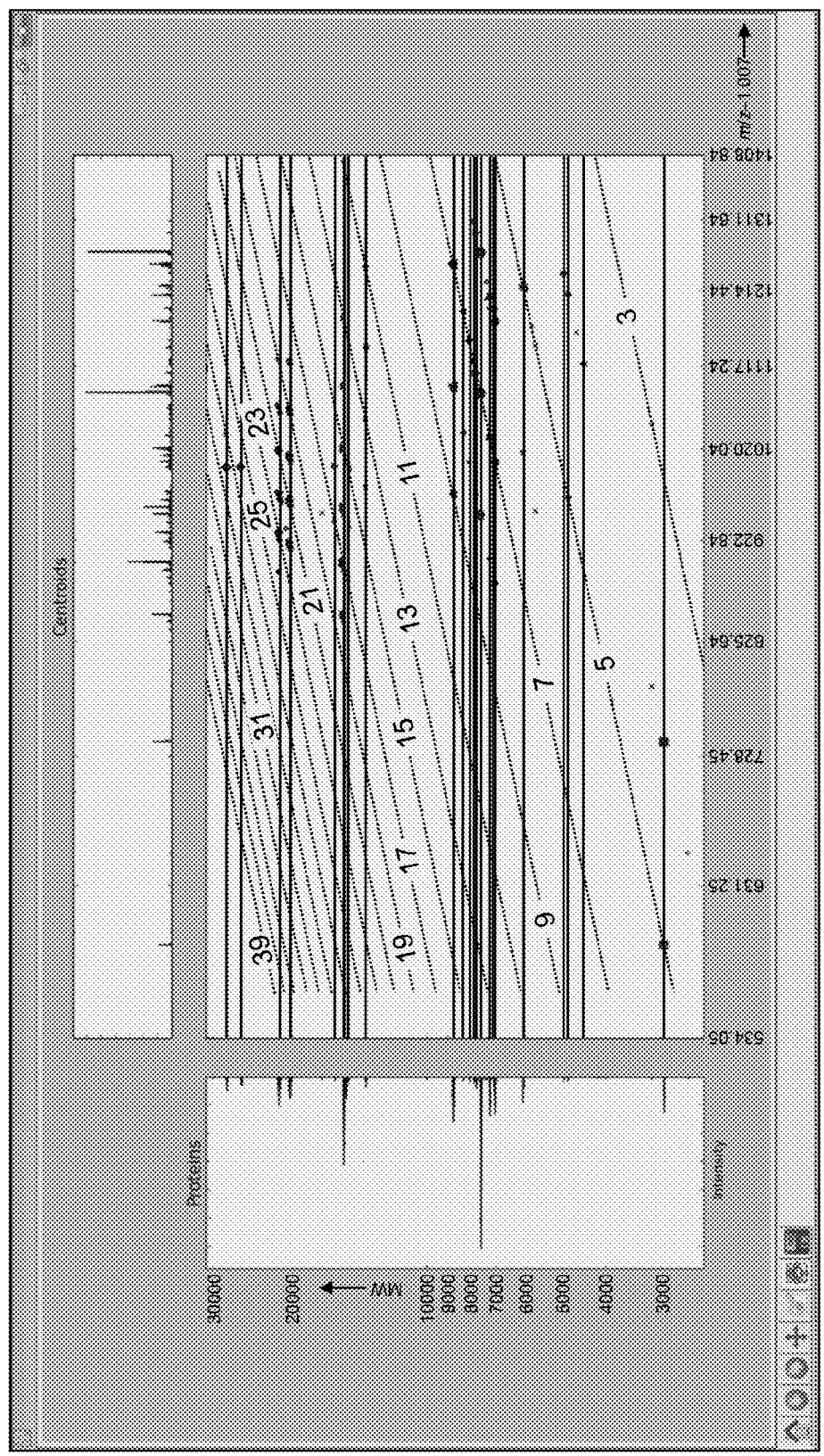
FIG. 15D is a depiction of a computer screen information display illustrating peak cluster decomposition results, as generated by computer software employing methods in accordance with the present teachings, calculated from the $MS^2$ mass spectral data shown in FIG. 15C.

The methods in accordance with the present teachings also have utility for deconvoluting tandem mass spectrometry data. In another example, as illustrated in FIGS. 15A and 15B, two charge states from the protein carbonic anhydrase II were selected for collisional activated dissociation. In FIGS. 15A and 15B are shown the MS/MS spectrum and corresponding deconvolution of the +36 charge state of carbonic anhydrase II at m/z 807.00. Here 64% of the centroids were correctly identified compared to only 9% using the conventional algorithm. Exactly 50% of the centroids were clustered even in the event where many MS/MS fragments do not produce multiple charge states of the same fragment. The total number of fragment ions identified correctly was 35. FIGS. 15C and 15D show the MS/MS fragmentation and deconvolution of the +21 charge state of carbonic anhydrase II at m/z 1001. Here 74% of the centroids were clustered and 78% of the charge states were assigned correctly. A total of 49 fragments ions were identified using the program.

The inventors have investigated the performance of the deconvolution portions of the present teachings for the analyses of proteins in biologically-derived samples. To assess the accuracy and precision of results calculated using methods in accordance with the present teachings, repeated mass spectral analyses were performed of a sample consisting of an equimolar mixture of the five compounds: Ribonuclease A, Myoglobin, Trypsin Inhibitor, Carbonic Anhydrase and Enolase. For each of the listed protein compounds, except for Enolase, ten random individual scans were selected for performing the molecular weight calculations, each individual scan selected from a random data file. In the case of Enolase, only five such random scans were selected due to the nature of experiments from which the data was derived.

For each selected scan, an average molecular weight, a statistical modal value molecular weight and a monoisotopic molecular weight were derived from the observed (i.e., calculated) results, where the statistical average and statistical mode were taken over all isotopic variants. A mean value and a sigma (standard deviation, σ) value of the average, modal and monoisotopic molecular weights were then calculated across the set of selected files chosen for each compound. These latter values are tabulated and compared with theoretical values in Table 2 of FIG. 16. The columns labeled "PPM Error" relate to the deviations of the means of the observed average, modal and monoisotopic values from theoretical values (also shown). The upper and lower values tabulated in each cell of the first "PPM error" column pertain to the errors in the average and mode molecular weights, respectively. There is no monoisotopic calculation for Enolase, since resolved isotopes were not observed. The somewhat larger error in the monoisotopic calculation for carbonic anhydrase is due to the fact that not all the charge states of this protein can be resolved to the isotopic level. Nonetheless, the derived accuracy and precision is considered to be acceptable for protein identifications as well as for use in data-dependent ion selection and fragmentation.

Figure 17:
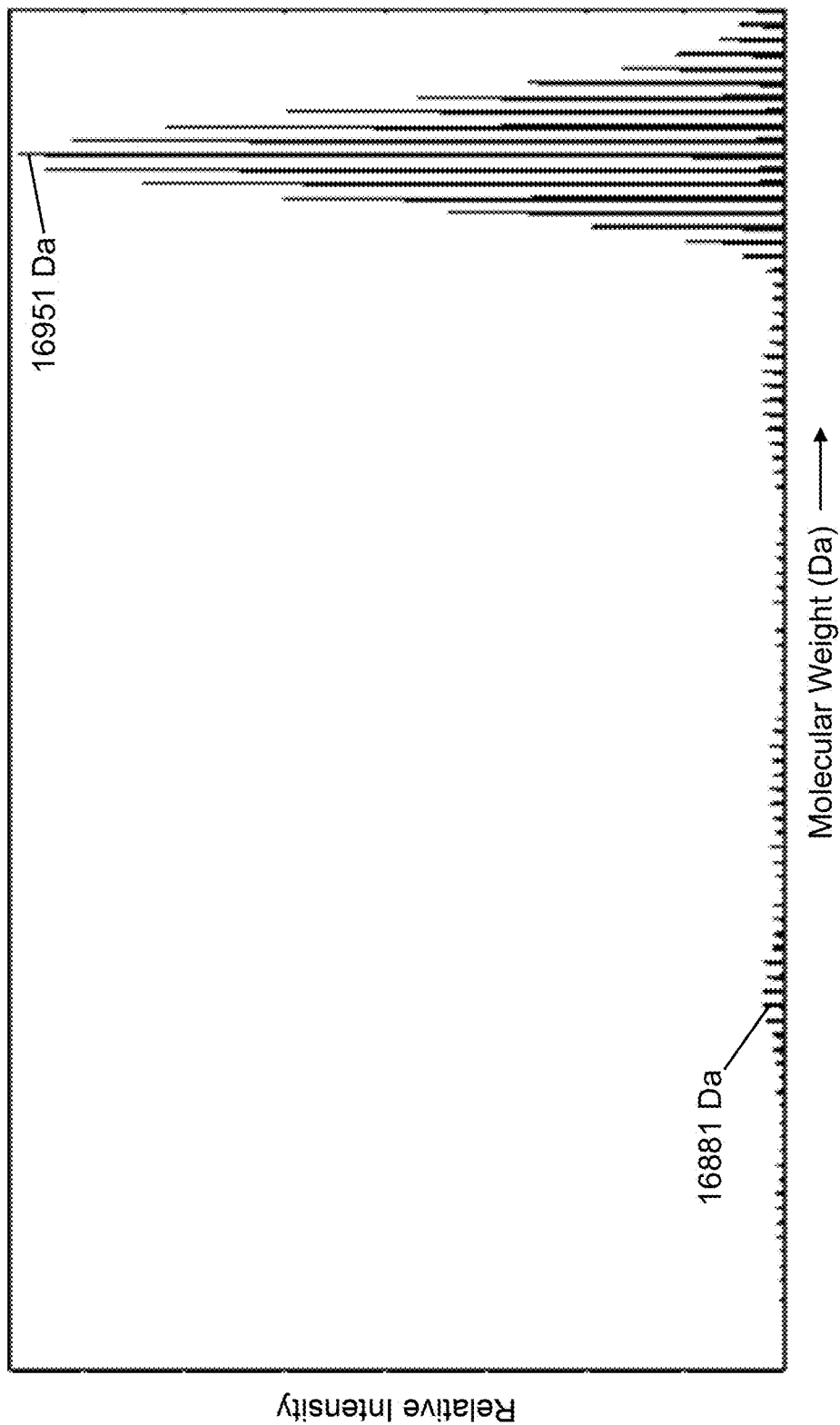
FIG. 17 is a portion of a plot of calculated molecular weights, as calculated in accordance with the presently taught methods, from a mass analysis of a mixture of five standard proteins including isotopic variants.

FIG. 17 is a portion of a plot of molecular weights (including isotopic variants), calculated using the presently taught methods, from a mass analysis of a mixture of five standard proteins including isotopic variants. The measured intensity of the most intense centroid (at 16951 Da) in the isotopic cluster spanning a range from about 16943-16960 Da is 1535928 (in arbitrary units). By contrast, the most intense centroid (at 16881 Da) in the isotopic cluster spanning the approximate range from about 16874-16888 Da is 22484. Centroids of even less intensity in other isotopic clusters are also resolved by the deconvolution methods. FIGS. 18A-18B show calculated molecular weights of selected proteins from an E. Coli lysate, after reaction with a proton transfer reagent. The intensity of the most intense centroid, at 9190 Da, shown in FIG. 18A is 26874 (in arbitrary units); the intensity of the most intense centroid, as 14722 Da, shown in FIG. 18B is 183. From such results, the inventors conclude that the presently taught methods can provide useful measurements over a signal intensity range (roughly corresponding to an analyte abundance range of at least two orders of magnitude.

FIG. 19 is a table (Table 3) of molecular weights of proteins that are diagnostic for distinguishing between closely related bacterial species using deconvolution methods in accordance with the present teachings. The tabulated results shown in Table 3 were obtained in a study to evaluate the ability of the presently taught methods to correctly differentiate very closely related species that other approaches (including MALDI) cannot successfully differentiate. Table 3 lists only those molecular weights that are unique to each of the microorganisms listed. In order to generated the tabulated molecular weight values listed in Table 3, observed values were grouped into 5 Da "bins" under the restriction that an observed molecular weight of each listed protein must appear in a bin in at least fifty percent of replicate samples in order to be considered as a "marker" for that protein. The rounding of molecular weight values associated with the binning procedure is the reason why last digit of each tabulated mass value is either a "2" or a "7".

FIG. 20 is a table (Table 4) of the accuracy of identifications of various yeast species, all from the genus *Candida*, using mass spectrometric analyses for which multiple overlapping mass spectral lines are deconvoluted and grouped in accordance with methods in accordance with the present teachings.

2.7. Directing Data Dependent Acquisition to Avoid Redundant Measurements

In the traditional approach to setting up a dynamic exclusion list, m/z values are placed on the list for a specified time period, which approximates the average peak width of a given compound/type of compound. When using such an approach with small molecules or peptides (i.e. tryptic peptides which typically have the same physiochemical properties), it works well to increase the dynamic range associated with the compound identification process. On the contrary, intact proteins (as are measured in top-down proteomics studies) widely vary in sizes, amino acid compositions, physiochemical properties, and 3-D structures. This variability typically leads to many more sites on the protein (than would be the case for smaller-molecule analytes) interacting with the stationary phase of a chromatographic column. The result is that some peaks may be only a few seconds wide while others can persist on the order of minutes. A typical example of the variability that can be expected is illustrated in FIG. 2, showing the varying peak profiles obtained from a single chromatographic run. Therefore, the standard approach to dynamic exclusion is not an ideal fit for top-down analysis. To rectify this problem, the present methods employ a signal intensity ranking system to determine for how long the charge states associated with a given protein should be placed on the dynamic exclusion list. In this new approach, the seed centroid of each cluster is put on the exclusion list. When a new seed centroid is proposed in subsequent $MS^1$ scan, a check is first made to determine if the new centroid clusters with any of the seed centroids presently on the selection list in step 510. If so, a check is made to determine if the intensity of the new centroid has fallen below a threshold (as a fraction of the intensity of the original seed centroid). Only when the intensity does fall below the threshold, will the original seed centroid be taken off of the exclusion list (step 515).

Alternatively, all charge states from a given protein can be placed on the exclusion list, thus eliminating selecting different charge states from the same protein for tandem MS analysis. While these charge states are on the dynamic exclusion list, the signal intensity of the peaks comprising the list are monitored until they are below a defined minimum intensity or there is an increase in signal from one of the charge states at a defined mass difference (ppm), indicating the presence of two components of differing mass and charge but the same m/z value. It was mentioned above that, for the purpose of making data-dependent mass isolation and fragmentation decisions in "real-time", a deconvolution algorithm on which such decisions are based should be able to perform the calculation procedure in roughly the same amount of time required for a mass spectrometer to perform a tandem mass analysis (i.e., a full MS/MS analysis). Typically, this requires the calculations to be performed in less than one second. To assess the calculation speed of the presently-taught methods, the inventors have made a set of repeated executions of the calculations used to generate the results that are displayed in various of the accompanying drawings. FIG. 22 is a table (Table 6) of the times required for five different executions of each calculation. The timings shown in Table 6 indicate that the calculation speed is sufficient for use in real-time data dependent acquisition.

The discussion included in this application is intended to serve as a basic description. Although the present invention has been described in accordance with the various embodiments shown and described, one of ordinary skill in the art will readily recognize that there could be variations to the embodiments without departing from the scope of the present invention as defined in the claims. The reader should be aware that the specific discussion may not explicitly describe all embodiments possible; many alternatives are implicit. For instance, although the methods of the present teachings have been described using examples based on protein analyses, the methods taught herein are also applicable to many other biomolecules, especially various oligomer molecules such as a variety of oils as well as RNA or DNA oligonucleotides and telomeres. Accordingly, many modifications may be made by one of ordinary skill in the art without departing from the scope of the invention and neither the description nor the terminology is intended to limit the scope of the invention. Any patents, patent publications or technical publications or technical documents mentioned within this disclosure are hereby incorporated by reference herein. If any statements in the mentioned documents should conflict with statements made in this application, then the present application will control.

What is claimed is:

1. A method for mass spectral analysis of a sample containing a plurality of intact protein molecule species, said method including repeatedly introducing a respective portion of the sample into an ionization source of a mass spectrometer; and using the ionization source to generate, from each sample portion, a population of first-generation multi-protonated ions that comprises a plurality of first-generation ion species generated from each respective intact protein molecule species of said each portion, each ion species comprising a respective charge state, z, and mass-to-charge (m/z) ratio, the method comprising:
   (a) mass analyzing a plurality of first-generation ions generated from a first one of the sample portions, thereby generating a mass spectrum thereof, wherein each ion species generated from a protein is represented in the mass spectrum by a respective m/z ratio and a corresponding respective intensity;
   (b) automatically recognizing, for each of two or more intact protein molecule species, a respective subset of the m/z ratios corresponding to a set of first-generation ion species generated from said each intact protein molecule species and automatically determining a respective charge state, z, for each m/z ratio of each subset;
   (c) selecting, from each recognized subset, a single representative m/z ratio;
   (d) isolating, for each representative m/z ratio, a respective sub-population of ions having said each representative m/z ratio from ions having other m/z ratios; and
   (e) fragmenting each isolated sub-population of ions so as to generate second-generation ion species,
   wherein the step (b) includes:
     (b1) automatically assigning a tentative charge state to each m/z ratio measured in step (a) that corresponds to an above-threshold intensity;
     (b2) automatically adjusting the assigned tentative charge states to thereby generate a set of self-consistent assigned charge states; and
     (b3) decomposing the assigned charge states into analyte-specific clusters of charge states, each analyte-specific cluster being a one of the subsets of the m/z ratios.

2. A method as recited in claim 1, wherein:
a one of the selected representative m/z ratios corresponds to a peak of the mass spectrum having a peak intensity that is less than a peak intensity of a second peak of the mass spectrum whose m/z ratio belongs to a different recognized subset and which is not a selected representative m/z ratio.

3. A method as recited in claim 1, wherein:
a first one of the selected representative m/z ratios corresponds to a peak of the mass spectrum having a peak intensity that is at least two orders of magnitude greater than a peak intensity of a second peak of the mass spectrum that corresponds to a second one of the selected representative m/z ratios.

4. A method as recited in claim 1, wherein:
a one of the selected representative m/z ratios corresponds to a peak of the mass spectrum having a peak intensity that is less than a peak intensity of a second peak of the mass spectrum that corresponds to another m/z ratio included in the same recognized subset of m/z ratios as said one of the selected representative m/z ratios.

5. A method as recited in claim 1, wherein:
the step (b) includes representing each mass spectrum peak as a respective centroid.

6. A method as recited in claim 1, wherein the repeated introducing of a respective portion of the sample into an ionization source of a mass spectrometer is performed in the absence of prior chromatographic separation of the sample into chromatographic fractions.

7. A method as recited in claim 1, further comprising, after the automatic recognition step (b), the step of:
determining a molecular weight of an intact protein molecule species from the m/z ratios and determined charge states of a recognized subset of the m/z ratios.

8. A method for mass spectral analysis as recited in claim 1, further comprising:
   (f) mass analyzing a plurality of first-generation ion species that are generated from a different, second one of the sample portions;
   (g) for each representative m/z ratio of each previously recognized subset of m/z ratios, comparing a respective corresponding intensity, detected during step (f), to a threshold intensity; and
   (h) for each representative m/z ratio at which the corresponding intensity detected in step (f) is greater than or equal to the threshold intensity, performing the steps of:

(h1) isolating a respective sub-population of ions having said each representative m/z ratio from ions having other m/z ratios; and
(h2) fragmenting each isolated sub-population of ions so as to generate second-generation ion species.
9. A method for mass spectral analysis as recited in claim 1, further comprising:
(f) mass analyzing a plurality of first-generation ion species that are generated from a different, second one of the sample portions;
(g) for each m/z ratio of each previously recognized subset of m/z ratios, comparing a respective corresponding intensity, detected during step (f), to a threshold intensity; and
(h) adding, to an exclusion list, any representative m/z ratio that is a member of a previously recognized subset for which the respective corresponding detected intensity of each m/z ratio of said subset is less than the threshold intensity,
wherein the exclusion list comprises m/z ratios corresponding to ions which are temporarily excluded from isolation and fragmentation.
10. A method for mass spectral analysis as recited in claim 1, wherein the repeated introducing of a respective portion of the sample into an ionization source of a mass spectrometer comprises introducing a continuous flow of eluate discharged from a liquid chromatograph into the ionization source, the method further comprising:
(f) mass analyzing a plurality of first-generation ion species that are generated from a different, second one of the sample portions;
(g), automatically recognizing any additional m/z ratios detected in step (f) that were not observed during the execution of step (a);
(h) automatically determining if each additional m/z ratio corresponds to an intact protein molecule species for which there exists a previously recognized subset of m/z ratios; and
(i) automatically assigning each additional m/z ratio that corresponds to an intact protein molecule species for which there exists a previously recognized subset of m/z ratios as a member of said subset.
11. A method for mass spectral analysis as recited in claim 1, wherein the repeated introducing of a respective portion of the sample into an ionization source of a mass spectrometer comprises introducing a continuous flow of eluate discharged from a liquid chromatograph into the ionization source, the method further comprising:
(f) mass analyzing a plurality of first-generation ion species that are generated from a different, second one of the sample portions;
(g) automatically recognizing any additional m/z ratios detected in step (f) that were not observed during execution of step (a);
(h) automatically determining if each additional m/z ratio detected in step (f) corresponds to an intact protein molecule species for which there exists a previously recognized subset of m/z ratios; and
(i) automatically recognizing at least one additional subset of m/z ratios if any additional m/z ratio detected in step (f) does not correspond to an intact protein molecule species for which there exists a previously recognized subset of m/z ratios and assigning at least one additional m/z ratio to a one of the additional recognized subsets.
12. A method for mass spectral analysis as recited in claim 1, further comprising:
(f) mass analyzing a second plurality of first-generation ion species that are generated from a different, subsequent one of the sample portions;
(g) detecting intensities that correspond to m/z ratios that are elements of subsets of m/z ratios previously recognized in step (b); and
(h) if a detected intensity corresponding to an m/z ratio that is an element of a previously-recognized subset, as detected in step (g), is greater than or equal to a threshold intensity and its corresponding m/z ratio is not listed on an exclusion list and if a detected intensity of a representative m/z ratio that corresponds to the previously-recognized subset of which the detected m/z ratio is a member is below the threshold intensity, performing the additional steps of:
(h1) isolating a sub-population of ions having the said corresponding m/z ratio; and
(h2) fragmenting the isolated sub-population of ions having the detected said corresponding m/z ratio.
13. A method for mass spectral analysis as recited in claim 1, wherein the repeated introducing of a respective portion of the sample into an ionization source of a mass spectrometer comprises introducing a continuous flow of fluid sample to the ionization source.
14. A method for mass spectral analysis as recited in claim 13, wherein the continuous flow of fluid sample comprises a continuous flow of eluate discharged from a liquid chromatograph.
15. A method for mass spectral analysis as recited in claim 1, wherein the repeated introducing of a respective portion of the sample into an ionization source of a mass spectrometer comprises repeated ionization of a respective sample portion by laser-assisted desorption and ionization.
16. A method for mass spectral analysis as recited in claim 1, wherein the step (b) of automatically recognizing, for each of two or more intact protein molecule species, a respective subset of the m/z ratios comprises a mathematical process in which intensities of m/z values are represented as Boolean values.
17. A method as recited in claim 1, wherein:
the step (b1) comprises:
determining, for each of a plurality of probe charge states of each m/z value for which the corresponding detected intensity is greater than a threshold value, a plurality of additional probe m/z values at which mass spectral signatures of isotopic variants and charge-state variants of a same protein are theoretically expected to occur;
tabulating a respective score for each of said probe charge states based on intensities, as detected in step (a), corresponding to the probe m/z values; and
assigning the tentative charge states based on statistical analyses of the scores; and
the step (b3) comprises grouping together all detected m/z values having assigned charge state, z, values for which the calculated masses, m, differ by an integral number of replacements of $C^{12}$ atoms by $C^{13}$ atoms, within statistical error.
18. A method as recited in claim 1, wherein the sample is a solution comprising a mixture of the intact protein molecule species.
19. A method as recited in claim 18 wherein the solution comprising the mixture of the intact protein molecule species is an extract derived from a bacterium.
20. A method as recited in claim 19, further comprising:
determining a respective molecular weight of each of two or more of the intact protein molecule species; and determining a bacterium species identification based on the determined two or more molecular weights of the intact protein molecule species.

21. A method as recited in claim 19, wherein the repeated introducing of a respective portion of the sample to an ionization source comprises introducing a continuous flow of the bacterium extract to the ionization source during direct infusion, of the sample into the mass spectrometer.

22. A method as recited in claim 21, wherein at least one of the sample portions includes four or more unique intact protein molecule species.

23. A method as recited in claim 19, wherein the repeated introducing of a respective portion of the sample to an ionization source comprises:
   introducing the bacterium extract into a liquid chromatographic column;
   performing a partial chromatographic separation of the intact protein molecule species of the bacterium extract using the liquid chromatographic column, wherein the chromatographic column is operated such that all of the intact protein molecule species elute from the column during a time span of not greater than five minutes; and
   introducing a continuous flow of eluate discharged from the liquid chromatographic column to the ionization source, the continuous flow including all of the sample portions.

24. A method as recited in claim 23, wherein at least one of the sample portions includes four or more unique intact protein molecule species.

25. A method as recited in claim 23, wherein the step (b) is performed in not more than one second.

26. A method as recited in claim 18, wherein the step (b) is performed in not more than one second.

* * * * *

UNITED STATES PATENT AND TRADEMARK OFFICE
CERTIFICATE OF CORRECTION

PATENT NO. : 10,217,619 B2
APPLICATION NO. : 15/067727
DATED : February 26, 2019
INVENTOR(S) : Ping F. Yip et al.

Page 1 of 1

It is certified that error appears in the above-identified patent and that said Letters Patent is hereby corrected as shown below:

In the Claims

Claim 10, Column 33, Line 32:
Replace "(g),"
With --(g)--

Claim 12, Column 34, Line 19:
Replace "having the detected said corresponding m/z ratio"
With --having the said corresponding m/z ratio--

Claim 21, Column 35, Line 8:
Replace "direct infusion, of the sample"
With --direct infusion of the sample--

Signed and Sealed this
First Day of October, 2019

Andrei Iancu
*Director of the United States Patent and Trademark Office*